United States Patent
Takizawa et al.

(10) Patent No.: US 8,740,774 B2
(45) Date of Patent: Jun. 3, 2014

(54) CAPSULE-TYPE MEDICAL APPARATUS, GUIDANCE SYSTEM AND GUIDANCE METHOD THEREFOR, AND INTRASUBJECT INSERTION APPARATUS

(71) Applicants: Hironobu Takizawa, Tokyo (JP); Hironao Kawano, Tokyo (JP); Akio Uchiyama, Kanagawa (JP); Shinsuke Tanaka, Tokyo (JP); Atsushi Chiba, Tokyo (JP)

(72) Inventors: Hironobu Takizawa, Tokyo (JP); Hironao Kawano, Tokyo (JP); Akio Uchiyama, Kanagawa (JP); Shinsuke Tanaka, Tokyo (JP); Atsushi Chiba, Tokyo (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 0 days.

(21) Appl. No.: 13/788,621

(22) Filed: Mar. 7, 2013

(65) Prior Publication Data

US 2013/0184526 A1 Jul. 18, 2013

Related U.S. Application Data

(62) Division of application No. 12/089,017, filed as application No. PCT/JP2006/319999 on Oct. 5, 2006, now abandoned.

(30) Foreign Application Priority Data

Oct. 5, 2005 (JP) ................................. 2005-293012
Dec. 2, 2005 (JP) ................................. 2005-349180

(51) Int. Cl.
*A61B 1/04* (2006.01)
*A61B 1/00* (2006.01)
*A61N 2/00* (2006.01)
*A61B 18/04* (2006.01)
*A61B 19/00* (2006.01)

(52) U.S. Cl.
USPC ............. 600/117; 600/109; 600/114; 600/12; 606/33; 128/899

(58) Field of Classification Search
CPC ............ A61B 5/06; A61B 1/041; A61B 1/05; A61B 1/31; A61N 2/00
USPC .............. 348/65; 600/117, 101, 109, 114, 12, 600/409, 424, 431, 420, 118; 606/33; 128/899; 607/116, 103
See application file for complete search history.

(56) References Cited

U.S. PATENT DOCUMENTS 3,500,853 A * 3/1970 Freeman ........................ 137/112
(Continued)

FOREIGN PATENT DOCUMENTS

JP 60-56488 12/1985
(Continued)

OTHER PUBLICATIONS

European Search Report mailed Jan. 30, 2013 in connection with corresponding EP Application No. EP 06 81 1326.
(Continued)

*Primary Examiner* — John P Leubecker
*Assistant Examiner* — Ronald D Colque
(74) *Attorney, Agent, or Firm* — Ostrolenk Faber LLP

(57) ABSTRACT

Using a guidance system with a simple configuration, propulsive motion along a longitudinal direction and changing of the propulsion direction are easily performed with good precision and stability. There is provided a capsule-type medical apparatus which is inserted into the body of a subject and is guided by an external magnetic field, the capsule-type medical apparatus comprising: a substantially cylindrical capsule; a propulsion mechanism for converting rotary motion about a longitudinal axis R of the capsule into propulsive motion along the longitudinal axis R; a magnet accommodated inside the capsule and disposed in such a manner that the magnetic-pole direction thereof can be switched between a direction along the longitudinal axis R and a direction intersecting the longitudinal axis R; and a securing portion for securing the magnet to the capsule in each of the switched states of the magnetic-pole direction.

4 Claims, 33 Drawing Sheets

(56) References Cited

U.S. PATENT DOCUMENTS

| | | | |
|---|---|---|---|
| 3,720,895 A * | 3/1973 | Schlesinger, Jr. | 335/205 |
| 3,760,312 A * | 9/1973 | Shlesinger, Jr. | 335/205 |
| 4,186,362 A * | 1/1980 | Kondo et al. | 335/205 |
| 4,527,153 A * | 7/1985 | Suzuki et al. | 340/572.2 |
| 4,762,130 A | 8/1988 | Fogarty | |
| 5,308,354 A | 5/1994 | Zacca | |
| 5,337,732 A | 8/1994 | Grundfest | |
| 5,353,807 A | 10/1994 | DeMarco | |
| 5,423,745 A | 6/1995 | Todd | |
| 5,484,411 A | 1/1996 | Inderbitzen | |
| 5,601,537 A | 2/1997 | Frassica | |
| 5,681,336 A | 10/1997 | Clement | |
| 5,727,552 A | 3/1998 | Ryan | |
| 5,868,662 A | 2/1999 | Borodulin | |
| 5,871,475 A | 2/1999 | Frassica | |
| 5,989,230 A | 11/1999 | Frassica | |
| 6,129,706 A | 10/2000 | Janacek | |
| 6,245,040 B1 | 6/2001 | Inderbitzen | |
| 6,390,967 B1 | 5/2002 | Forman | |
| 6,500,186 B2 | 12/2002 | Lafontaine | |
| 6,605,056 B2 | 8/2003 | Eidenschink | |
| 6,679,860 B2 | 1/2004 | Stiger | |
| 6,771,000 B2 * | 8/2004 | Kim et al. | 310/209 |
| 6,975,055 B2 * | 12/2005 | Joong et al. | 310/156.01 |
| 7,172,610 B2 | 2/2007 | Heitzmann | |
| 7,623,904 B2 * | 11/2009 | Uchiyama et al. | 600/424 |
| 7,686,824 B2 | 3/2010 | Konstantino | |
| 7,909,799 B2 | 3/2011 | Frassica | |
| 7,955,350 B2 | 6/2011 | Konstantino | |
| 8,038,600 B2 | 10/2011 | Uchiyama | |
| 8,043,313 B2 | 10/2011 | Krolik | |
| 8,080,026 B2 | 12/2011 | Konstantino | |
| 8,317,678 B2 | 11/2012 | Frassica | |
| 2002/0026174 A1 | 2/2002 | Wallace | |
| 2002/0077520 A1 | 6/2002 | Segal | |
| 2002/0151918 A1 | 10/2002 | Lafontaine | |
| 2003/0020810 A1 | 1/2003 | Takizawa | |
| 2003/0060734 A1 | 3/2003 | Yokoi | |
| 2003/0078606 A1 | 4/2003 | Lafontaine | |
| 2003/0125788 A1 | 7/2003 | Long | |
| 2003/0181788 A1 | 9/2003 | Yokoi et al. | |
| 2004/0138552 A1 | 7/2004 | Harei | |
| 2004/0143287 A1 | 7/2004 | Konstantino | |
| 2004/0158270 A1 | 8/2004 | Wyzgala | |
| 2004/0186349 A1 | 9/2004 | Ewers | |
| 2004/0236180 A1 | 11/2004 | Uchiyama | |
| 2004/0243158 A1 | 12/2004 | Konstantino | |
| 2005/0021071 A1 | 1/2005 | Konstantino | |
| 2005/0049509 A1 | 3/2005 | Mansour | |
| 2005/0054912 A1 | 3/2005 | Garibaldi et al. | |
| 2005/0085696 A1 * | 4/2005 | Uchiyama et al. | 600/160 |
| 2005/0124875 A1 | 6/2005 | Kawano | |
| 2005/0137458 A1 | 6/2005 | Sakamoto | |
| 2005/0177130 A1 | 8/2005 | Konstantino | |
| 2005/0200207 A1 * | 9/2005 | Hasegawa et al. | 310/10 |
| 2005/0251108 A1 | 11/2005 | Frassica | |
| 2005/0272976 A1 | 12/2005 | Tanaka | |
| 2005/0288730 A1 | 12/2005 | Deem | |
| 2006/0100480 A1 | 5/2006 | Ewers | |
| 2006/0135870 A1 | 6/2006 | Webler | |
| 2006/0206002 A1 | 9/2006 | Frassica | |
| 2006/0265049 A1 | 11/2006 | Gray | |
| 2007/0161851 A1 | 7/2007 | Takizawa | |
| 2007/0299301 A1 | 12/2007 | Uchiyama | |

FOREIGN PATENT DOCUMENTS

| | | |
|---|---|---|
| JP | 2003-111720 | 4/2003 |
| JP | 2003-325438 | 11/2003 |
| JP | 2004-255174 | 9/2004 |
| JP | 2005-52502 | 3/2005 |

OTHER PUBLICATIONS

International Search Report mailed Jan. 9, 2007 in corresponding PCT International Appln. No. PCT/JP2006/319999.

* cited by examiner

CAPSULE-TYPE MEDICAL APPARATUS, GUIDANCE SYSTEM AND GUIDANCE METHOD THEREFOR, AND INTRASUBJECT INSERTION APPARATUS

CROSS-REFERENCE TO RELATED APPLICATIONS

This application is a divisional of U.S. application Ser. No. 12/089,017, filed Apr. 2, 2008 by Hironobu TAKIZAWA et al., entitled CAPSULE-TYPE MEDICAL APPARATUS, GUIDANCE SYSTEM AND GUIDANCE METHOD THEREFOR, AND INTRASUBJECT INSERTION APPARATUS, which is a 35 U.S.C. §§371 national phase conversion of PCT/JP2006/319999, filed Oct. 5, 2006, which claims priority of Japanese Patent Application Nos. 2005-293012 and 2005-349180, filed Oct. 5, 2005 and Dec. 2, 2005, respectively, the disclosures of which have been incorporated herein by reference. The PCT International Application was published in the Japanese language.

TECHNICAL FIELD

The present invention relates to a capsule-type medical apparatus, a guidance system and a guidance method therefor, and an intrasubject insertion apparatus which is inserted into a body cavity and advances while rotating.

BACKGROUND ART

Capsule-type medical apparatuses that have spiral ridges, extending along the longitudinal axes, formed on the outer circumferential surfaces of substantially cylindrical capsules thereof and that include, in the capsules, permanent magnets whose magnetic poles are aligned in a direction orthogonal to the longitudinal axes are well known (refer to, for example, Patent Document 1).

In such a capsule-type medical apparatus, the capsule can be rotated about the longitudinal axis thereof by drawing upon the property that the permanent magnet therein rotates so as to align its magnetic-pole direction in the direction of an external magnetic field produced in a working space thereof when the external magnetic field is rotated about the longitudinal axis of the capsule. Since the spiral ridge is formed on the outer circumferential surface of the capsule, when the capsule is rotated about the longitudinal axis thereof while the spiral ridge is in contact with, for example, tissue outside the capsule, the rotational motion about the longitudinal axis is converted into propulsive motion in a direction along the longitudinal axis by means of the spiral ridge. In this manner, the capsule can be guided to a desired position using its ability to move in a direction along the longitudinal axis thereof.

Furthermore, capsule-type medical apparatuses having, in substantially cylindrical capsules thereof, permanent magnets whose magnetic poles are aligned in the direction of the longitudinal axes of the capsules are also known (refer to, for example, Patent Document 2).

In such a capsule-type medical apparatus, the orientation of the capsule can be changed by moving the permanent magnet therein so as to orient itself along a direction of an external magnetic field produced in the working space of the capsule-type medical apparatus. In addition, the capsule can be propelled in the direction of the longitudinal axis thereof by changing the external magnetic field to a gradient magnetic field.

Furthermore, a known example of an intrasubject insertion apparatus that is inserted into a body cavity and advanced while rotating is described in Patent Document 3. The intracorporeal guiding device described in this Patent Document 3 has an inflatable and deflatable membrane member, constituting a spiral-structured portion, formed on the outer surface of a rotating member provided at a front-end portion of an endoscope thereof. In this intracorporeal guiding device, the above-described membrane member is wound so as to extend obliquely with respect to the center of rotation of the rotating member. By doing so, as the above-described rotating member is rotated, the rotating member is endowed with a propulsion force through a screwing operation relative to a wall in the lumen, thereby propelling the front-end portion of the endoscope.

Patent Document 1: Japanese Unexamined Patent Application, Publication No. 2004-255174

Patent Document 2: Japanese Unexamined Patent Application, Publication No. 2003-111720

Patent Document 3: Japanese Examined Patent Application, Publication No. S60-56488

DISCLOSURE OF INVENTION

The guidance system of the capsule-type medical apparatus described in Patent Document 2 is problematic in that the apparatus is complicated because a three-dimensional gradient magnetic field needs to be formed with high accuracy in order to appropriately guide the capsule-type medical apparatus in the body. Furthermore, it is difficult to precisely control the speed and position of the capsule-type medical apparatus with a technique producing a propulsion force based on a gradient magnetic field.

On the other hand, with the guidance system of the capsule-type medical apparatus described in Patent Document 1, since the rotational motion of the capsule is converted into propulsive motion in the direction of the longitudinal axis through the spiral ridge formed on the outer circumferential surface of the cylindrical capsule, the propulsion speed and the position of the capsule can be controlled precisely according to the lead of the spiral ridge by controlling the rotational speed of the capsule. In addition, the structure of the apparatus can be made simple because no gradient magnetic field is required as an external magnetic field but instead a magnetic field with uniform intensity is rotated.

However, the capsule-type medical apparatus described in Patent Document 1 has a disadvantage in that it is not possible to easily change the orientation thereof in a desired direction since it is designed to advance mainly in a direction of the longitudinal axis thereof.

In the intracorporeal guiding device described in Patent Document 3, when the inflation pressure of the above-described membrane member becomes high, the gaps between adjacent ridges of the spiral become small, and the wall in a lumen, such as the intestinal wall, does not easily creep between ridges of the spiral. For this reason, the above-described intracorporeal guiding device experiences poor contact between the membrane member and the wall in the lumen, which significantly decreases the propulsion force produced by the screwing operation. On the other hand, in the above-described intracorporeal guiding device, when the inflation pressure of the membrane member becomes low, it is difficult to maintain the spiral shape, which also reduces the propulsion force produced by the screwing operation.

The present invention has been conceived in light of the above-described circumstances, and an object thereof is to provide a capsule-type medical apparatus and a guidance system and a guidance method therefor which allow propulsive motion in a direction along the longitudinal axis and allow the propulsion direction to be changed with high accuracy and stability without complicating the guidance system.

Another object of the present invention is to provide an intrasubject insertion apparatus that can produce a stable propulsion force by satisfactorily maintaining the spiral shape of a spiral-structured portion.

To achieve the above-described objects, the present invention provides the following solutions.

A capsule-type medical apparatus according to a first aspect of the present invention is a capsule-type medical apparatus which is inserted into the body of a subject and is guided by an external magnetic field. This capsule-type medical apparatus includes a substantially cylindrical capsule; a propulsion mechanism for converting rotary motion about a longitudinal axis of the capsule into propulsive motion along the longitudinal axis; a magnet accommodated inside the capsule and disposed in such a manner that the magnetic-pole direction thereof can be switched between a direction along the longitudinal axis and a direction intersecting the longitudinal axis; and a securing portion for securing the magnet to the capsule in each of the switched states of the magnetic-pole direction.

According to the first aspect of the present invention, by switching the magnetic-pole direction of the magnet accommodated in the capsule to a direction along the longitudinal axis of the capsule and holding the magnet at that position with the securing portion, when an external magnetic field with an arbitrary direction is applied, the longitudinal axis of the capsule can be aligned in a direction along the direction of the external magnetic field. Therefore, the capsule can be oriented in a desired direction by changing the direction of the external magnetic field.

Furthermore, by switching the magnetic-pole direction of the magnet to a direction intersecting the longitudinal axis of the capsule and holding the magnet at that position with the securing portion, when an external magnetic field rotating about the longitudinal axis of the capsule is applied, the capsule can be rotated about the longitudinal axis. Since the capsule includes the propulsion mechanism, when the capsule is rotated about the longitudinal axis, the capsule moves in a straight line along the longitudinal axis due to the operation of the propulsion mechanism. Therefore, the capsule can be propelled in a direction along the longitudinal axis.

The propulsion mechanism is preferably a spiral mechanism provided on an outer circumferential surface of the capsule.

In the above-described aspect, the magnet may be made of a permanent magnet, and the securing portion may include an engagement member which is engaged with the magnet at a location where the magnetic poles are oriented in a direction along the longitudinal axis and at a location where the magnetic poles are oriented in a direction intersecting the longitudinal axis.

By doing so, due to the operation of the securing portion including the engagement member, the permanent magnet can be held reliably at a location where the permanent magnet is oriented in a direction along the longitudinal axis or at a location where the permanent magnet is oriented in a direction intersecting the longitudinal axis. Therefore, the capsule can be switched between direction changing and propulsive motion. The engagement member can be disengaged by applying an external force greater than the engagement force.

Furthermore, in the above-described aspect, the magnet may be made of a permanent magnet, and the securing portion may include a magnetic material which is held in contact with the magnet at a location where the magnetic poles are oriented in a direction along the longitudinal axis and at a location where the magnetic poles are oriented in a direction intersecting the longitudinal axis.

By doing so, when the permanent magnet is positioned at a location where the magnetic poles are oriented in a direction along the longitudinal axis or at a location where the magnetic poles are oriented in a direction intersecting the longitudinal axis, the permanent magnet is held at that position in contact with the securing portion made of the magnetic material. Therefore, the capsule can be switched between direction changing and propulsive motion. The permanent magnet can be detached from the magnetic material to change the magnetic-pole direction thereof by applying an external force greater than the attraction force.

Furthermore, in the above-described aspect, a magnetic-pole-direction switching device for switching the magnetic-pole direction of the magnet may be included.

By doing so, with the operation of the magnetic-pole-direction switching device, the magnetic-pole direction of the magnet can be switched reliably to freely switch the capsule between direction changing and propulsive motion.

Furthermore, in the above-described aspect, the magnet may be made of a permanent magnet, the securing portion may include an electromagnet which is held in contact with the magnet at a location where the magnetic poles are oriented in a direction along the longitudinal axis and at a location where the magnetic poles are oriented in a direction intersecting the longitudinal axis, and the magnetic-pole-direction switching device may include a magnetic-pole switching device for switching the magnetic poles of the electromagnet.

By doing so, with the operation of the securing portion including the electromagnet, the magnet is pulled and held by attraction at a location where the magnet is oriented in a direction along the longitudinal axis or at a location where the magnet is oriented in a direction intersecting the longitudinal axis. Furthermore, by switching the magnetic poles of the electromagnet through the operation of the magnetic-pole switching device, the magnet held in contact with the electromagnet can be detached by a magnetic repulsive force to switch between the above-described positions easily and reliably.

Furthermore, in the above-described aspect, the magnet may be made of a permanent magnet, and the magnetic-pole-direction switching device may include a motor for pivoting the magnet about an axis along a radial direction of the capsule.

By doing so, the capsule can be switched between direction changing and propulsive motion easily and reliably by rotating the magnet made of the permanent magnet through the operation of the magnetic-pole-direction switching device including the motor.

Furthermore, in the above-described aspect, the magnet may be made of an electromagnet, and the securing portion and the magnetic-pole-direction switching device may include a magnetic-pole switching device for switching and holding the magnetic poles of the electromagnet.

By doing so, with the operation of the magnetic-pole switching device, the magnetic-pole direction of the magnet made of the electromagnet can be switched between the direction along the longitudinal axis of the capsule and the direction intersecting the longitudinal axis. Therefore, the capsule can be switched between direction changing and propulsive motion easily and reliably.

A capsule-type medical-apparatus guidance system according to a second aspect of the present invention includes one of the above-described capsule-type medical apparatuses; a magnetic-field generating apparatus, disposed outside a working area of the capsule-type medical apparatus, for generating an external magnetic field which acts on the magnet inside the capsule-type medical apparatus; and a magnetic-field control apparatus for controlling the external magnetic field acting on the magnet from the magnetic-field generating apparatus.

According to the second aspect of the present invention, the magnet in the capsule can be switched to a direction along the longitudinal axis of the capsule or a direction intersecting the longitudinal axis by causing an external magnetic field to act upon the magnet in the capsule-type medical apparatus through the operation of the magnetic-field generating apparatus and by controlling the external magnetic field using the magnetic-field control apparatus, thus allowing the guidance system to selectively carry out direction changing and propulsive motion of the capsule. As a result, the capsule can be guided in a desired direction accurately.

In the above-described aspect, a capsule-orientation detection apparatus for detecting an orientation of the capsule-type medical apparatus may be included, and the magnetic-field control apparatus may control the direction of the external magnetic field at a position of the capsule-type medical apparatus according to the orientation of the capsule-type medical apparatus detected by the capsule-orientation detection apparatus.

By doing so, the magnetic-field control apparatus can determine the direction of the external magnetic field that is to act upon the magnet in the capsule-type medical apparatus based on the orientation of the capsule-type medical apparatus detected through the operation of the capsule-orientation detection apparatus. Guidance can be performed in such a manner that if the detected capsule-type medical apparatus is oriented towards the target position, then the orientation of the magnet is switched for propulsive motion to perform propulsive motion, whereas if the detected capsule-type medical apparatus is not oriented towards the target position, then the orientation of the magnet is switched for direction changing to change the direction.

Furthermore, a capsule-type medical-apparatus guidance method according to a third aspect of the present invention is a method for guiding one of the above-described capsule-type medical apparatuses. This guidance method includes propelling the capsule-type medical apparatus in the longitudinal-axis direction by switching and securing the magnetic-pole direction of the magnet to the direction intersecting the longitudinal direction and applying an external magnetic field which rotates about the longitudinal axis; and changing the propulsion direction of the capsule-type medical apparatus by switching and securing the magnetic-pole direction of the magnet to the direction along the longitudinal axis and applying an external magnetic field which is generated in an arbitrary direction.

According to the third aspect of the present invention, the capsule-type medical apparatus can be easily switched between propulsive motion and direction changing merely by switching the magnetic-pole direction of the magnet accommodated in the capsule-type medical apparatus, thereby guiding the capsule-type medical apparatus with high accuracy.

An intrasubject insertion apparatus according to a fourth aspect of the present invention includes an insertion portion main body for insertion into a subject; a rotation mechanism for rotating the insertion portion main body; a spiral-structured portion which converts rotary motion of the insertion portion main body due to the rotating mechanism into a propulsive force and which is separated in a diameter direction with respect to an outer surface of the insertion portion main body; and a spiral-outer-diameter change-imparting portion for changing a spiral-outer-diameter of the spiral-structured portion which is separated in the diameter direction with respect to the outer surface of the insertion portion main body.

The intrasubject insertion apparatus according to the fourth aspect of the present invention can obtain a stable propulsion force by ensuring an appropriate spiral shape of the spiral-structured portion.

The present invention provides an advantage in that it is possible to easily switch between propulsive motion along the direction of the longitudinal axis and changing of the propulsion direction with a simple structure, thereby performing guidance with high accuracy and stability.

Furthermore, since the intrasubject insertion apparatus according to the present invention obtains a stable propulsion force by ensuring an appropriate spiral shape of the spiral-structured portion, it is suitable for use in medical applications, such as examination, therapy, and treatment of a subject.

EXPLANATION OF REFERENCE SIGNS

Figure 1:
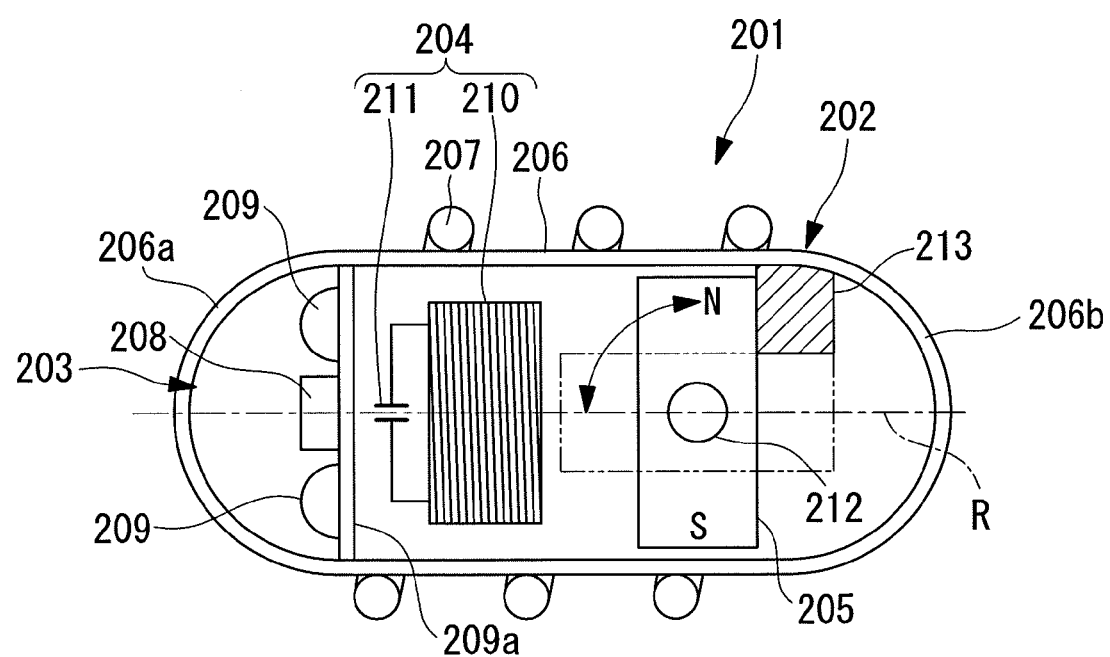
FIG. 1 is a longitudinal sectional view in schematic form depicting the structure of a capsule-type endoscope according to a first embodiment of the present invention.

A: subject
M: external magnetic field
R: longitudinal axis
201, 201', 201": capsule-type endoscope (capsule-type medical apparatus)
202: capsule
205, 205', 205": permanent magnet (magnet)
205a: indentation (engagement member)
207: spiral portion (spiral mechanism, propulsion mechanism)
212: rotation axis (securing portion)
213: stopper (securing portion)
214: click mechanism (engagement member: securing portion)
214a: ball (engagement member)
214a': shaft (engagement member)
215: clutch device (securing portion)
216: motor (magnetic-pole-direction switching device)
217: electromagnet
230: guidance system
250A: position-detecting apparatus (capsule-orientation detection apparatus)
271: three-axis Helmholtz-coil unit (magnetic-field generating apparatus)
273: magnetic-field control apparatus
1: capsule-type-medical-apparatus guidance system
3: capsule-type medical apparatus
4: capsule control apparatus
5: magnetic-field generating apparatus
6: AC power supply unit
8: magnet
22: imaging element
23: illuminating element
30: motor
41: front-end cover
42: capsule main body
43: capsule rear-end portion
44: spiral-structured portion
45: bearing

BEST MODE FOR CARRYING OUT THE INVENTION

First Embodiment

A capsule-type endoscope (capsule-type medical apparatus) 201 according to a first embodiment of the present invention will now be described with reference to FIG. 1, FIG. 2A, and FIG. 2B.

As shown in FIG. 1, the capsule-type endoscope 201 according to this embodiment includes a capsule 202; an imaging section 203 which is accommodated in the capsule 202 and captures an image of the internal surface of a passage in the body cavity of a subject; an induced-magnetic-field generating section 204; and a permanent magnet (magnet) 205.

The capsule 202 includes a cylindrical capsule main body 206 (hereinafter, referred to just as the main body) having a central axis aligned with a longitudinal axis R of the capsule-type endoscope 201; a transparent, hemispherical front-end portion 206a covering the front end of the main body 206; and a hemispherical rear-end portion 206b covering the rear end of the main body 206. The capsule 202 constitutes a capsule container that is sealed water tight.

In addition, a spiral portion (spiral mechanism, propulsion mechanism) 207 formed by spirally winding a wire, circular in sectional view, about the longitudinal axis R is provided on the outer circumferential surface of the main body 206 of the capsule 202. By doing so, when the main body 206 is rotated about the longitudinal axis R, the main body 206 moves in a straight line in a direction along the longitudinal axis R by a displacement determined according to the lead of the spiral portion 207.

The imaging section 203, opposing the front-end portion, includes an image sensor 208 for capturing an image of the internal surface of a passage in the body cavity of the subject and LEDs (Light Emitting Diodes) 209 for illuminating the internal surface of a passage in the body cavity. Reflected light from the internal surface of a passage in the body cavity illuminated by the operation of the LEDs 209 can be acquired as an image by the image sensor 208.

For the image sensor 208, for example, a CMOS (Complementary Metal Oxide Semiconductor) or a CCD can be used.

A plurality of the LEDs 209 is arranged at intervals in the circumferential direction about the longitudinal axis R on a support member 209a disposed adjacent to the front-end portion 206a.

The induced-magnetic-field generating section 204 is a resonant circuit including a magnetic induction coil 210 and a capacitor 211 connected to each other, and is made to resonate by supplying an external AC magnetic field with a predetermined frequency. A magnetic core (not shown in the figure) is disposed in the magnetic induction coil 210. For the magnetic core, a magnetic material is suitable, as well as a ferrite. For example, iron, nickel, permalloy, or cobalt can be used. The magnetic core produces an AC magnetic field with large amplitude used for position detection.

Figure 2A:
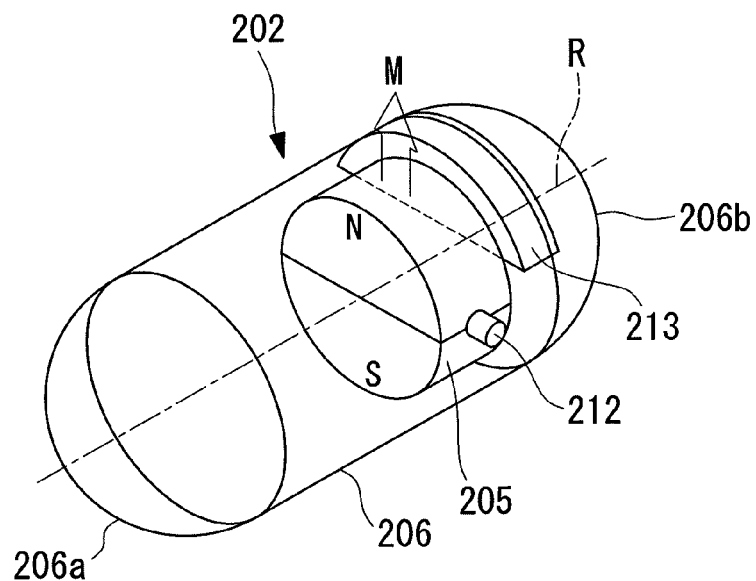
FIG. 2A is a perspective view of the capsule-type endoscope of FIG. 1, in an advancing mode, for illustrating the switching of a guidance mode.
Figure 2B:
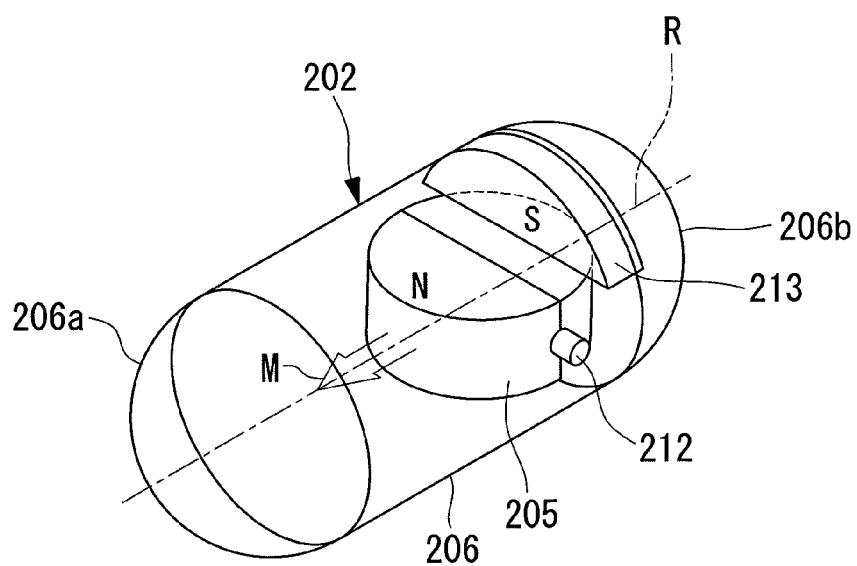
FIG. 2B is a perspective view of the capsule-type endoscope of FIG. 1, in an orientation-changing mode, for illustrating the switching of a guidance mode.

As shown in FIG. 1, FIG. 2A, and FIG. 2B, the permanent magnet 205 is shaped like a column slightly smaller than the inner diameter of the main body 206 of the capsule 202. One semicylindrical half thereof is magnetized as the north pole, and the other semicylindrical half thereof is magnetized as the south pole. Furthermore, the permanent magnet 205 is mounted on an inner surface of the main body 206 with a rotation axis 212 passing in the diametral direction through the boundary between the north pole and the south pole. The permanent magnet 205 is rotatably mounted on the rotation axis 212.

The permanent magnet 205 and the rotation axis 212 are fitted to each other so as to produce a predetermined frictional force therebetween.

A stopper 213 is disposed adjacent to the permanent magnet 205. The stopper 213 is disposed so as to abut against a side surface of the permanent magnet 205 to prevent the permanent magnet 205 from rotating any further when the magnetic poles of the permanent magnet 205 are aligned in the direction of the longitudinal axis R (as shown in FIG. 2B) and in a direction orthogonal to the longitudinal axis R (as shown in FIG. 2A) as a result of the permanent magnet 205 rotating about the rotation axis 212.

Next, a guidance system 230 and a guidance method of a capsule-type endoscope according to one embodiment of the present invention will be described with reference to FIG. 3 to FIG. 6.

Figure 3:
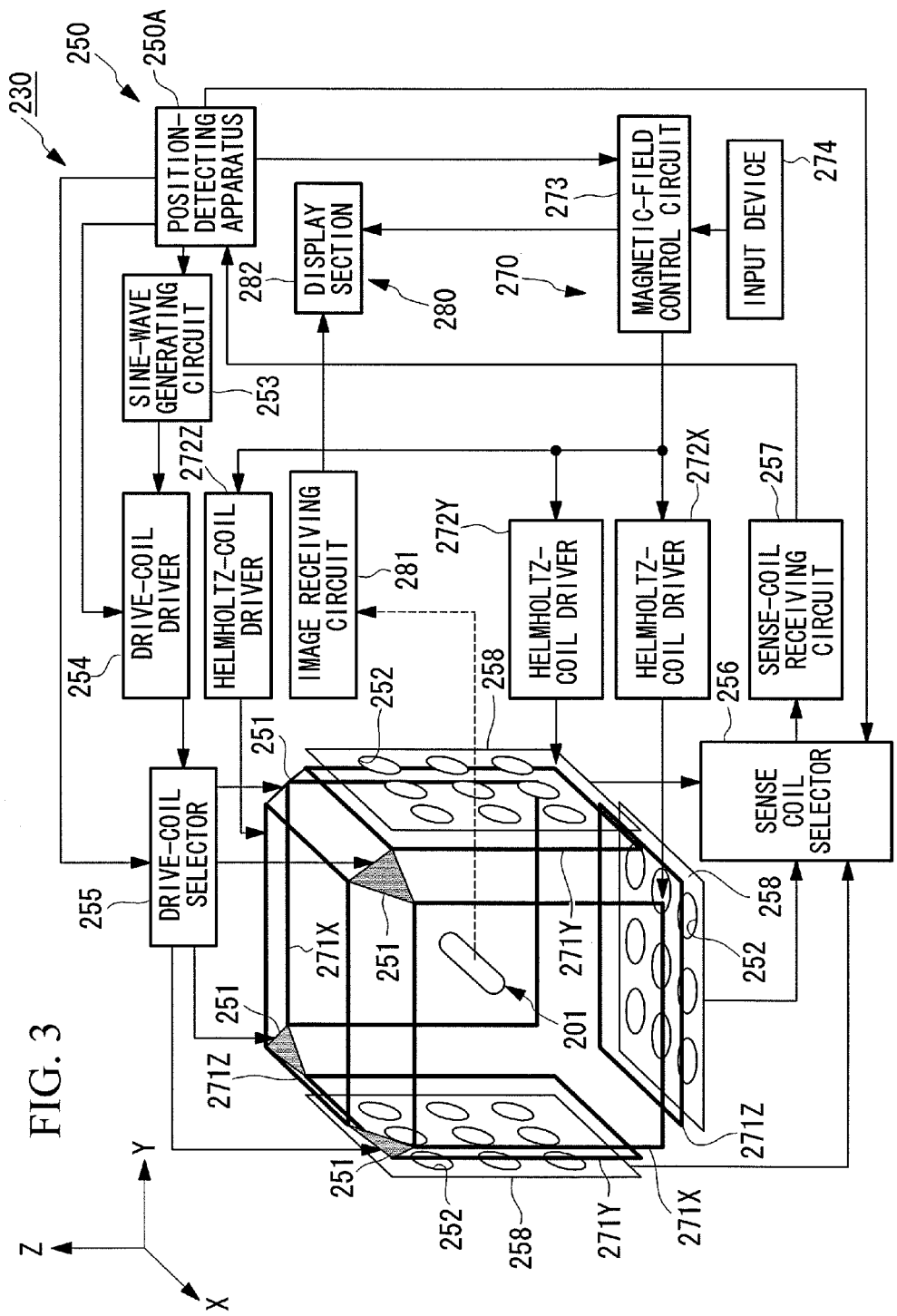
FIG. 3 is a schematic diagram depicting a guidance system of a capsule-type endoscope according to the first embodiment of the present invention.

As shown in FIG. 3, the guidance system 230 according to this embodiment includes the above-described capsule-type endoscope 201, which is introduced into the body cavity of a subject, per oral or per anus, to optically image the internal surface of a passage in the body cavity and wirelessly transmit an image signal; a position detection system 250 for detecting the position of the capsule-type endoscope 201; a magnetic guidance apparatus 270 for guiding the capsule-type endoscope 201 based on the detected position of the capsule-type endoscope 201 and operator commands; and an image display apparatus 280 for displaying an image signal transmitted from the capsule-type endoscope 201.

As shown in FIG. 3, the magnetic guidance apparatus 270 includes a three-axis Helmholtz-coil unit (magnetic-field generating apparatus) 271 that produces a parallel external magnetic field (substantially uniform magnetic field) M for driving the capsule-type endoscope 201; a Helmholtz-coil driver 272 that controls the gain of electric currents supplied to the three-axis Helmholtz-coil unit 271; a magnetic-field control circuit 273 that controls the direction of the parallel magnetic field for driving the capsule-type endoscope 201; and an input device 274 for outputting to the magnetic-field control circuit 273 the direction of movement of the capsule-type endoscope 201 that has been input by the operator. In addition, a propulsion mode or an orientation-changing mode can be selected as the guidance mode of the capsule-type endoscope 201 in the input device 274.

Figure 4:
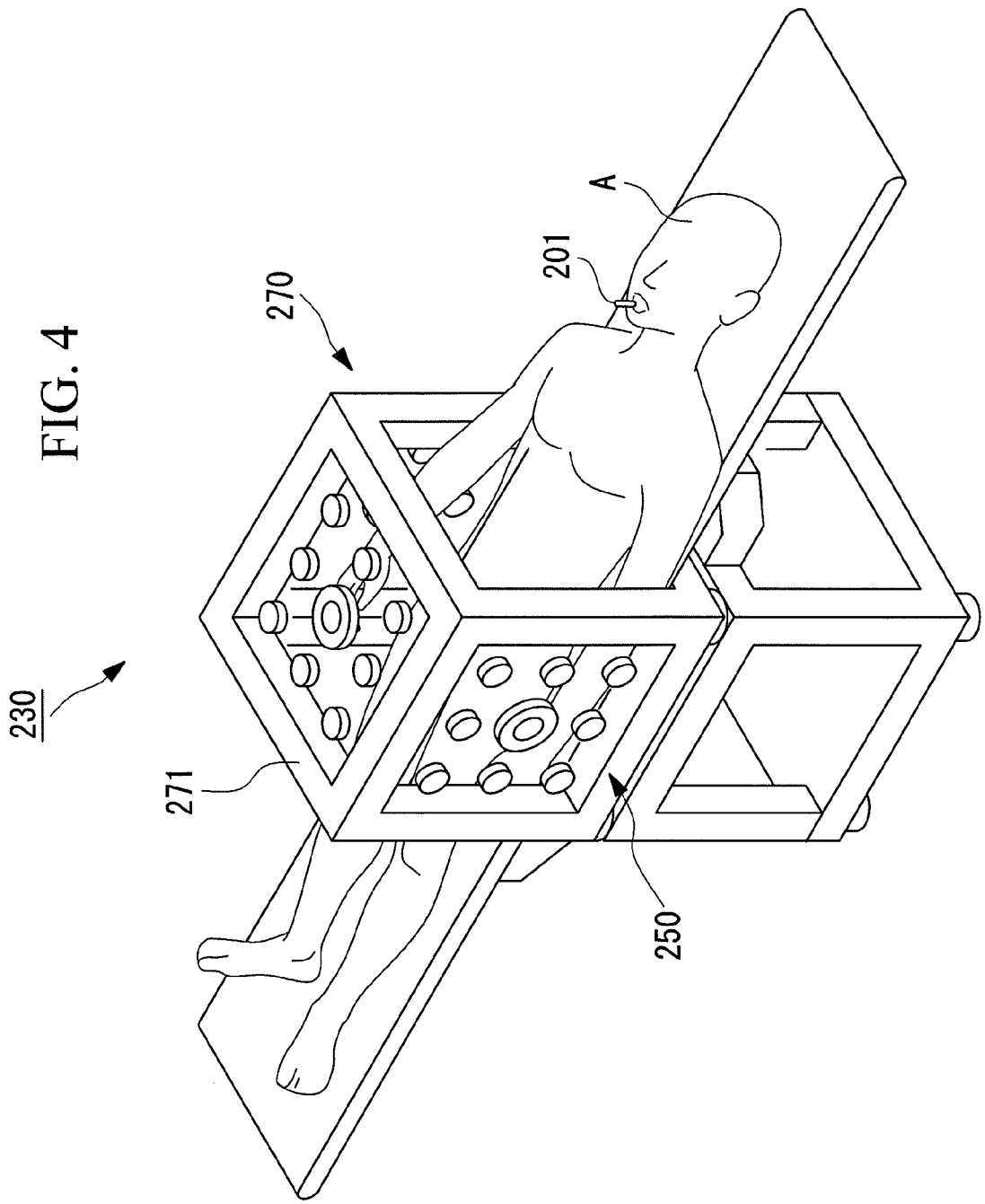
FIG. 4 is perspective view of the guidance system of FIG. 3.
Figure 5:
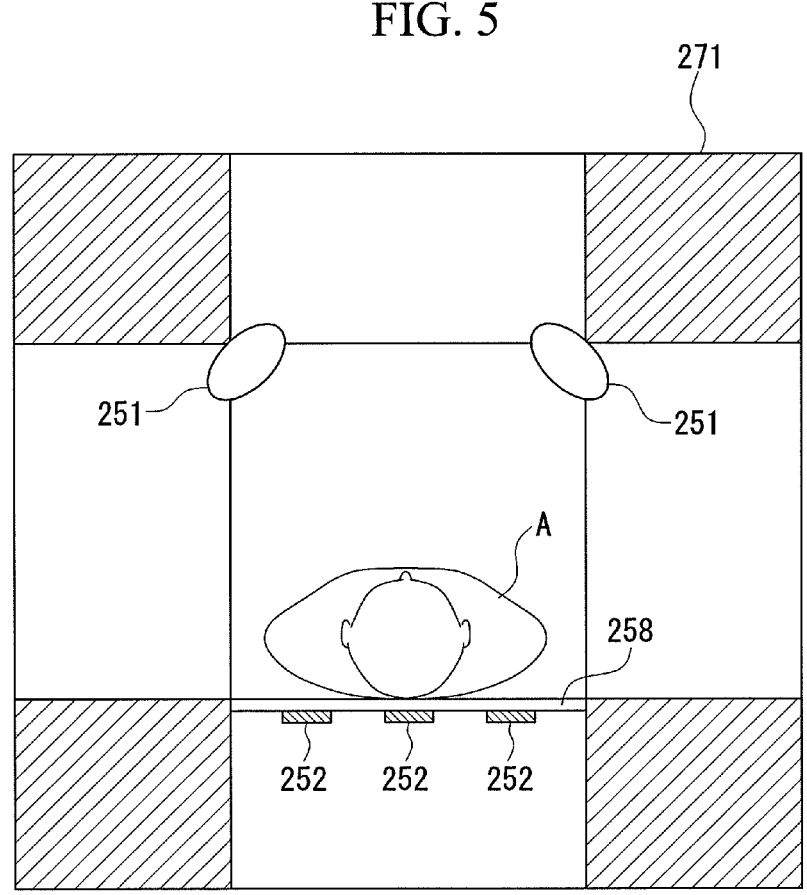
FIG. 5 is a vertical sectional view of the guidance system of FIG. 3.

As shown in FIG. 3 to FIG. 5, the three-axis Helmholtz-coil unit 271 is formed in a substantially rectangular shape. Furthermore, the three-axis Helmholtz-coil unit 271 includes three pairs of mutually opposing Helmholtz coils 271X, 271Y, and 271Z, and each pair of Helmholtz coils 271X, 271Y, and 271Z is disposed so as to be substantially orthogonal to the X, Y, and Z axes in FIG. 3. The Helmholtz coils disposed substantially orthogonally to the X, Y, and Z axes are denoted as the Helmholtz coils 271X, 271Y, and 271Z, respectively.

The Helmholtz coils 271X, 271Y, and 271Z are disposed so as to form a rectangular space therein. As shown in FIG. 3, the rectangular space serves as a working space of the capsule-type endoscope 201 and, as shown in FIG. 4 and FIG. 5, is the space in which a subject A is placed.

Furthermore, although the coils are denoted as the Helmholtz coils 271X, 271Y, and 271Z in this embodiment, the coils may be rectangular coils as shown in FIG. 3 to FIG. 5, and it is not necessary for the coils to strictly satisfy Helmholtz-coil conditions.

The Helmholtz-coil driver 272 includes Helmholtz-coil drivers 272X, 272Y, and 272Z that control the Helmholtz coils 271X, 271Y, and 271Z, respectively.

Data indicating the direction in which the capsule-type endoscope 201 is currently pointing (direction of the longitudinal axis R of the capsule-type endoscope 201) is supplied to the magnetic-field control circuit 273 from a position-detecting apparatus 250A of the position detection system 250. Furthermore, data indicating the guidance mode and direction-of-movement instructions for the capsule-type endoscope 201 that have been input by the operator using the input device 274 are also supplied to the magnetic-field control circuit 273.

When the magnetic-field control circuit 273 receives data about the guidance mode, the magnetic-field control circuit 273 momentarily produces an external magnetic field M for switching the magnetic-pole direction of a permanent magnet 205 based on the direction data of the capsule-type endoscope 201. More specifically, when guidance mode data indicating the advancing mode is input, the magnetic-field control circuit 273 momentarily causes the Helmholtz coil unit 271 to produce the external magnetic field M in a direction orthogonal to the longitudinal axis R of the capsule 202, as shown in FIG. 2A, to reorient the permanent magnet 205 in a direction orthogonal to the capsule longitudinal axis R. Furthermore, when guidance mode data indicating the orientation-changing mode is input, the magnetic-field control circuit 273 momentarily causes the Helmholtz coil unit 271 to produce an external magnetic field M in a direction along the longitudinal axis R of the capsule 202, as shown in FIG. 2B, to reorient the permanent magnet 205 in a direction along the longitudinal axis R of the capsule 202.

From the magnetic-field control circuit 273, a signal for controlling the Helmholtz-coil drivers 272X, 272Y, and 272Z is output according to the guidance mode, and rotation phase data of the capsule-type endoscope 201 is output to the image display apparatus 280.

As the input device 274, an input device for specifying the direction of movement of the capsule-type endoscope 201 by operating a joystick is used.

As mentioned above, the input device 274 may be a joystick-type device. Alternatively, another type of input device may be used, such as an input device that specifies the direction of movement by pushing direction-of-movement buttons.

As shown in FIG. 3, the position detection system 250 includes drive coils 251 that produce an induced magnetic field in the magnetic induction coil 210 in the capsule-type endoscope 201; sense coils 252 that detect the induced magnetic field generated in the magnetic induction coil 210; and the position-detecting apparatus 250A that computes the position of the capsule-type endoscope 201 based on the induced magnetic field detected by the sense coils 252 and that controls the AC magnetic field formed by the drive coils 251.

Between the position-detecting apparatus 250A and the drive coils 251, there are provided a sine-wave generating circuit 253 that produces an AC current based on the output from the position-detecting apparatus 250A; a drive-coil driver 254 that amplifies the AC current input from the sine-wave generating circuit 253 based on the output from the position-detecting apparatus 250A; and a drive-coil selector 255 that supplies the AC current to drive coils 251 selected based on the output from the position-detecting apparatus 250A.

Between the sense coils 252 and the position-detecting apparatus 250A, there are provided a sense coil selector 256 that selects an AC current including, for example, position information of the capsule-type endoscope 201 from the sense coils 252 based on the output from the position-detecting apparatus 250A; and a sense-coil receiving circuit 257 that extracts an amplitude value from the above-described AC current that has passed through the sense coil selector 256 and outputs it to the position-detecting apparatus 250A.

As shown in FIG. 3, the image display apparatus 280 includes an image receiving circuit 281 that receives images transmitted from the capsule-type endoscope 201 and a display section (display means, image control means) 282 that displays images based on received image signals and signals from the magnetic-field control circuit 273.

The operation of the capsule-type endoscope 201 according to this embodiment, with the above-described structure, and the guidance system 230 therefor will be described below.

As shown in FIG. 4, in order to examine the interior of the body cavity of the subject A using the capsule-type endoscope 201 and the guidance system 230 therefor according to this embodiment, the capsule-type endoscope 201 is inserted, per oral or per anus, into the body cavity of the subject A who is lying down inside the position detection system 250 and the magnetic guidance apparatus 270. The position of the capsule-type endoscope 201 is detected by the position detection system 250, and the capsule-type endoscope 201 is guided to the vicinity of an affected area in a passage of the body cavity of the subject A by the magnetic guidance apparatus 270. The capsule-type endoscope 201 images the internal surface of the passage in the body cavity while being guided to the affected area and in the vicinity of the affected area. Then, data for the imaged internal surface of the passage in the body cavity and data for the vicinity of the affected area are transmitted to the image display apparatus 280. The image display apparatus 280 displays the transmitted images on the display section 282.

As shown in FIG. 3, in the position detection system 250, first the sine-wave generating circuit 253 generates an AC current based on the output from the position-detecting apparatus 250A, and the AC current is output to the drive-coil driver 254. The frequency of the generated AC current is in a frequency range from a few kHz to 100 kHz.

The AC current is amplified in the drive-coil driver 254 based on a command from the position-detecting apparatus 250A and is output to the drive-coil selector 255. The amplified AC current is supplied to the drive coils 251 that are selected in the drive-coil selector 255 by the position-detecting apparatus 250A. Then, the AC current supplied to the drive coils 251 produces an AC magnetic field in the working space of the capsule-type endoscope 201.

In the magnetic induction coil 210 of the capsule-type endoscope 201 disposed in the produced AC magnetic field, an induced electromotive force is generated by the AC magnetic field, thereby causing an induction current to flow. When the induction current flows in the magnetic induction coil 210, induced magnetism occurs, thereby producing an AC magnetic field.

Furthermore, since the magnetic induction coil 210 constitutes a resonant circuit together with the capacitor 211, when the period of the AC magnetic field coincides with the resonant frequency of the resonant circuit, a larger amount of induction current flows in the resonant circuit (the magnetic induction coil 210), and accordingly, the produced AC magnetic field becomes intense. In addition, since a core member composed of dielectric ferrite is disposed in the center of the magnetic induction coil 210, the magnetic flux is more easily concentrated in the core member, which causes the produced AC magnetic field to be even more intense.

The induced AC magnetic field generates an induced electromotive force in the sense coils 252, and thereby an AC voltage (magnetic information) including, for example, position information of the capsule-type endoscope 201 is generated in the sense coils 252. This AC voltage is input to the sense-coil receiving circuit 257 via the sense coil selector 256, and the amplitude value of the AC voltage is extracted.

The sense-coil receiving circuit 257 stores an amplitude value corresponding to one period during which a sine-wave signal generated in the sine-wave generating circuit 253 is swept close to the resonance frequency of the resonance circuit, and outputs the amplitude value for one period at a time to the position-detecting apparatus 250A.

Figure 6:
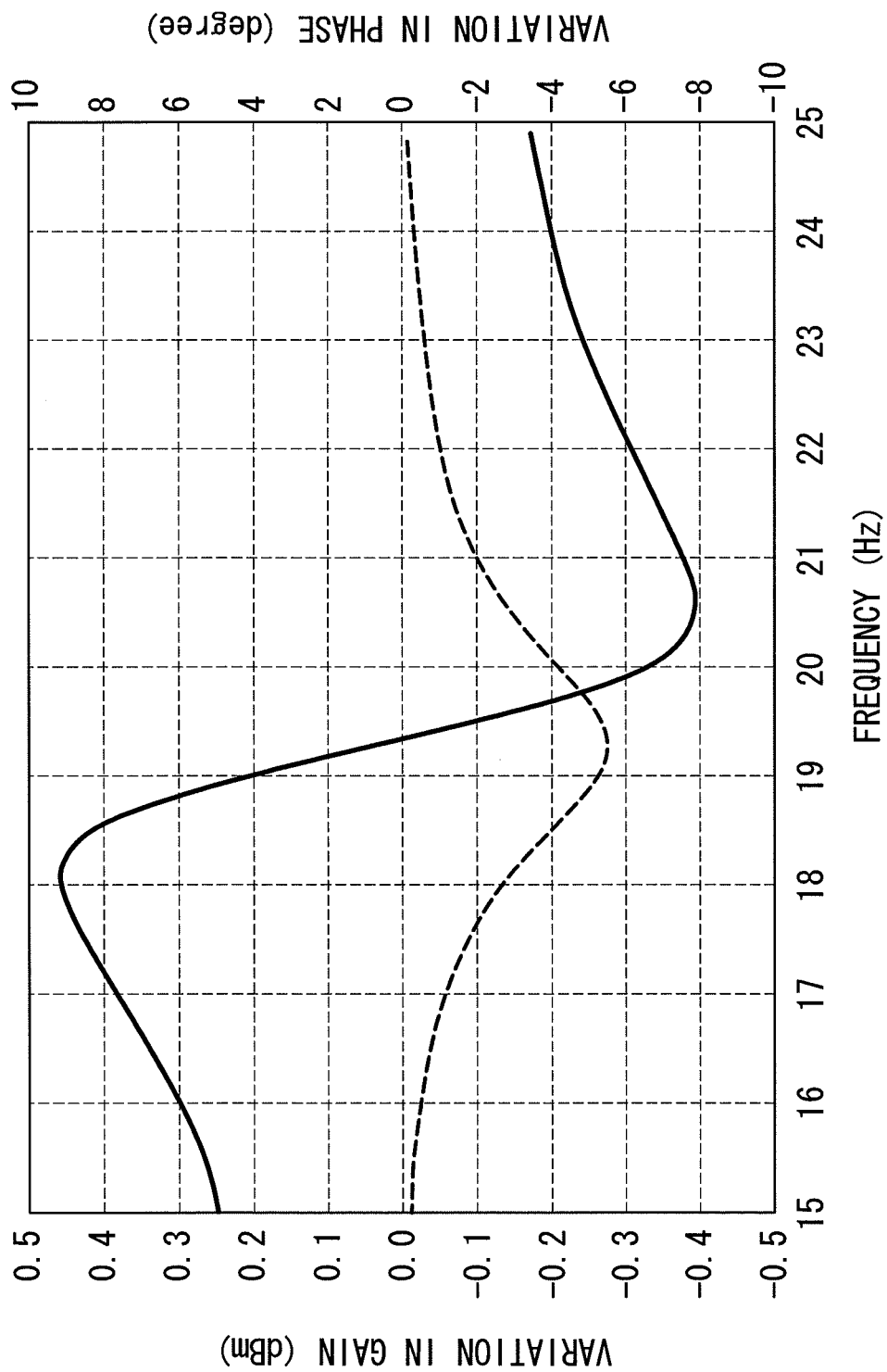
FIG. 6 is a graph depicting frequency characteristics of a resonant circuit of the capsule-type endoscope of FIG. 1.

As shown in FIG. 6, the above-described amplitude value of the AC voltage changes greatly depending on the relationship between the AC magnetic field formed by the drive coils 251 and the resonant frequency of the resonant circuit 204. In FIG. 6, the horizontal axis represents the frequency of the AC magnetic field, and the vertical axis represents variations in gain (dBm) and phase (degree) of the AC voltage carried in the resonant circuit 204. The variation in gain, indicated by the solid line, exhibits a maximum value at a frequency smaller than the resonance frequency, becomes zero at the resonance frequency, and exhibits a minimum value at a frequency higher than the resonance frequency. Also, it is shown that the variation in phase, indicated by the broken line, drops most at the resonance frequency.

Depending on the measurement conditions, there may be cases where the gain exhibits a minimum value at a frequency lower than the resonance frequency and exhibits a maximum value at a frequency higher than the resonance frequency, and where the phase reaches a peak at the resonance frequency.

The position-detecting apparatus 250A assumes the amplitude difference between the maximum value and the minimum value of the amplitude value in the vicinity of the resonance frequency to be the output from the sense coils 252. Then, the position-detecting apparatus 250A calculates the position and so forth of the capsule-type endoscope 201 by solving simultaneous equations involving the position, orientation, and magnetic field strength of the capsule-type endoscope 201 based on the amplitude difference obtained from the plurality of sense coils 252.

Thus, by assuming the output of the sense coils 252 to be the amplitude difference in this way, it is possible to cancel variations in amplitude that originate from variations in the magnetic field intensity due to environmental conditions (e.g., temperature), and it is therefore possible to obtain the position of the capsule-type endoscope 201 with a reliable degree of accuracy without being affected by environmental conditions.

The position-detecting apparatus 250A informs the drive-coil driver 254 of the amplification factor of the AC current supplied to the drive coils 251 based on the position of the capsule-type endoscope 201 obtained by calculation. This amplification factor is set so that the induced magnetic field produced by the magnetic induction coil 210 can be detected by the sense coils 252.

Also, the position-detecting apparatus 250A selects drive coils 251 for producing magnetic fields and instructs the drive-coil selector 255 to supply the AC current to the selected drive coils 251.

As shown in FIG. 3, in the magnetic guidance apparatus 270, first the operator selects the guidance mode of the capsule-type endoscope 201 for the magnetic-field control circuit 273 using the input device 274. If the advancing mode is selected as the guidance mode, a relatively large external magnetic field M is formed momentarily in a direction orthogonal to the direction of the longitudinal axis R of the capsule 202 detected by the position detection system 250. By doing so, a torque exceeding the static frictional force between the permanent magnet 205 and the rotation axis 212 is produced in the permanent magnet 205, which hence rotates about the rotation axis 212 to align its magnetic poles in the direction orthogonal to the longitudinal axis R, as shown in FIG. 2A. The permanent magnet 205 abuts against the stopper 213 and stops when its magnetic poles are aligned in the direction orthogonal to the longitudinal axis R and is held still due to a static frictional force between itself and the rotation axis 212.

When the operator specifies a direction of movement using the input device 274 in this state, the direction and rotation direction of the external magnetic field M to be applied to the capsule-type endoscope 201 are determined by the operation of the magnetic-field control circuit 273 based on the specified direction of movement and the orientation of the capsule-type endoscope 201 (direction of the longitudinal axis R) input from the position-detecting apparatus 250A.

Then, the intensity of a magnetic field to be generated by each of the Helmholtz coils 271X, 271Y, and 271Z required to achieve the above-described direction of the external magnetic field M is calculated, and current values required to produce these external magnetic fields M are calculated.

Data on currents supplied to the Helmholtz coils 271X, 271Y, and 271Z is output to the corresponding Helmholtz-coil drivers 272X, 272Y, and 272Z, and the Helmholtz-coil drivers 272X, 272Y, and 272Z amplify and control the currents based on the input data and supply the currents to the corresponding Helmholtz coils 271X, 271Y, and 271Z.

The Helmholtz coils 271X, 271Y, and 271Z to which the currents are supplied produce magnetic fields according to the respective current values, and by combining these magnetic fields, a parallel external magnetic field M having the magnetic-field direction determined by the magnetic-field control circuit 273 is produced.

Also, by controlling the rotation period of the above-described external magnetic field M to be from about 0 Hz to a few Hz and controlling the rotation direction of the external magnetic field M, the rotation direction about the longitudinal axis R of the capsule-type endoscope 201 is controlled. As a result, the permanent magnet 205 is oriented in a direction along the rotating external magnetic field M, and the capsule 202 in which the permanent magnet 205 is installed is rotated about the longitudinal axis R. Then, the rotational motion about the longitudinal axis R of the capsule 202 is converted into translatory movement along the longitudinal axis R through the operation of the spiral portion 207 provided on the outer circumferential surface of the capsule 202, and the capsule-type endoscope 201 is propelled in a direction specified via the input device 274 at a speed determined by the rotational speed of the external magnetic field M and the lead of the spiral portion 207.

If the external magnetic field M formed when the advancing mode is selected as the guidance mode has a direction along the rotation axis 212 or is oriented in a direction opposite to the radial direction, the permanent magnet 205 is not rotated. To avoid this, the phase about the longitudinal axis R of the capsule 202 should be obtained by, for example, processing an image acquired by the image sensor 208 and, based on this phase, the direction in which the external magnetic field M is applied can be determined.

On the other hand, if the orientation-changing mode is selected as the guidance mode, a relatively large external magnetic field M is formed momentarily in a direction along the direction of the longitudinal axis R of the capsule 202 detected by the position-detecting apparatus 250A. By doing so, a torque exceeding the static frictional force between the permanent magnet 205 and the rotation axis 212 is produced in the permanent magnet 205, which hence rotates about the rotation axis 212 to align its magnetic poles in the direction along the longitudinal axis R, as shown in FIG. 2B. The permanent magnet 205 abuts against the stopper 213 and stops when its magnetic poles are aligned in the direction along the longitudinal axis R and is held still due to a static frictional force between itself and the rotation axis 212.

Thereafter, the capsule 202 is subjected to a rotary force to reorient itself by gradually changing the angle of the external magnetic field M formed in the direction along the longitudinal axis R of the capsule 202 based on the input from the input device 274.

Switching the guidance mode from the advancing mode to the orientation-changing mode can be performed easily by changing the magnetic-pole direction of the permanent magnet 205. This can be done merely by applying the external magnetic field M in the direction along the longitudinal axis R of the capsule 202, irrespective of the orientation of the permanent magnet 205.

In the capsule-type endoscope 201, the image sensor 208, which is mounted therein, acquires an image of the internal surface of a passage in the body cavity of the subject A illuminated with the LEDs 209, and the acquired image is transmitted to the image display apparatus 280.

In the image display apparatus 280, the image receiving circuit 281 receives image information transmitted from the capsule-type endoscope 201, and the received image information is displayed on the display section 282.

Furthermore, if the guidance mode is the advancing mode, the display section 282, before displaying the above-described image signal, performs rotation processing on the image signal in the opposite direction to the rotation direction of the capsule-type endoscope 201, based on data about the rotation phase of the capsule-type endoscope 201 input from the magnetic-field control circuit 273. By doing so, it is possible to display on the display section 282 an image that is always fixed at a predetermined rotational phase, in other words, an image in which the capsule-type endoscope 201 appears to travel along the longitudinal axis R without rotating about the longitudinal axis R, regardless of the rotational phase of the capsule-type endoscope 201.

Accordingly, when the operator is to guide the capsule-type endoscope 201 in the advancing mode while observing the image displayed on the display section 282, the image is easy to observe and, therefore, the capsule-type endoscope 201 can easily be guided to a predetermined location in the case where the image is presented as an image fixed at a predetermined rotational phase, as described above, compared to the case where the image is displayed as an image that rotates along with the rotation of the capsule-type endoscope 201.

As described above, according to the capsule-type endoscope 201 and the guidance system 230 therefor of this embodiment, the magnetic-pole direction of the built-in permanent magnet 205 can be changed to enter the advancing mode or the orientation-changing mode merely by applying the external magnetic field M of a particular direction to the capsule-type endoscope 201. Therefore, in the advancing mode, the capsule-type endoscope 201 can be advanced with high accuracy in the direction of the longitudinal axis R, whereas, in the orientation-changing mode, the capsule-type endoscope 201 can be oriented with high stability in a desired direction. As a result, the capsule-type endoscope 201 can be guided in the body of the subject A with high accuracy and stability to perform desired examination.

Figure 7:
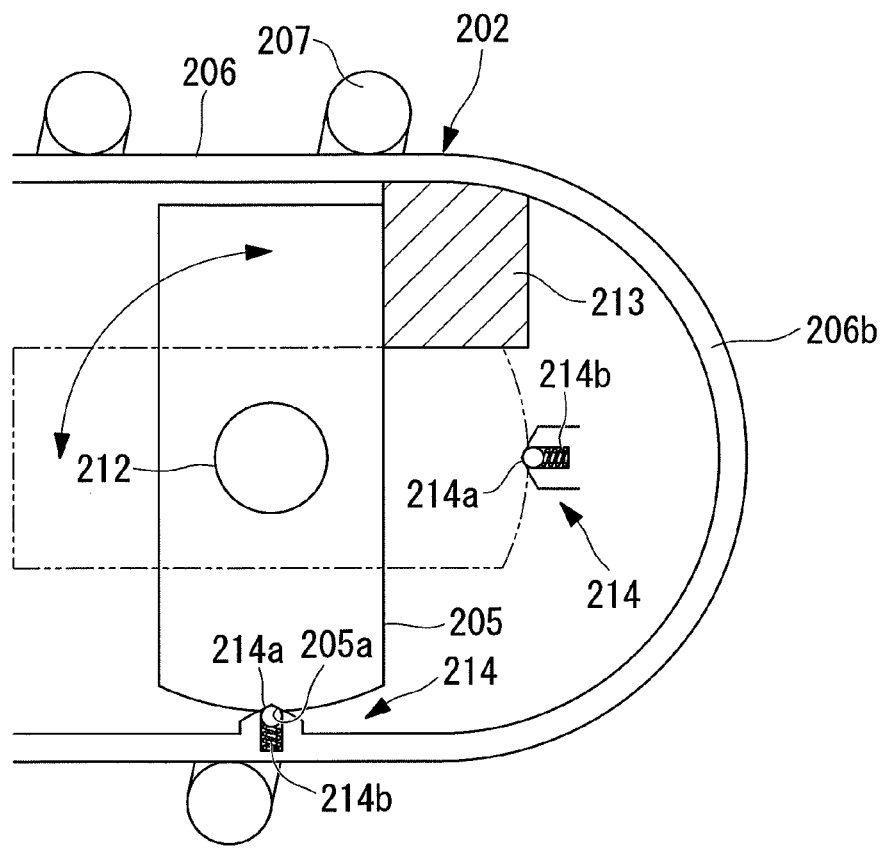
FIG. 7 is a longitudinal sectional view partially depicting a first modification of the capsule-type endoscope of FIG. 1.
Figure 8:
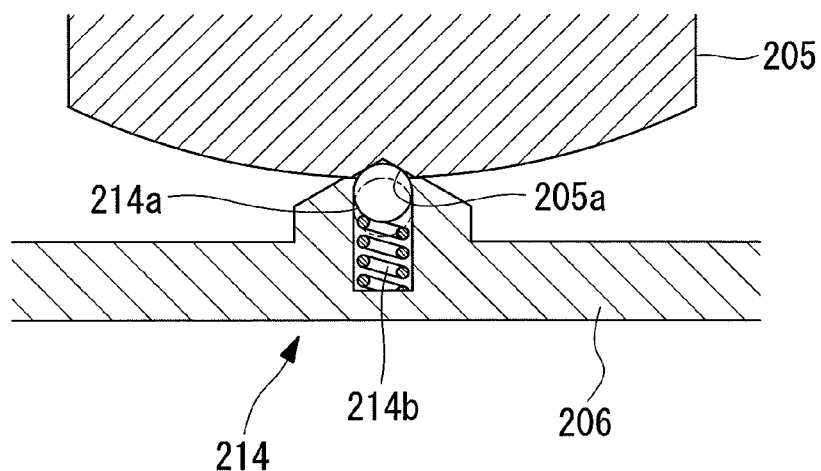
FIG. 8 is a magnified cross-sectional view of a click mechanism of the capsule-type endoscope shown in FIG. 7.

In this embodiment, the securing portion of the permanent magnet 205 was achieved by the static frictional force between the permanent magnet 205 itself and the rotation axis 212 that rotatably supports the permanent magnet 205. Alternatively, as shown in FIG. 7 and FIG. 8, it is possible to form an indentation 205a in the permanent magnet 205 and to provide a click mechanism 214 composed of a spring 214b and a ball 214a that is brought into engagement with the indentation 205a in the permanent magnet 205 at two locations corresponding to the advancing mode and the orientation-changing mode, respectively. By doing so, each guidance mode can be retained more reliably.

Figure 9A:
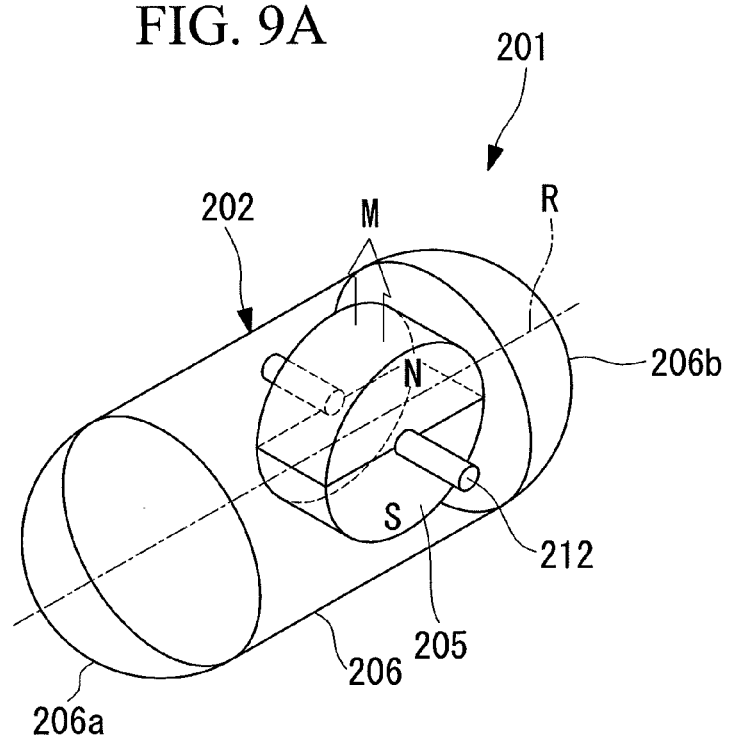
FIG. 9A is a perspective view of a second modification of the capsule-type endoscope of FIG. 1.
Figure 9B:
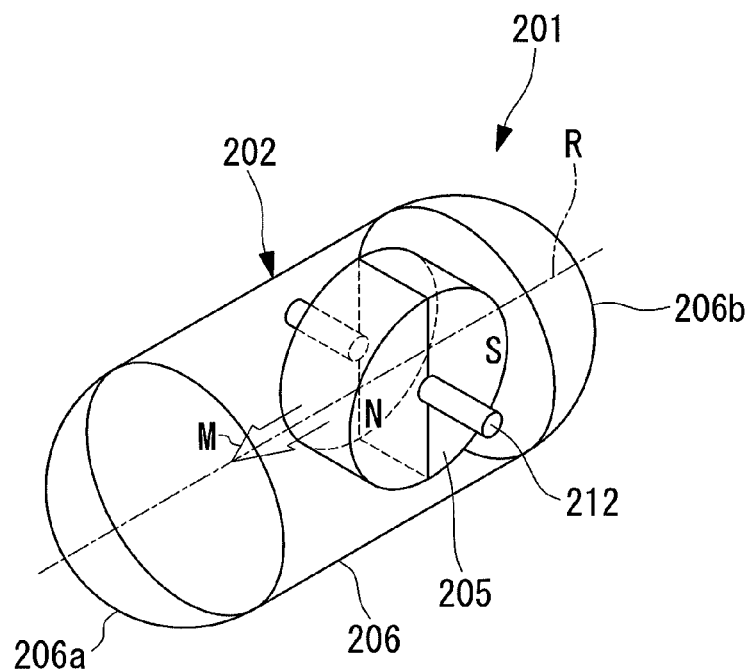
FIG. 9B is a perspective view of the second modification of the capsule-type endoscope of FIG. 1.
Figure 10:
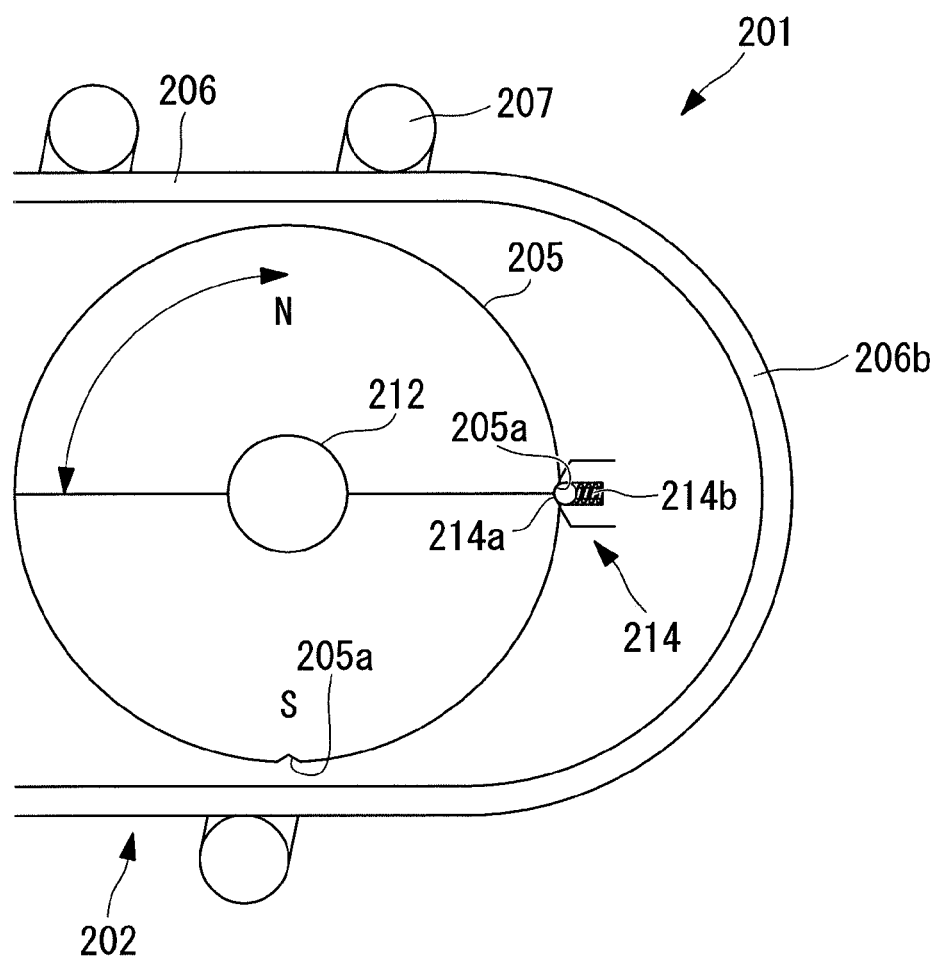
FIG. 10 is a longitudinal sectional view partially depicting the capsule-type endoscope of FIG. 9A and FIG. 9B.

Alternatively, as shown in FIG. 9A, FIG. 9B and FIG. 10, a columnar member whose center is aligned with the rotation axis 212 may be employed as the permanent magnet 205. By doing so, it is sufficient to provide the click mechanism 214 composed of the ball 214a and the spring 214b only at a single location, though the indentation 205a is provided at two locations separated by 90° from each other along the circumferential surface of the permanent magnet 205.

Figure 11:
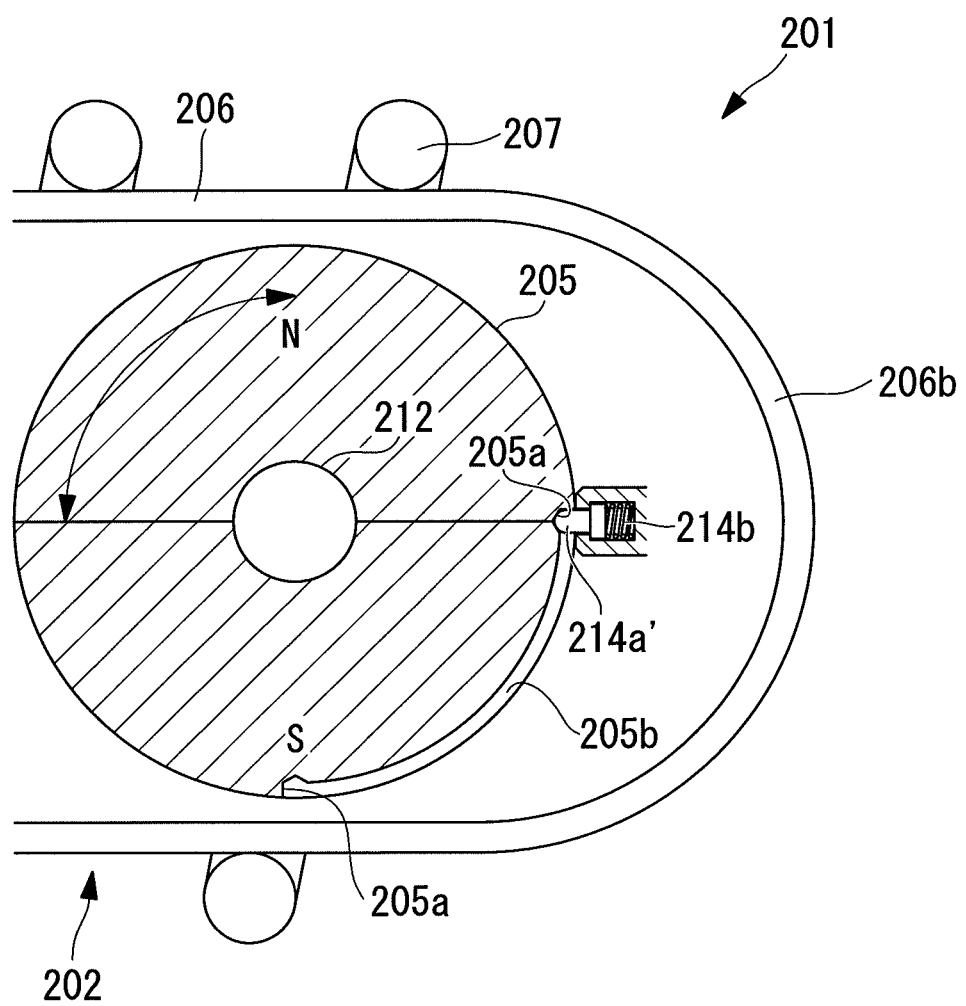
FIG. 11 is a longitudinal sectional view of a modification of the capsule-type endoscope of FIG. 9A and FIG. 9B.

Furthermore, as shown in FIG. 11, the two indentations 205a may be formed more deeply, a groove 205b that links the indentations 205a in the circumferential direction may be provided, and a shaft 214a' may be provided instead of the ball 214a. By doing so, when the tip of the shaft 214a' is fitted in the indentation 205a, the shaft 214a' abuts against the inner wall of the groove 205b, thus preventing further rotation of the permanent magnet 205. The working area of the permanent magnet 205 can be limited to within a range of 90° in this manner.

Although the columnar permanent magnet 205 is employed, a spherical permanent magnet (not shown in the figure) may be employed instead. By doing so, the volume of the permanent magnet can be increased so that the permanent magnet can produce a larger magnetic force. As a result, the intensity of the external magnetic field M for driving the capsule-type endoscope 201 can be reduced, which helps reduce the size of the magnetic-field generating apparatus 271 disposed outside the subject's body. In addition, although the ball 214a or the shaft 214a' which is urged by the coil spring 214b is fitted in the indentation 205a formed on the permanent magnet 205, a protrusion (not shown in the figure) provided on a leaf spring (not shown in the figure) may be fitted in the indentation 205a instead.

Figure 12:
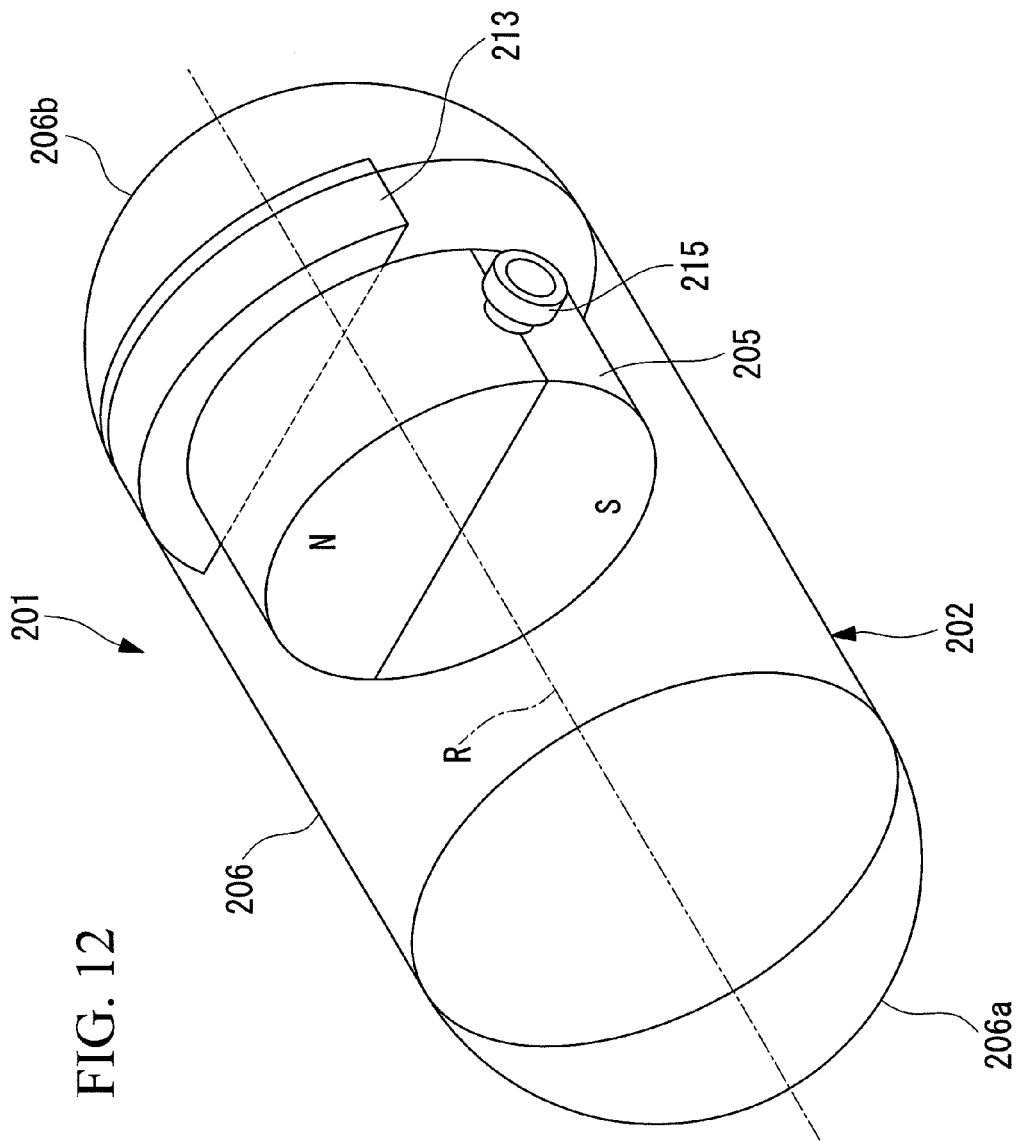
FIG. 12 is a perspective view of a third modification of the capsule-type endoscope of FIG. 1.

Alternatively, a clutch mechanism 215 may be provided between the capsule 202 and the permanent magnet 205, as shown in FIG. 12. The clutch mechanism 215 is normally turned off to prevent the permanent magnet 205 from rotating. At the time of switching the guidance mode, the clutch mechanism 215 is turned on to allow the permanent magnet 205 to rotate freely. By doing so, securing the permanent magnet 205 to the capsule 202 and releasing the permanent magnet 205 from the capsule 202 can be carried out more reliably, which is advantageous in switching the guidance mode smoothly. In addition, normally setting the clutch mechanism 215 to off saves the battery.

In addition, the permanent magnet 205 may be allowed to freely rotate about the rotation axis 212, and furthermore, the stopper 213, in FIG. 1, FIG. 2A, and FIG. 2B, that abuts against the permanent magnet 205 as the securing portion of the permanent magnet 205 may be formed of a magnetic material. By doing so, when the permanent magnet 205 rotates and abuts against the stopper 213 when switching the guidance mode, the permanent magnet 205 comes into close contact with the stopper 213, which is made of a magnetic material, and is thus securely held in each state. On the other hand, when the guidance mode is to be switched to enter the other mode, the permanent magnet 205 can be rotated by applying an external magnetic field M that can produce a torque overwhelming the magnetic attraction force between the permanent magnet 205 and the stopper 213.

Figure 13:
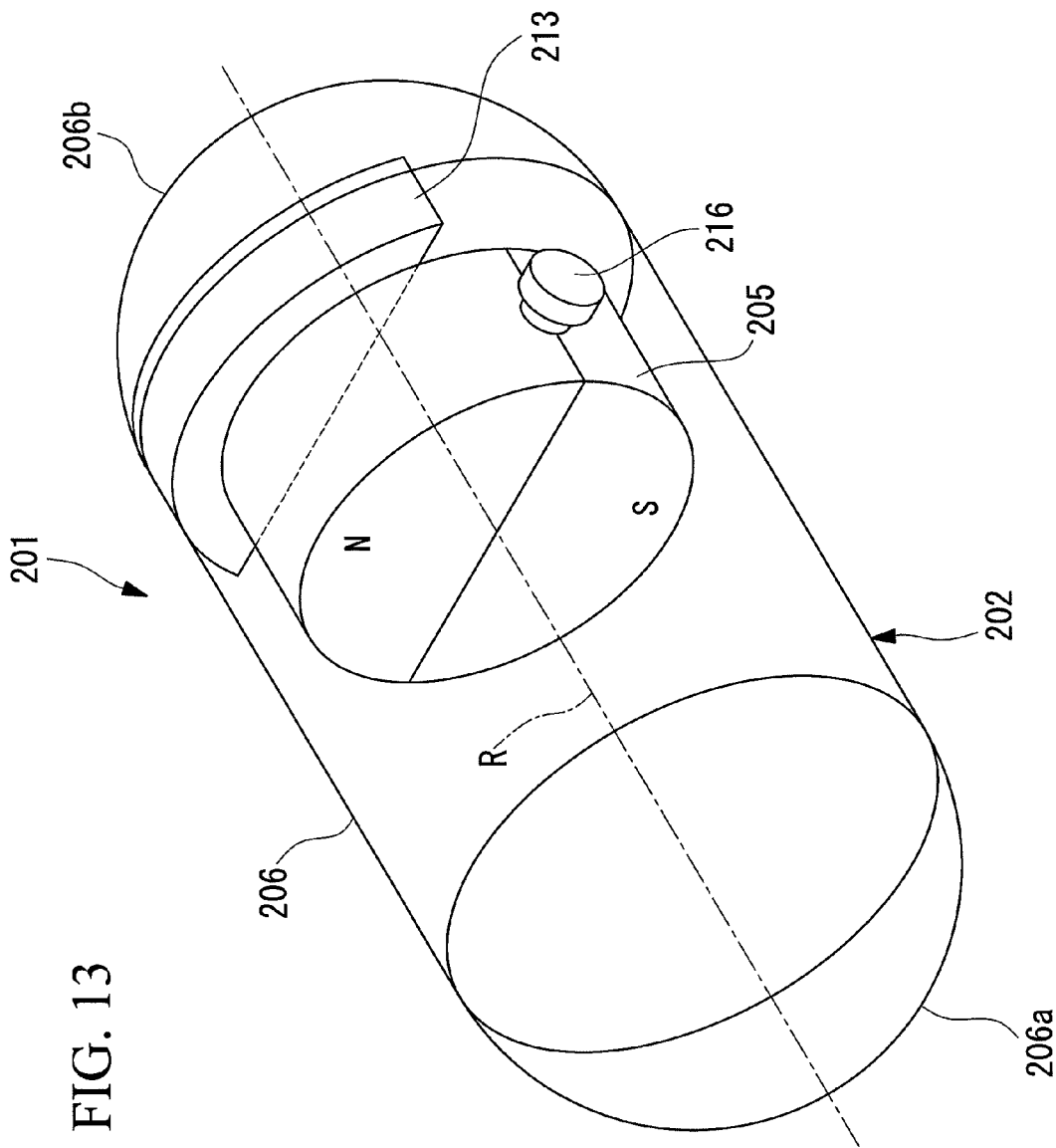
FIG. 13 is a perspective view of a fourth modification of the capsule-type endoscope of FIG. 1.

Furthermore, although the magnetic-pole direction of the permanent magnet 205 is changed through the operation of the external magnetic field M in the capsule-type endoscope 201 according to this embodiment, an actuator for changing the magnetic-pole direction of the permanent magnet 205 may be provided in the capsule 202 instead. For this actuator, for example, a motor 216 that operates in response to an external command signal may be provided on the rotation axis 212 of the permanent magnet 205, as shown in FIG. 13, so that the permanent magnet 205 is rotated through the operation of the motor 216 to switch the magnetic-pole direction.

Figure 14A:
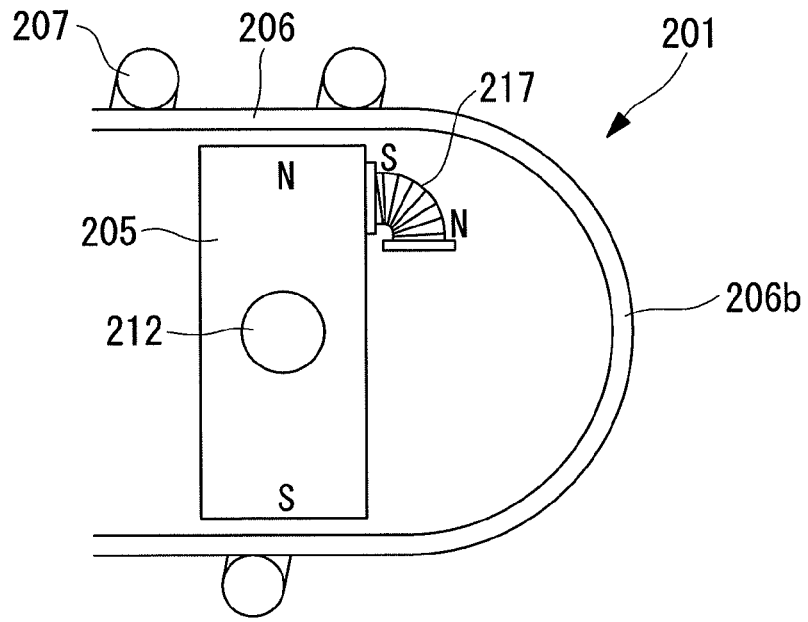
FIG. 14A is a longitudinal sectional view for illustrating the operation of a fifth modification of the capsule-type endoscope of FIG. 1.
Figure 14B:
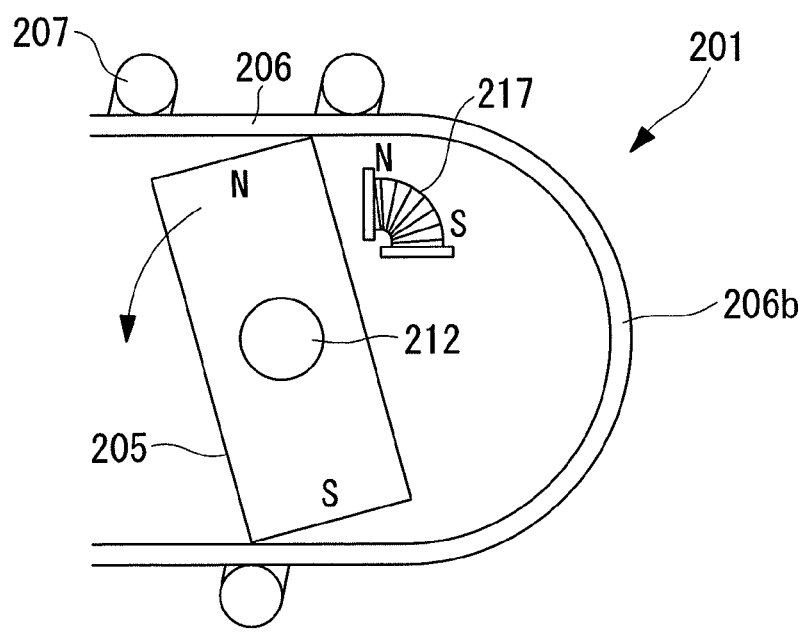
FIG. 14B is a longitudinal sectional view for illustrating the operation of the fifth modification of the capsule-type endoscope of FIG. 1.
Figure 14C:
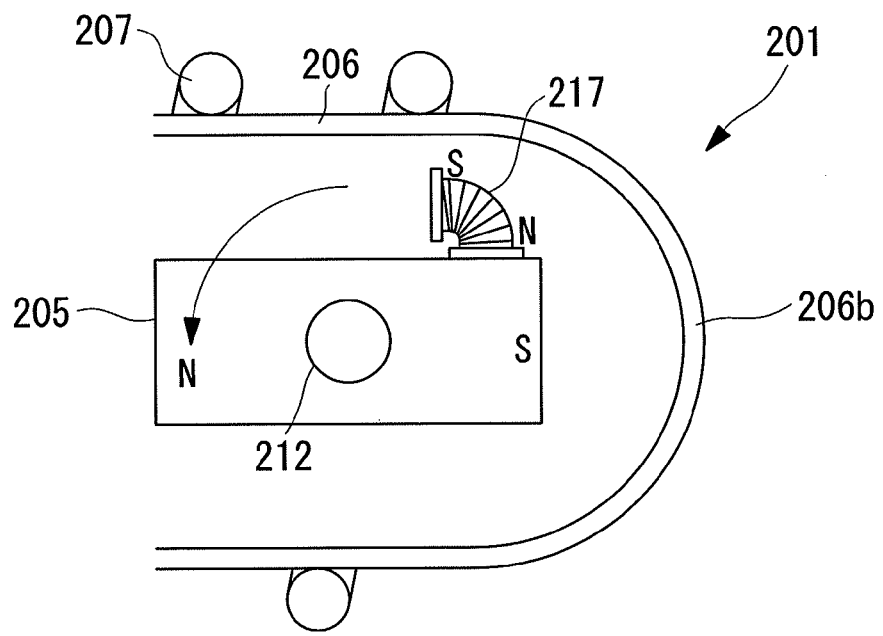
FIG. 14C is a longitudinal sectional view for illustrating the operation of the fifth modification of the capsule-type endoscope of FIG. 1.

Furthermore, for example, as shown in FIG. 14A to FIG. 14C, an electromagnet 217 that abuts against the permanent magnet 205 may be provided as the stopper, so that the magnetic-pole direction of the permanent magnet 205 may be changed by changing the magnetic pole of the region that abuts against the permanent magnet 205. A magnetic-pole-direction switching device (not shown in the figure) for switching the magnetic-pole direction of the electromagnet 217 in response to an external command signal is connected to the electromagnet 217.

In the example shown in FIG. 14A to FIG. 14C, when the advancing mode is selected, the corresponding magnetic pole of the electromagnet 217 is set to the south pole so that the north pole of the permanent magnet 205 is pulled into contact with the electromagnet 217, as shown in FIG. 14A. By doing so, the permanent magnet 205 is fixed so as to align its magnetic poles in a direction orthogonal to the longitudinal axis of the capsule 202. Once the magnetic poles of the permanent magnet 205 have been fixed, the electromagnet 217, serving as a magnetic object, can be held in contact with the permanent magnet 205 by turning off the power to the electromagnet 217. By doing so, battery consumption can be suppressed.

On the other hand, when the orientation-changing mode is selected, as shown in FIG. 14B, the magnetic pole of the electromagnet 217 that firmly holds the north pole of the permanent magnet 205 is changed to a north pole. As a result, a magnetic repulsive force between the permanent magnet 205 and the electromagnet 217 is generated, thus rotating the permanent magnet 205 away from the electromagnet 217.

Immediately, the south pole of the permanent magnet 205 is pulled into contact with the electromagnet 217 by setting the other magnetic pole of the electromagnet 217 to a north pole, as shown in FIG. 14C. By doing so, the permanent magnet 205 is held in a state where the magnetic poles are aligned in a direction along the longitudinal axis R of the capsule 202. Therefore, the magnetic-pole direction of the permanent magnet 205 can be changed more easily and reliably to switch the guidance mode quickly.

Furthermore, although, in this embodiment, the magnetic-pole direction of the permanent magnet 205 in the advancing mode is aligned in a direction orthogonal to the longitudinal axis R, the magnetic-pole direction may be set in a direction intersecting the longitudinal axis R at an angle smaller than 90°.

At the time of switching from the orientation-changing mode to the advancing mode, the direction of the external magnetic field M is set based on an image acquired by the image sensor 208. Alternatively, the magnetic-pole direction of the permanent magnet 205 in the orientation-changing mode may be set in a direction slightly angled towards the advancing mode from the direction along the longitudinal axis R. By doing so, an arbitrarily applied (or revolving) external magnetic field M orthogonal to the longitudinal axis R can produce a slight rotating torque, which causes the rotation axis 212 to be moved until it becomes orthogonal to the external magnetic field M so that switching to the advancing mode in the permanent magnet 205 can be carried out easily.

Second Embodiment

Next, a capsule-type endoscope according to a second embodiment of the present invention will be described with reference to FIG. 15A to FIG. 15C.

Figure 15A:
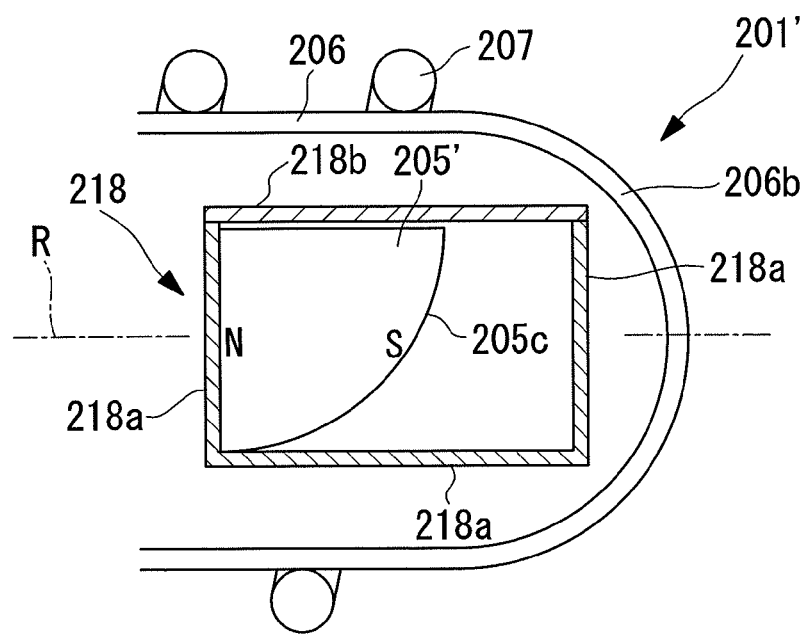
FIG. 15A is a longitudinal, partial sectional view for illustrating the operation of a capsule-type endoscope according to a second embodiment of the present invention.
Figure 15B:
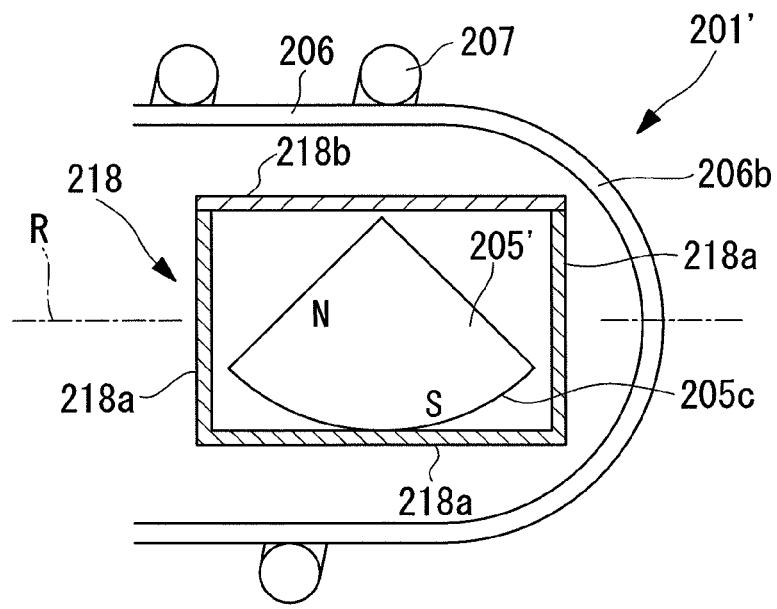
FIG. 15B is a longitudinal, partial sectional view for illustrating the operation of a capsule-type endoscope according to the second embodiment of the present invention.
Figure 15C:
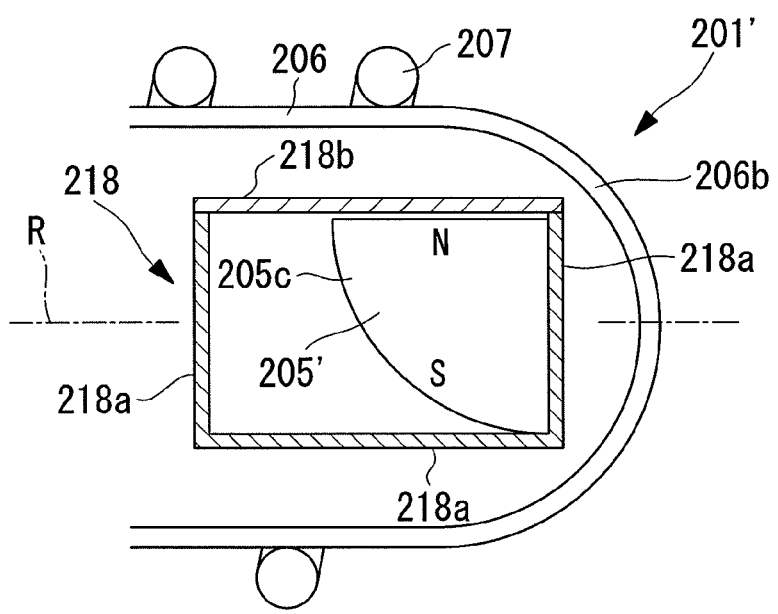
FIG. 15C is a longitudinal, partial sectional view for illustrating the operation of a capsule-type endoscope according to the second embodiment of the present invention.

As shown in FIG. 15A to FIG. 15C, a capsule-type endoscope 201' according to this embodiment includes a fan-shaped permanent magnet 205' having an arc-shaped portion 205c and a central angle of 90°; and a casing 218 accommodating the permanent magnet 205'.

The casing 218 includes wall surfaces 218a that are made of magnetic materials so as to hold by attraction the arc-shaped surface 205c of the permanent magnet 205' and the two side surfaces having the arc-shaped portion 205c interposed therebetween; and a wall surface 218b made of another non-magnetic material.

The permanent magnet 205' has one side surface magnetized as a north pole and has the arc-shaped portion magnetized as a south pole. As a result, as shown in FIG. 15A, while one side surface of the permanent magnet 205' is held in contact with one wall surface 218a, the magnetic poles of the permanent magnet 205' are aligned in a direction along the longitudinal axis R of the capsule 202, and therefore, the guidance mode is set to the orientation-changing mode. Furthermore, when the arc-shaped portion 205c rolls in contact with one wall surface 218a, as shown in FIG. 15B, and the other side surface is held in contact with another wall surface 218a, as shown in FIG. 15C, the magnetic poles of the permanent magnet 205' are aligned in a direction orthogonal to the longitudinal axis R of the capsule 202, which sets the guidance mode to the advancing mode.

According to the capsule-type endoscope 201' of this embodiment with the above-described structure, the guidance mode can be switched easily in the casing 218 by rolling the permanent magnet 205' through the operation of the external magnetic field M, as in the capsule-type endoscope 201 according to the first embodiment. Therefore, according to this embodiment, the capsule-type endoscope 201' featuring a simple mechanism, superior ease of assembly, low cost, and easy switching of the guidance mode between the advancing mode and the orientation-changing mode can be provided.

Figure 16:
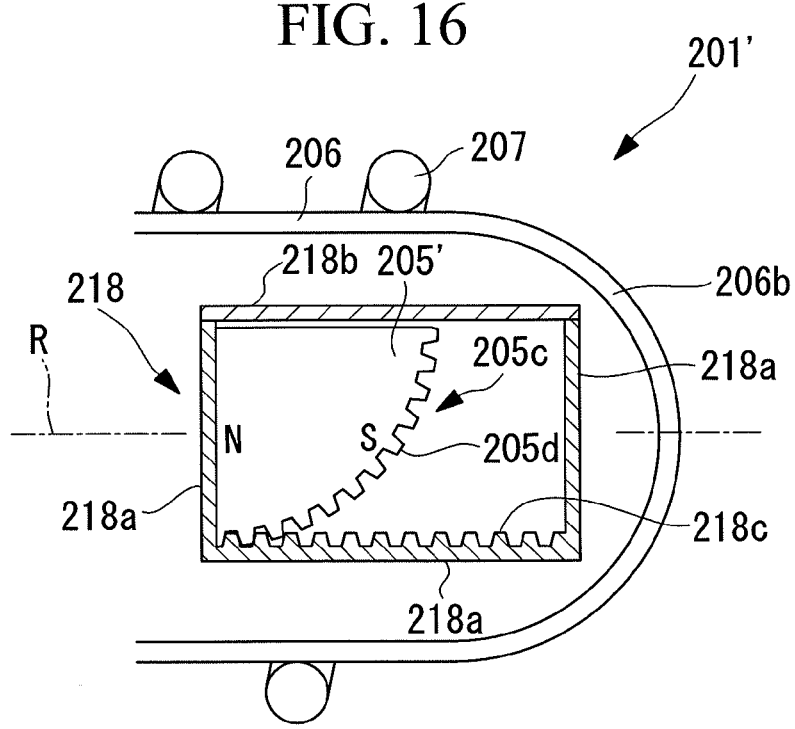
FIG. 16 is a longitudinal sectional view partially depicting a first modification of the capsule-type endoscope of FIG. 15A to FIG. 15C.

In this embodiment, the permanent magnet 205' is prevented from sliding and reorienting itself in the casing 218 because it is rolled while the arc-shaped portion 205c thereof is in contact with the wall surface 218a made of a magnetic material. Alternatively, as shown in FIG. 16, meshed gears 205d and 218c may be provided on the arc-shaped portion 205c and on the wall surface 218a of the casing 218 at which the arc-shaped portion 205c rolls. By doing so, the permanent magnet 205' is prevented from sliding on the casing 218, which ensures reliable switching of the magnetic-pole direction.

Figure 17:
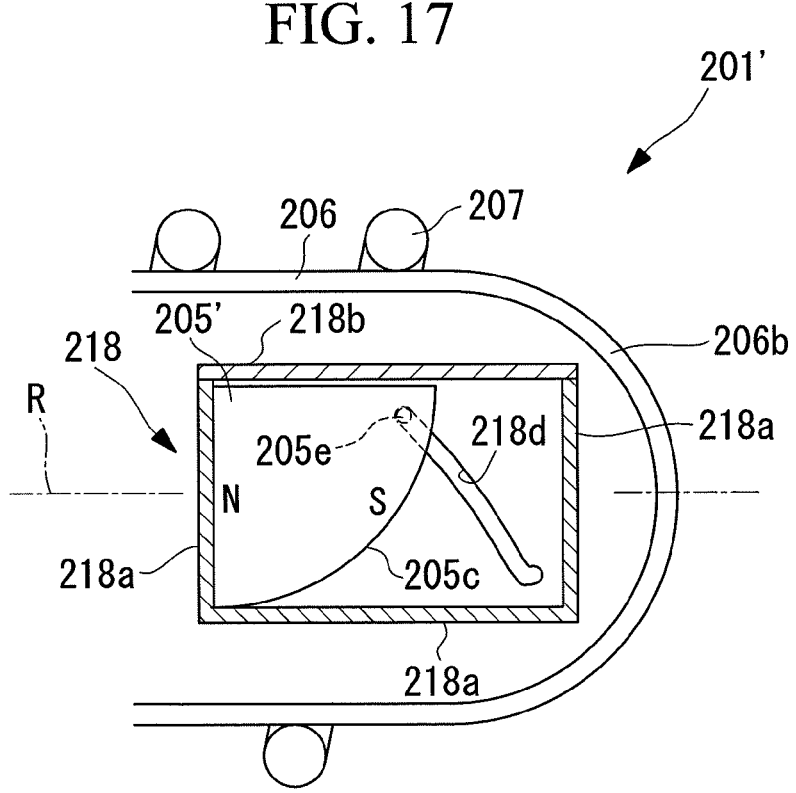
FIG. 17 is a longitudinal sectional view partially depicting a second modification of the capsule-type endoscope of FIG. 15A to FIG. 15C.

Furthermore, as shown in FIG. 17, a pin 205e may be provided on the permanent magnet 205', and furthermore, a cam groove 218d for guiding the pin 205e may be provided on the casing 218. By doing so, as with the magnetic gears 205d and 218c, the permanent magnet 205' can be guided reliably for desired movement, which ensures that the magnetic-pole direction is changed when the guidance mode is switched.

Figure 18:
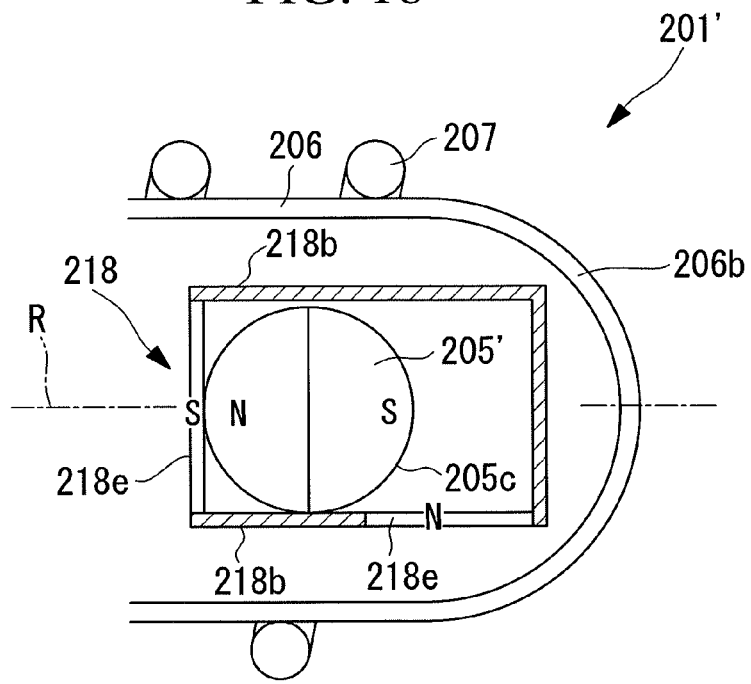
FIG. 18 is a longitudinal sectional view partially depicting a third modification of the capsule-type endoscope of FIG. 15A to FIG. 15C.

Furthermore, the permanent magnet 205' having the arc-shaped portion 205c is not limited to quarter-circle fan-shaped ones. Alternatively, a columnar permanent magnet 205', as shown in FIG. 18, may be employed. In this case, to restrict the degree of freedom of the permanent magnet 205' in the casing 218, wall surfaces 218e made of permanent magnets having a south pole and a north pole oriented towards the inner side of the casing 218 can be provided at two locations of the casing 218.

Third Embodiment

Next, a capsule-type endoscope 201" according to a third embodiment of the present invention will be described with reference to FIG. 19A to FIG. 19C.

Unlike the capsule-type endoscopes 201 and 201' according to the first and second embodiments where the guidance mode is switched by the external magnetic field M, the capsule-type endoscope 201" according to this embodiment switches the guidance mode by a mechanical pressing force F, which is applied externally.

Figure 19A:
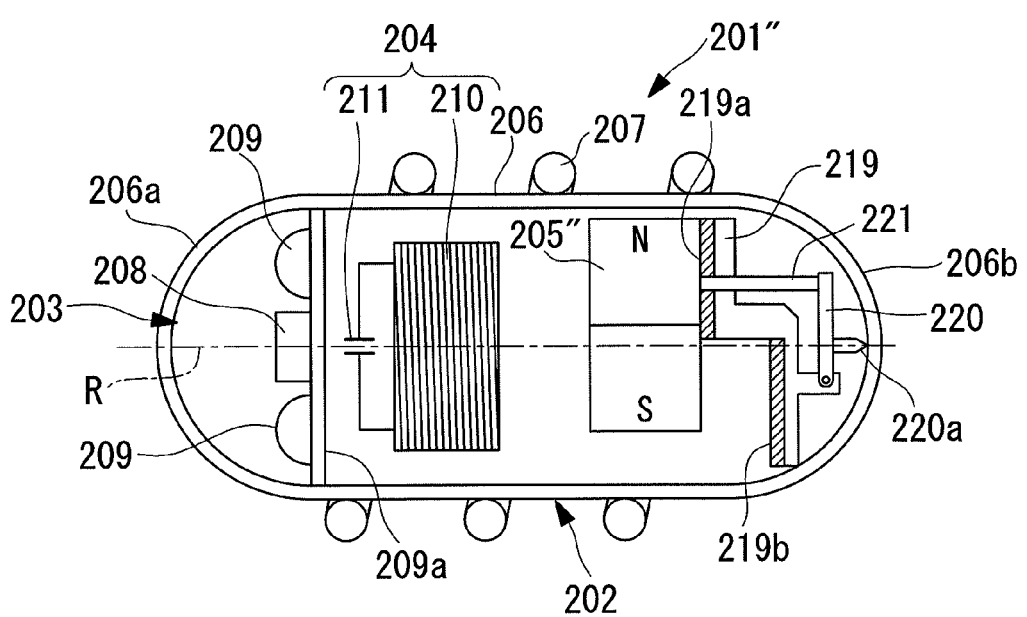
FIG. 19A is a longitudinal, partial sectional view for illustrating the operation of a capsule-type endoscope according to a third embodiment of the present invention.
Figure 19B:
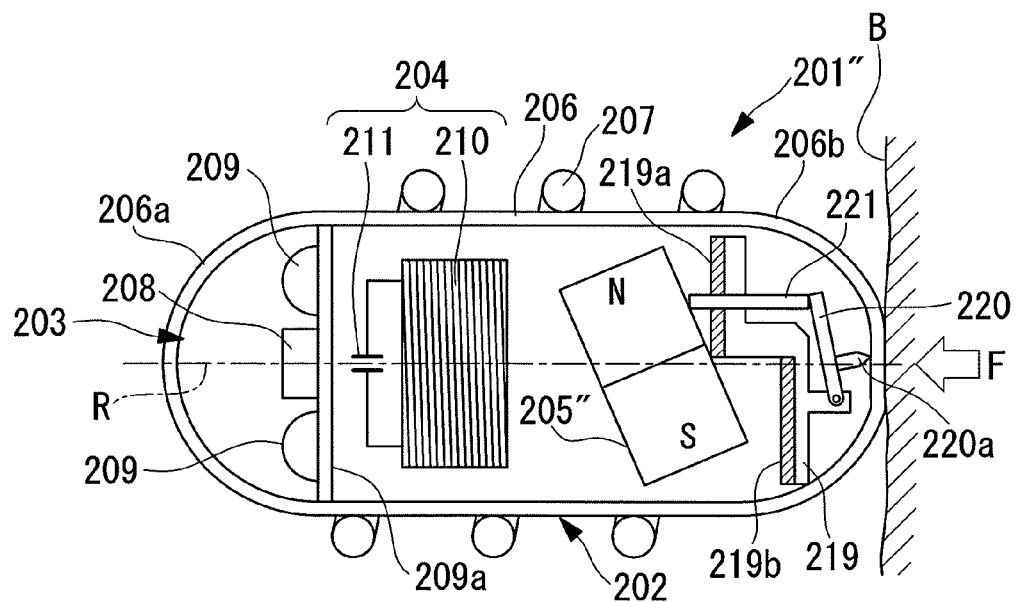
FIG. 19B is a longitudinal, partial sectional view for illustrating the operation of a capsule-type endoscope according to the third embodiment of the present invention.
Figure 19C:
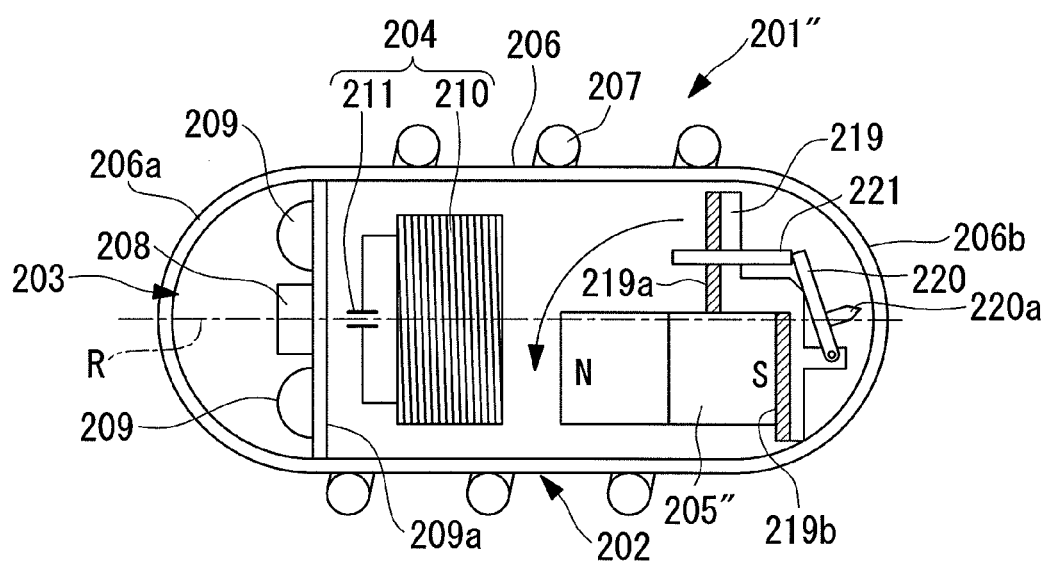
FIG. 19C is a longitudinal, partial sectional view for illustrating the operation of a capsule-type endoscope according to the third embodiment of the present invention.

As shown in FIG. 19A, the capsule-type endoscope 201" according to this embodiment includes a permanent magnet 205" shaped like a rectangular parallelepiped; a pedestal 219 that holds by attraction the permanent magnet 205"; a lever 220 pivotably provided on the pedestal 219; and a pressing rod 221 that presses the permanent magnet 205" off the pedestal 219 as a result of being pressed by the lever 220. Furthermore, the rear-end portion 206b of the capsule 202 is made of a flexible material and, therefore, is easily deformed when the external force F is applied, thereby transmitting the external force F to the lever 220. Reference symbol 220a in the figure denotes the point of the lever 220 to which the external force F is applied.

The pedestal 219 includes two attraction surfaces 219a and 219b that have a step therebetween. Each of the attraction surfaces 219a and 219b is made of a magnetic material in order to hold by attraction the permanent magnet 205".

The above-described pressing rod 221 is disposed such that it can move forward and backward through one attraction surface 219a of the pedestal 219.

The capsule-type endoscope 201" of this embodiment with the above-described structure is set to the advancing mode first, as shown in FIG. 19A, in which the magnetic poles of the permanent magnet 205" are aligned in a direction orthogonal to the longitudinal axis R of the capsule 202. Then, the capsule-type endoscope 201" is rotated about the longitudinal axis R through the operation of the guidance system 230 to advance the capsule-type endoscope 201" in a direction along the longitudinal axis R.

When the capsule-type endoscope 201" reaches the target position, the rear-end portion 206b of the capsule 202 is pressed against a wall surface B in the body cavity. To press the rear-end portion 206b, the capsule-type endoscope 201" is rotated in the reverse direction about the longitudinal axis R through the operation of the guidance system 230 to move the capsule-type endoscope 201" towards the rear-end portion 206b, an intense magnet is brought closer from the outside of the subject A to attract the capsule-type endoscope 201" in the body by a magnetic attraction force, or other techniques can be used.

When the rear-end portion 206b of the capsule 202 is pressed against the wall surface B in the body cavity, the rear-end portion 206b of the capsule 202 is deformed so that the external force F acts upon the point-of-force 220a to pivot the lever 220. As a result, the lever 220 presses the pressing rod 221 to cause the tip of the pressing rod 221 to come out from the attraction surface 219a. The permanent magnet 205" held in contact with the attraction surface 219a is separated from the attraction surface 219a and rotates, as shown in FIG. 19B.

Since the pedestal 219 is provided with a step, the other magnetic pole, which is different from the magnetic pole held in contact with the attraction surface 219a, is brought close to the other attraction surface 219b as the permanent magnet 205" rotates. When the other magnetic pole is moved closer by a predetermined distance, it comes into contact with the attraction surface 219b due to a magnetic attraction force, as shown in FIG. 19C. In this manner, the permanent magnet 205" rotates by 90°. In this state, the permanent magnet 205" aligns its magnetic poles in a direction along the longitudinal axis R of the capsule 202 to change the guidance mode to the orientation-changing mode.

Thereafter, the capsule-type endoscope 201" can bring the front-end portion 206a to a desired direction through the operation of the external magnetic field M, and an image of the wall surface in the body cavity in the vicinity of the target position can be acquired by freely changing the orientation. Then, when examination of the area in the vicinity of the target position is completed, the capsule-type endoscope 201" is discharged by, for example, the peristaltic motion of the body cavity.

Figure 20:
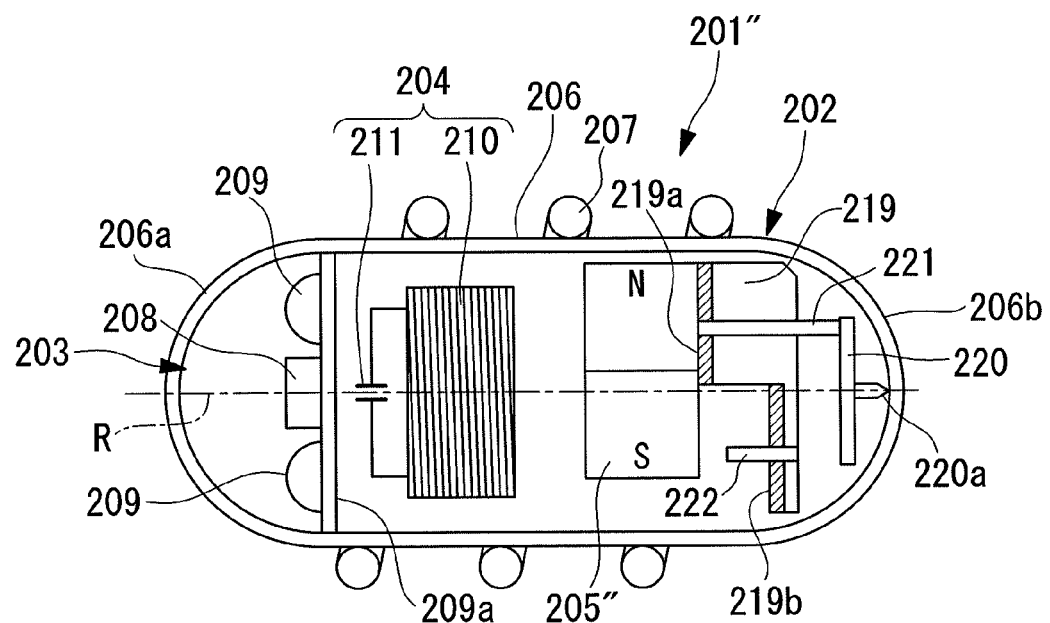
FIG. 20 is a longitudinal sectional view depicting a modification of the capsule-type endoscope of FIG. 19A to FIG. 19C.

In this embodiment, the guidance mode is switched only once from the advancing mode to the orientation-changing mode. Switching may be carried out in reverse from the orientation-changing mode to the advancing mode. Furthermore, as shown in FIG. 20, switching from the advancing mode to the orientation-changing mode and vice versa may be allowed any number of times by providing, adjacent to the attraction surface 219b, a second pressing rod 222 that is pressed by the permanent magnet 205" when the orientation-changing mode is entered.

Furthermore, although the guidance mode is switched by rotating the permanent magnets 205, 205', and 205" by 90° in the respective foregoing embodiments, alternatively, an electromagnet (not shown in the figure) whose magnetic poles can be aligned both in the direction along the longitudinal axis R of the capsule 202 and the direction orthogonal to the longitudinal axis R may be provided in the capsule 202, and a magnetic-pole switching device (not shown in the figure) for switching the magnetic poles according to an external command signal may be provided.

In addition, although the three-axis Helmholtz coil unit 271 is adopted as the magnetic-field generating apparatus in each of the foregoing embodiments, the magnetic-field generating apparatus is not limited to the Helmholtz type but may be realized by a planar magnetic device where a plurality of electromagnets is arranged in a plane to produce a substantially uniform magnetic field above these electromagnets. Alternatively, other types of magnetic device may be employed.

Furthermore, although a technique based on an induced magnetic field is used for the position detection system in each of the foregoing embodiments, the position detection system is not limited to this technique but can be realized by any technique as long as the direction of at least the longitudinal axis R of the capsule-type endoscope can be detected.

Next, embodiments related to an intrasubject insertion apparatus according to the present invention will be described with reference to the drawings.

The "spiral mechanism" in each of the foregoing embodiments corresponds to the "spiral-structured portion" in each of the following embodiments. Thus, embodiments where the spiral mechanism in each of the foregoing embodiments is replaced with the "spiral-structured portion" in each of the following embodiments are also covered by the scope of the present invention.

Fourth Embodiment

Figure 21:
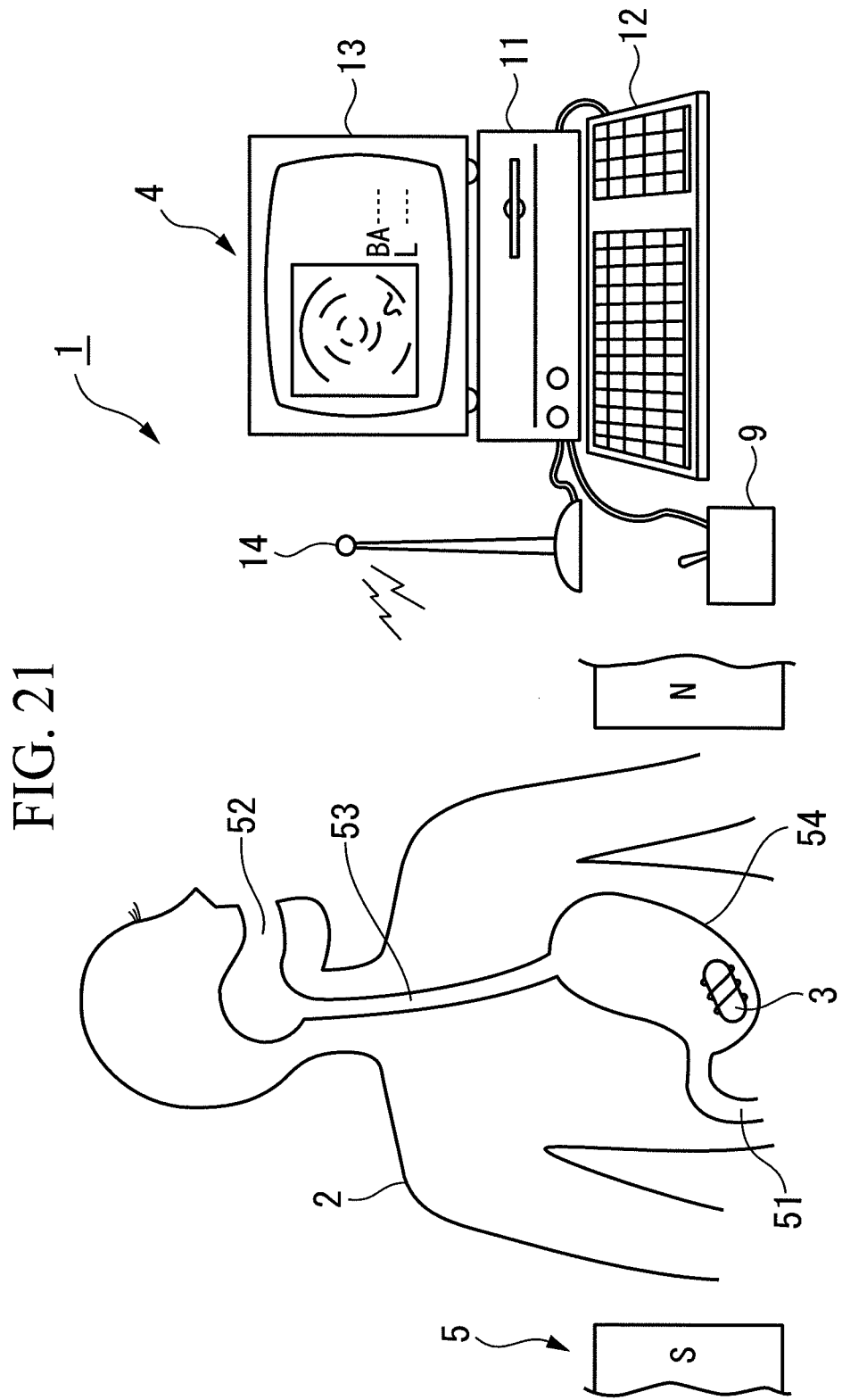
FIG. 21 is an overall schematic drawing depicting the structure of a capsule-medical-apparatus guidance system according to a fourth embodiment of the present invention.
Figure 22:
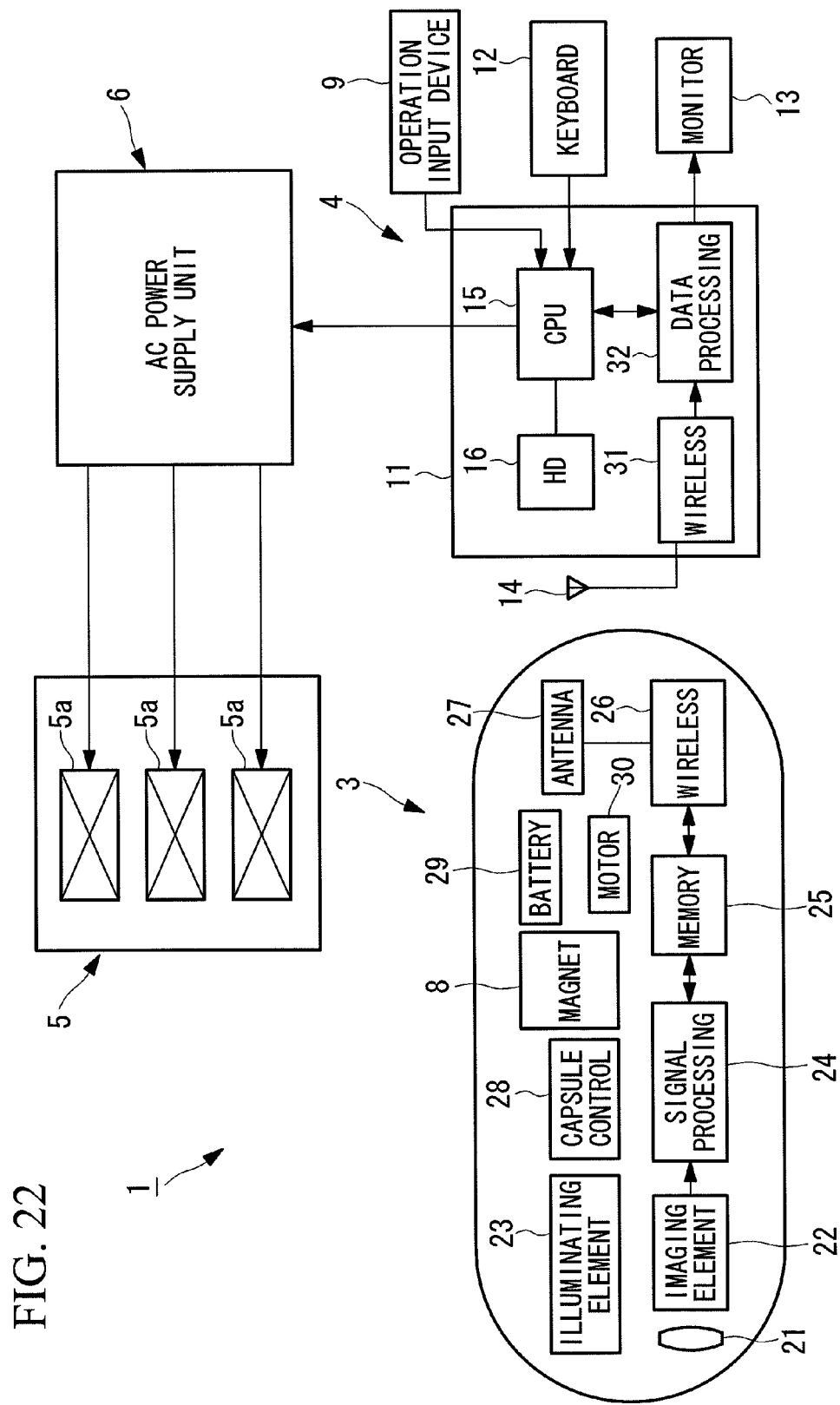
FIG. 22 is a block diagram depicting in more detail the structure shown in FIG. 21.
Figure 23:
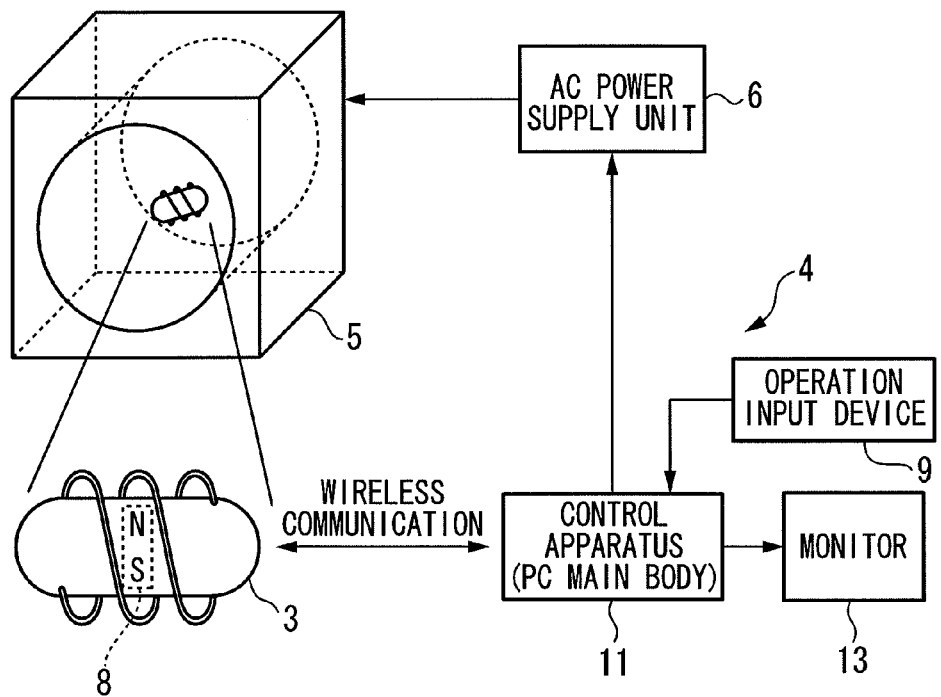
FIG. 23 is a schematic diagram depicting the structure of a magnetic-field generating apparatus.
Figure 24:
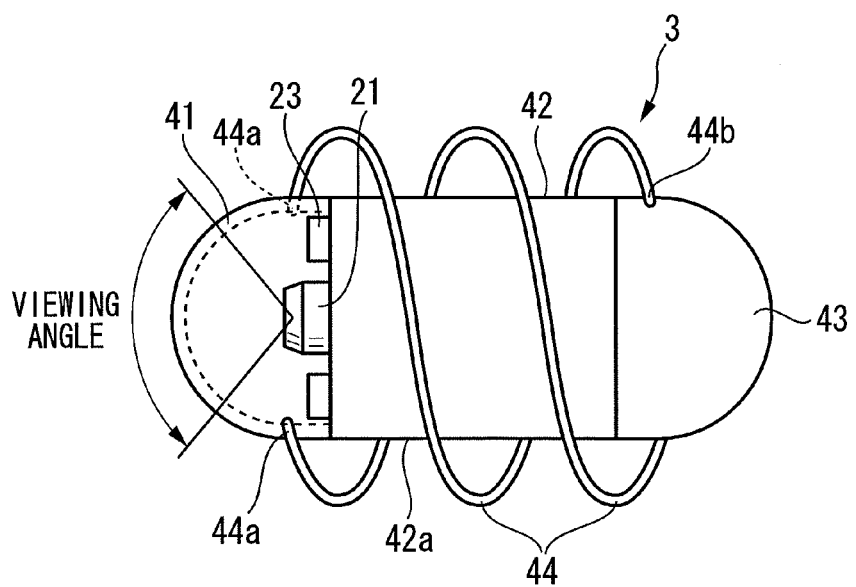
FIG. 24 is a side view of the external appearance of a capsule-type medical apparatus.
Figure 25:
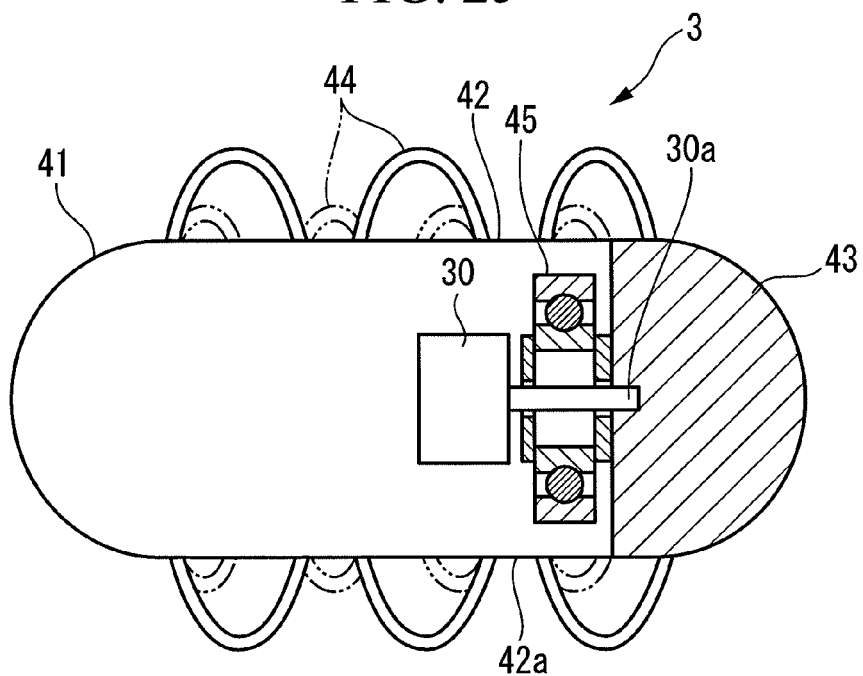
FIG. 25 is a schematic view of the structure of a capsule-type medical apparatus.
Figure 26:
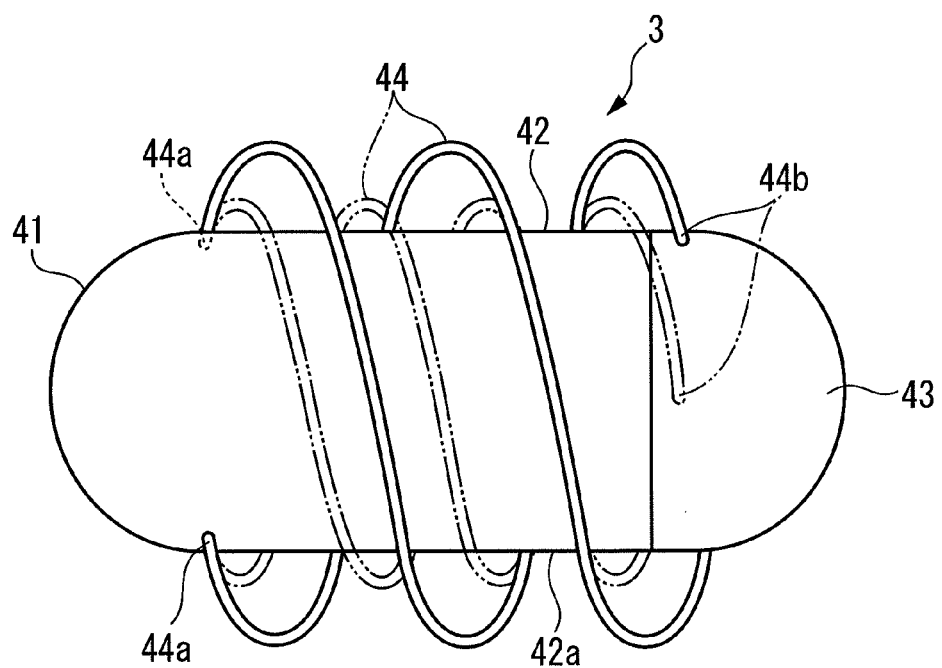
FIG. 26 illustrates how the spiral-outer-diameter of a spiral-structured portion changes as a capsule rear-end portion rotates.
Figure 27:
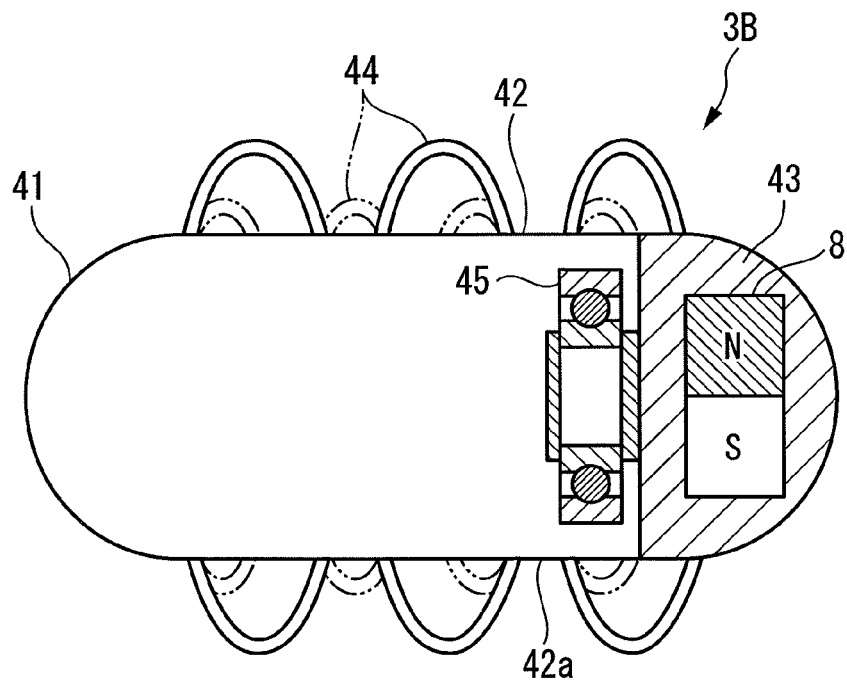
FIG. 27 is a schematic view of a first modification of the capsule-type medical apparatus of FIG. 25.
Figure 28:
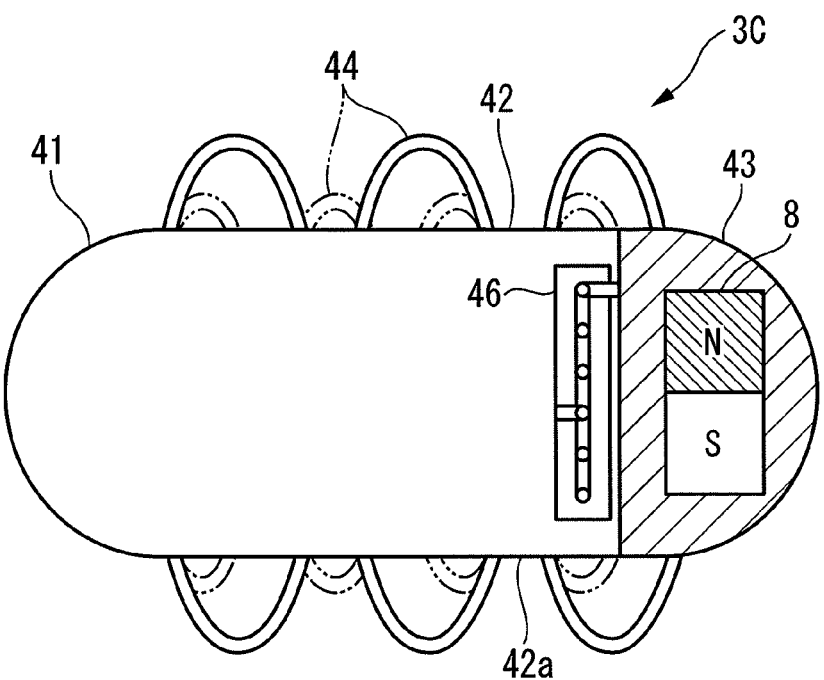
FIG. 28 is a schematic view of a second modification of the capsule-type medical apparatus of FIG. 25.

FIG. 21 to FIG. 28 relate to a fourth embodiment of the present invention. FIG. 21 is an overall schematic drawing depicting the structure of a capsule-medical-apparatus guidance system including the fourth embodiment of the present invention. FIG. 22 is a block diagram depicting in more detail the structure shown in FIG. 21. FIG. 23 is a schematic diagram depicting the structure of a magnetic-field generating apparatus. FIG. 24 is a side view of the external appearance of a capsule-type medical apparatus. FIG. 25 is a schematic view of the structure of a capsule-type medical apparatus. FIG. 26 illustrates how the spiral-outer-diameter of a spiral-structured portion changes as a capsule rear-end portion rotates. FIG. 27 is a schematic view of a first modification of the capsule-type medical apparatus of FIG. 25. FIG. 28 is a schematic view of a second modification of the capsule-type medical apparatus of FIG. 25.

As shown in FIG. 21, FIG. 22, and FIG. 23, a capsule-type-medical-apparatus guidance system (hereinafter, referred to as the capsule guidance system) 1, serving as an intrasubject insertion apparatus, includes a capsule-type medical apparatus (hereinafter, referred to just as the capsule) 3, serving as an insertion-portion main body; a capsule control apparatus (hereinafter, referred to just as the control apparatus) 4; a magnetic-field generating apparatus 5; and an AC power supply unit 6.

The above-described capsule 3 is shaped like a capsule so that it is inserted into the body cavity of a patient 2 (shown in FIG. 21) to examine the interior of the body cavity. The above-described control apparatus 4 is disposed outside the patient 2 and is realized by, for example, a personal computer which controls the operation of this capsule 3 through transmission and reception of electromagnetic waves to and from the capsule 3 and receives information transmitted from the capsule 3. The above-described magnetic-field generating apparatus 5 controls, for example, the direction of a revolving magnetic field to be applied to the capsule 3 to guide the capsule 3 to a desired direction (schematically shown in FIG. 21). The above-described AC power supply unit 6 supplies AC power for producing a revolving magnetic field (electromagnetic field, in a broader sense) to the magnetic-field generating apparatus 5.

As shown in FIG. 22, the above-described magnetic-field generating apparatus 5 includes, for example, three electromagnets 5a, 5b, and 5c. This magnetic-field generating apparatus 5 can produce a revolving magnetic field in three axial directions based on AC power supplied from the AC power supply unit 6 and controlled by the control apparatus 4. FIG. 23 schematically depicts the magnetic-field generating apparatus 5 in the form of (hollow, cubic) three-axis Helmholtz coils formed in three axial directions.

The capsule 3 includes a magnet 8, serving as a magnetic-field response portion, that exhibits a force in response to a revolving magnetic field formed by the magnetic-field generating apparatus 5. This magnet 8 is disposed, for example, on the longitudinal central axis of the capsule 3 such that the magnetic-pole direction of the magnet 8 is aligned in a direction orthogonal to this central axis and is secured with, for example, an adhesive (not shown in the figure). As a result, in the capsule 3, a revolving magnetic field produced by the magnetic-field generating apparatus 5 acts upon the magnet 8, and the capsule 3 is rotated by a rotary force applied to this magnet 8. In short, the magnet 8 constitutes a rotary mechanism.

The above-described magnet 8 is a permanent magnet such as a neodymium magnet, a samarium cobalt magnet, a ferrite magnet, an iron/chromium/cobalt magnet, a platinum magnet, or an alnico (AlNiCo) magnet. Rare-earth magnets, such as neodymium magnets and samarium cobalt magnets, have an advantage in that they exhibit a strong magnetic force and, therefore, the magnets to be incorporated in the capsule can be made small. On the other hand, ferrite magnets are advantageous in terms of their low cost. Platinum magnets exhibit high levels of corrosion resistance.

This magnet 8 is not limited to a permanent magnet but may be made of a coil. In this case, the magnet 8 may produce a magnetic force in the coil by electric current from a power supply unit such as a built-in battery; alternatively, a technique for magnetizing the coil by electrical power temporarily charged in a built-in capacitor is also acceptable. Furthermore, for the magnet 8, a technique for generating power by an internal coil, instead of a built-in power supply unit, storing this electrical power in a capacitor, and magnetizing another coil is also acceptable. In this case, the magnet 8 can operate for an extended period of time because it is not subjected to restrictions due to the capacity of a built-in battery. A power-generating coil may be made to serve as a magnet coil also.

The above-described magnetic-field generating apparatus 5 is disposed around the patient 2 (refer to FIG. 22). The AC power supply of the AC power supply unit 6 is controlled by the control apparatus 4, and the AC power supply unit 6 causes the magnetic-field generating apparatus 5 to produce a revolving magnetic field that acts upon the magnet 8 in a direction in which the capsule 3 is propelled. As a result, the capsule 3 inserted in a passage in the body cavity of the patient 2 can be propelled (guided) smoothly and efficiently. The direction of the revolving magnetic field produced by the magnetic-field generating apparatus 5 can be controlled by operating an operation input device 9 connected to the control apparatus 4.

As shown in FIG. 21, the control apparatus 4 includes a personal computer main body 11, a keyboard 12, a monitor 13, a external antenna 14, and the operation input device 9. The personal computer main body 11 includes a function for controlling the capsule 3 and (the AC power supply) of the magnetic-field generating apparatus 5. The keyboard 12 is connected to the personal computer main body 11 and inputs commands, data, and so forth. The monitor 13 is connected to the personal computer main body 11 and displays images etc. The external antenna 14 is connected to the personal computer main body 11, transmits a control signal for controlling the capsule 3, and receives a signal from the capsule 3. The operation input device 9 is connected to the personal computer main body 11 and inputs the direction of a revolving magnetic field etc.

The control apparatus 4 includes a CPU 15 as shown in FIG. 22. This CPU 15 generates a control signal for controlling the capsule 3 and the magnetic-field generating apparatus 5 based on the input from the keyboard 12 and the operation input device 9 or control programs stored in, for example, a hard disk 16 (refer to FIG. 22) in the personal computer main body 11.

The control signal for controlling the magnetic-field generating apparatus 5 is transmitted from the personal computer main body 11 to the AC power supply unit 6 via a connection cable. Based on this control signal, the magnetic-field generating apparatus 5 generates a revolving magnetic field. With the revolving magnetic field, the magnet 8 in the capsule 3 is magnetically acted upon and rotated by the revolving magnetic field generated by the magnetic-field generating apparatus 5, and thus the capsule 3 is endowed with a force to advance by means of a spiral-structured portion (described later).

The control signal for controlling the capsule 3 passes through an oscillating circuit in the personal computer main body 11, is modulated with a carrier wave having a predetermined frequency, and sent as electromagnetic waves from the external antenna 14. The capsule 3 receives the electromagnetic waves at an antenna 27 (described later), and the control signal is demodulated and output to various component circuits. Furthermore, the control apparatus 4 receives, at the external antenna 14, an information (data) signal, such as a video signal, transmitted from the wireless antenna 27 of the capsule 3 and displays it on the monitor 13.

As shown in FIG. 22, in addition to the magnet 8, an objective optical system 21 that forms an optical image; an imaging element 22 disposed at the image-forming position; and an illuminating element 23 disposed around the objective optical system 21 are provided in the capsule 3. Furthermore, in the capsule 3, a signal processing circuit 24; a memory 25; a wireless circuit 26; the antenna 27; a capsule control circuit 28; and a battery 29 are stored.

The signal processing circuit 24 performs signal processing on the signal acquired by the imaging element 22. The memory 25 temporarily stores a digital video signal generated by the signal processing circuit 24. The wireless circuit 26, modulates a video signal read out from the memory 25 with a high frequency signal to convert it into a signal to be transmitted wirelessly, demodulates the control signal transmitted from the control apparatus 4, and so forth. The antenna 27 transmits and receives electromagnetic waves to and from the external antenna 14. The capsule control circuit 28 controls the capsule 3, such as the signal processing circuit 24. The battery 29 supplies operating power to the electrical system including the signal processing circuit 24, in the capsule 3. A motor 30 constituting a spiral-outer-diameter change-imparting portion is provided in the capsule 3, as will be described later.

Furthermore, the personal computer main body 11 constituting the control apparatus 4 includes a wireless circuit 31; a data processing circuit 32; the CPU 15; and the hard disk 16. The wireless circuit 31 is connected to the external antenna 14 and wirelessly communicates with the wireless circuit 26 (in the capsule 3). The data processing circuit 32 is connected to the wireless circuit 31 and carries out data processing, for example, to display image data sent from the capsule 3. The CPU 15 is control means for controlling the data processing circuit 32, the AC power supply unit 6, and so forth. The hard disk 16 stores programs, data, and so forth.

The operation input device 9 for performing the operation of setting the direction of a revolving magnetic field and the keyboard 12 for inputting commands and data are connected to the CPU 15. The monitor 13 is connected to the data processing circuit 32. Information, such as images, acquired by the imaging element 22, sent via the wireless circuits 26 and 31, and processed by the data processing circuit 32 is displayed on this monitor 13. In addition, because images are acquired while the capsule 3 is rotating, this data processing circuit 32 performs the process of correcting an image to be displayed on the monitor 13 so that the image has a constant orientation, thus providing an image that is easy for the operator to observe.

As shown in FIG. 24, the capsule 3 includes a substantially hemispherical front-end cover 41; a substantially cylindrical capsule main body 42; and a substantially hemispherical capsule rear-end portion 43. The front-end cover 41 is formed of a transparent member and is hermetically connected to the capsule main body 42. The capsule main body 42 is hermetically integrated with the front-end cover 41. The capsule rear-end portion 43 is designed such that it is rotatable relative to the capsule main body 42 by a predetermined angle while maintaining a hermetic seal.

A propulsion-generating spiral-structured portion 44 for converting rotational motion into a propulsion force through rotation while in contact with a wall in the lumen is provided on an outer surface 42a of the capsule main body 42. This spiral-structured portion 44 is wound spirally around the outer surface 42a of the capsule main body 42, being separated from the outer surface 42a in the radial direction.

The front-end side of the spiral-structured portion 44 extends to the front-end cover 41 via the cylindrical outer circumferential surface of the capsule main body 42, and a front end 44a thereof is secured at an intermediate point on the front-end cover 41, more specifically, at a point outside the viewing angle of the objective lens 21. Furthermore, a rear end 44b of this spiral-structured portion 44 extends to a point near the boundary of the capsule rear-end portion 43 and is secured at that point. The spiral-structured portion 44 has a duplicated (double) structure where one spiral-structured portion 44 is provided at a central position of another spiral-structured portion 44.

As shown in FIG. 25, the capsule main body 42 and the capsule rear-end portion 43 are rotatably connected to each other via a bearing 45. The motor 30 for freely rotating the capsule rear-end portion 43 by a predetermined angle is provided on the capsule main body 42. This motor 30 is, for example, a pulsed motor. A drive shaft 30a of this motor 30 is connected to the capsule rear-end portion 43 through the bearing 45. Therefore, in the capsule 3, when the motor 30 is rotated by a predetermined angle, the capsule rear-end portion 43 is rotated relative to the capsule main body 42 by a predetermined angle.

By doing so, in the capsule 3, the capsule rear-end portion 43 is rotated by a predetermined angle according to the diameter of a passage in the body cavity, as shown in FIG. 26, and accordingly, the fixing position of the rear end 44b of the spiral-structured portion 44 rotates by a predetermined angle and moves in the outer circumferential direction of the capsule 3 relative to the fixing position of the front end 44a of the spiral-structured portion 44. In this manner, the spiral-outer-diameter of the spiral-structured portion 44 can be changed. The motor 30 is connected to a motor control circuit (not shown in the figure), and this motor control circuit controls and drives the motor 30 based on a control signal transmitted from the control apparatus 4.

Next, the operation of the capsule guidance system 1 will be described.

If the operator wishes to examine the interior of a passage in the body cavity of the patient 2, such as a duodenum 51 or a small intestine, as shown in FIG. 21, the patient 2 is first ordered to swallow the capsule 3. The capsule 3 is prepared so that the spiral-structured portion 44 has a minimum spiral-outer-diameter to help the patient 2 swallow it comfortably.

Furthermore, just before the patient 2 swallows the capsule 3, the operator turns on a switch (not shown in the figure) of the capsule 3 so that electrical power from the battery 29 is transmitted to, for example, the illuminating element 23. At the same time, the operator starts up (turns on) the magnetic-field generating apparatus 5 and performs magnetic control so that the capsule 3 can reach the target site easily in the passage inside the body cavity with the help of a revolving magnetic field generated by this magnetic-field generating apparatus 5.

As described above, in the capsule 3, when the revolving magnetic field generated by the magnetic-field generating apparatus 5 acts upon the magnet 8, the capsule main body 42 rotates due to the effect on this magnet 8.

The capsule 3 is moved forward as the rotation of the capsule main body 42 generates a propulsion force, upon contact between the spiral-structured portion 44 and the wall in the lumen in the passage in the body cavity, and this propulsion force advances the capsule main body 42 as if a male screw were engaged with a female screw. Furthermore, along with the rotation of the revolving magnetic field, the direction of movement (orientation) of the capsule 3 is changed while the capsule main body 42 is rotating so that the rotational plane of the magnet 8 is aligned with the rotational plane of the revolving magnetic field. At this time, the capsule 3 can be propelled smoothly towards the target site in the passage inside the body cavity without experiencing unwanted motion, such as eccentric motion, of the capsule main body 42.

The capsule 3 passes through an oral cavity 52 and an esophagus 53 and reaches a stomach 54. If examination of the stomach 54 is necessary, the operator performs key input corresponding to a command for starting examination using, for example, the keyboard 12 of the control apparatus 4. Then, the control signal resulting from this key input is radiated as electromagnetic waves via the external antenna 14 of the control apparatus 4 and transmitted to the capsule 3.

The capsule 3 detects a signal indicating the start of operation with the signal received at the antenna 27, and the illuminating element 23, the imaging element 22, the signal processing circuit 24, and so forth are operated. In the capsule 3, the target site in the passage inside the body cavity is illuminated with illumination light from the illuminating element 23. Reflected light from the illuminated target site is acquired as an optical image via the objective lens 21, focused on the imaging element 22, and subjected to photoelectric conversion. The imaging signal from the imaging element 22 is subjected to A/D conversion, digital signal processing, and finally compression processing by the signal processing circuit 24. The digital signal subjected to compression processing is stored in the memory 25, modulated in the wireless circuit 26, and radiated from the antenna 27 as electromagnetic waves.

These electromagnetic waves are received at the external antenna 14 of the control apparatus 4 and demodulated at the wireless circuit 31 in the personal computer main body 11. The demodulated signal is converted into a digital video signal through another A/D conversion by the data processing circuit 32, stored in a memory and the hard disk 16 of the data processing circuit 32, read out at a predetermined speed, and output to the monitor 13. The optical image acquired by the capsule 3 is displayed in color on the monitor 13.

The operator observes this monitor image to see the interior of, for example, the stomach 54 of the patient 2. The operator can manipulate operating means, such as a joystick, of the operation input device 9 to easily control how to apply an external magnetic force such that the entire stomach 54 can be viewed. After completing examination of the stomach 54, the operator can magnetically guide the capsule 3 from the stomach 54 to the duodenum 51 by controlling the orientation of the revolving magnetic field generated by the magnetic-field generating apparatus 5.

Also in the duodenum 51, the operator can propel the capsule 3 smoothly by controlling the orientation of the revolving magnetic field so that the capsule 3 advances along the lumen. Even when the capsule 3 is to be advanced in a winding passage, like in the small intestine, since the spiral ridge 44 extends up to near the spherical end portion of the capsule main body 42, the operator can advance the capsule 3 smoothly also in such a winding passage.

At this time, based on the monitor image, the operator can issue a command for setting the spiral-structured portion 44 of the capsule 3 to have a desirable spiral-outer-diameter in accordance with the diameter of the passage inside the body cavity by operating the operation input device 9 or the keyboard 12, thus producing a desired propulsion force. More specifically, if a sufficiently large propulsion force cannot be produced because the diameter of the passage inside the body cavity is too large, compared to the spiral-outer-diameter of the spiral-structured portion 44, to achieve satisfactorily close contact between the wall in this lumen and the spiral-structured portion 44, the operator issues a command for increasing the spiral-outer-diameter of the spiral-structured portion 44.

The operator performs key input corresponding to the command using, for example, the keyboard 12 of the control apparatus 4. A control signal resulting from this key input, is radiated via the external antenna 14 of the control apparatus 4 as electromagnetic waves and transmitted to the capsule 3. The capsule 3 detects a motor control signal from the signal received at the antenna 27, and, based on this motor control signal, the motor control circuit controls and drives the motor 30. In the capsule 3, the motor 30 rotates by a predetermined angle to cause the capsule rear-end portion 43 to rotate by a predetermined angle relative to the capsule main body 42 so that the spiral-outer-diameter of the spiral-structured portion 44 is increased.

Along with this rotation of the capsule rear-end portion 43, the spiral-structured portion 44 comes to have a large spiral-outer-diameter as a result of the fixing position of the rear end 44b being brought closer to the fixing position of the front end 44a. Consequently, the capsule 3 can obtain a sufficiently large propulsion force since satisfactorily close contact between the wall in the lumen and the spiral-structured portion 44 is achieved even when the diameter of the passage inside the body cavity is large.

Thereafter, if the spiral-outer-diameter of the spiral-structured portion 44 is larger than the diameter of the passage inside the body cavity, the operator issues a command for reducing the spiral-outer-diameter of the spiral-structured portion 44. As described above, the control signal resulting from the key input by the operator is radiated via the external antenna 14 of the control apparatus 4 as electromagnetic waves and transmitted to the capsule 3. In the capsule 3, the motor control circuit controls and drives the motor 30 based on the motor control signal detected from the signal received at the antenna 27.

In the capsule 3, the motor 30 rotates in the reverse direction by a predetermined angle to cause the capsule rear-end portion 43 to rotate in the reverse direction by a predetermined angle relative to the capsule main body 42 so that the spiral-outer-diameter of the spiral-structured portion 44 becomes small. Along with this reverse rotation of the capsule rear-end portion 43, the fixing position of the rear end 44b moves away from the fixing position of the front end 44a to reduce the spiral-outer-diameter of the spiral-structured portion 44.

Consequently, the capsule 3 can obtain a sufficiently large propulsion force since the spiral-outer-diameter of the spiral-structured portion 44 can be reduced to achieve appropriate contact between the wall in the lumen and the spiral-structured portion 44 even when the diameter of the passage inside the body cavity is small. Thus, the capsule 3 can change the spiral-outer-diameter of the spiral-structured portion 44 according to the diameter of the passage inside the body cavity.

As described above, according to this embodiment, since the spiral-outer-diameter of the spiral-structured portion 44 can be changed according to the diameter of the passage in the body cavity, a stable propulsion force can be obtained by ensuring an appropriate spiral shape of the spiral-structured portion 44. Furthermore, since the capsule 3 of this embodiment allows the spiral-outer-diameter to be changed by changing the relative position between the front end 44a and the rear end 44b of the spiral-structured portion 44, a simple and compact structure can be realized. In addition, since the capsule 3 of this embodiment changes the spiral-outer-diameter of the spiral-structured portion 44 by rotating the capsule rear-end portion 43 in the circumferential direction, a change in the spiral-outer-diameter does not adversely affect the rotation for producing a propulsion force, which improves the ease of insertion in depth direction of the passage inside the body cavity.

Although the fixing position of the rear end 44b of the spiral-structured portion 44 is shifted relative to the fixing position of the front end 44a in the capsule 3, the present invention is not limited to this. The fixing position of the front end 44a of the spiral-structured portion 44 may be shifted instead. Alternatively, the fixing positions of both the front end 44a and the rear end 44b may be shifted.

In the capsule, the capsule rear-end portion 43 may be rotated using the magnet 8 instead of the motor 30. As shown in FIG. 27, in a capsule 3B, the magnet 8, serving as a rotary mechanism, is secured to the capsule rear-end portion 43 that is constructed so as to be capable of rotation with respect to the capsule main body 42 by means of the bearing 45.

Not only does this capsule 3B rotate the capsule rear-end portion 43 relative to the capsule main body 42 through the rotation of the magnet 8, but also the capsule 3B rotates the capsule rear-end portion 43 together with the capsule main body 42 to obtain a propulsion force for advancement into the passage inside the body cavity.

More specifically, in the capsule 3B, the capsule rear-end portion 43 always rotates in a direction so as to increase the spiral-outer-diameter of the spiral-structured portion 44 as a result of the revolving magnetic field, produced by the magnetic-field generating apparatus 5, acting upon the magnet 8. In the capsule 3B, when the spiral-structured portion 44 comes into contact with a wall in the lumen, the capsule rear-end portion 43 rotates by a certain angle depending on the load applied to the spiral-structured portion 44 in contact with this wall in the lumen and then stops; subsequently, this capsule rear-end portion 43 and the capsule main body 42 start to rotate integrally to produce a propulsion force for advancement into the passage inside the body cavity.

By doing so, in the capsule 3B, the spiral-structured portion 44 comes to have an optimal spiral-outer-diameter according to the contact with the wall in the lumen, which produces a stable propulsion force by ensuring an appropriate spiral shape of the spiral-structured portion 44. According to this modification, not only can the spiral-structured portion 44 be made to have an optimal spiral-outer-diameter with the help of the magnet 8, serving as a rotary mechanism, but also a propulsion force can be obtained. Accordingly, a simple and compact structure can be realized. Furthermore, in the capsule 3B of this modification, because a force is always applied in a direction to cause the spiral-structured portion 44 to come into contact with the wall in the lumen during rotation, a stable propulsion force is obtained, which improves the ease of insertion in the depth direction of the passage inside the body cavity.

Alternatively, in the capsule, the capsule rear-end portion 43 may be rotated by a predetermined angle using a spiral spring. As shown in FIG. 28, in a capsule 3C, the capsule main body 42 and the capsule rear-end portion 43 are rotatably connected with a spiral spring 46 serving as a rotary mechanism.

The spiral spring 46 has one end thereof secured to the capsule main body 42 and the other end thereof secured to the capsule rear-end portion 43 so as to exert an urging force in a direction to always increase the spiral-outer-diameter of the spiral-structured portion 44. By doing so, in the capsule 3C, the spiral-structured portion 44 rotates by a predetermined angle while in contact with the wall in the lumen against the urging force of the spiral spring 46, and thereby, the spiral-structured portion 44 comes to have an optimal spiral-outer-diameter according to the contact with the wall in the lumen, which produces a stable propulsion force by ensuring an appropriate spiral shape of the spiral-structured portion 44.

According to this modification, the spiral-outer-diameter of the spiral-structured portion 44 can be changed automatically according to the diameter of the passage inside the body cavity. Furthermore, since the capsule 3C of this modification does not require energy for controlling the spiral-outer-diameter of the spiral-structured portion 44 and is simple in structure, it can be made small. In addition, since a force in a direction to increase the spiral-outer-diameter is constantly generated in the capsule 3C of this modification, the spiral-structured portion 44 can be held in contact with the wall in the lumen, which produces a stable propulsion force and therefore improves the ease of insertion in the depth direction of the passage inside the body cavity.

Although this embodiment is constructed by applying the present invention to a capsule functioning as a capsule-type endoscope for imaging the interior of the body cavity, the present invention is not limited to this. The present invention may also be applied to a tissue-collecting capsule including collecting means for collecting biological tissue; a drug-release capsule that discharges pharmaceutical drugs; and a cauterizing capsule for cauterizing biological tissue.

Fifth Embodiment

Figure 29:
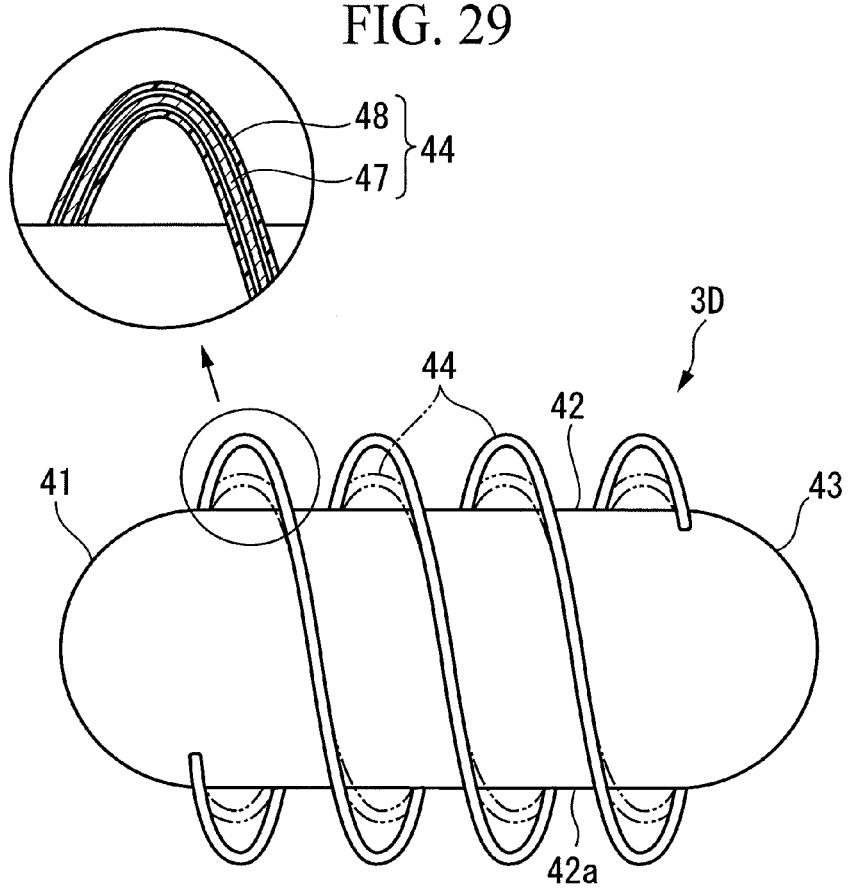
FIG. 29 illustrates a capsule-type medical apparatus according to a fifth embodiment of the present invention.
Figure 30:
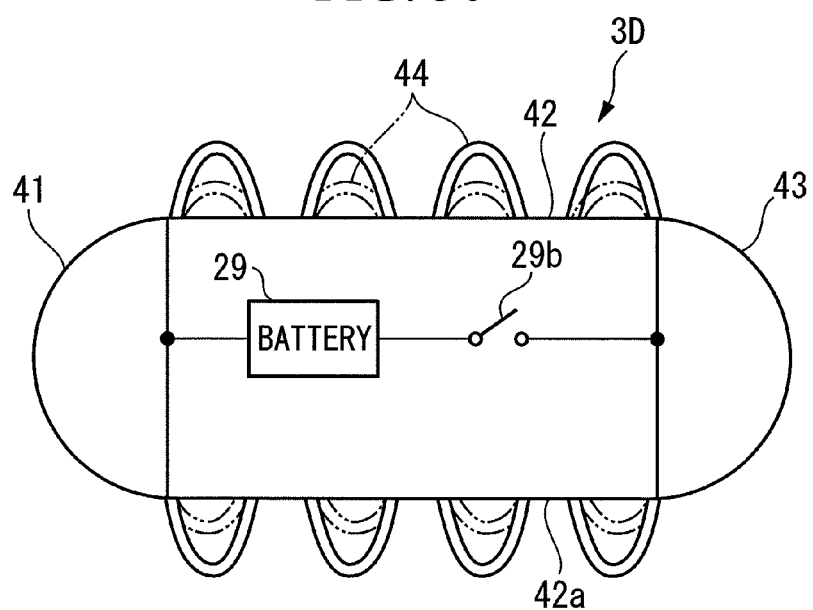
FIG. 30 is a schematic view of the structure of the capsule-type medical apparatus of FIG. 29.

FIG. 29 and FIG. 30 relate to a fifth embodiment of the present invention. FIG. 29 illustrates a capsule-type medical apparatus according to the fifth embodiment of the present invention. FIG. 30 is a schematic view of the structure of the capsule-type medical apparatus of FIG. 29.

In the fourth embodiment, the spiral-outer-diameter change-imparting portion is designed so as to change the spiral-outer-diameter by shifting the fixing position of one of the front end 44a and the rear end 44b of the spiral-structured portion 44 in the outer circumferential direction of the capsule 3. In the fifth embodiment, the spiral-outer-diameter change-imparting portion is designed to change the spiral-outer-diameter by inflating and deflating the spiral-structured portion 44 which is separated from the outer surface 42a of the capsule main body 42. The components other than the above-described point are similar to those in the above-described fourth embodiment. The same components are denoted by the same reference numerals, and hence a description thereof will be omitted.

As shown in FIG. 29 and FIG. 30, in a capsule 3D of the fifth embodiment, the spiral-structured portion 44 is formed of a coil 47 made of a shape-memory alloy (hereinafter, abbreviated as "SMA"). Unlike the capsule in the above-described fourth embodiment, the capsule rear-end portion 43 of the capsule 3D according to this embodiment does not rotate but is integral with the capsule main body 42.

In the spiral-structured portion 44, the SMA coil 47 is disposed to pass through an elastic, extensible outer casing tube 48. A front end 48a of the outer casing tube 48 is secured at an intermediate point on the front-end cover 41, more specifically, at a point outside the viewing angle of the objective lens 21, whereas a rear end 48b of the outer casing tube 48 extends to a point near the boundary of the capsule rear-end portion 43 and is secured at that point.

Both ends of the SMA coil 47 extend into the capsule main body 42, and the SMA coil 47 constitutes a closed circuit together with the battery 29 and a switch 29b. The switch 29b is turned on/off with, for example, a control signal transmitted from the control apparatus 4 to supply or stop electrical power from the battery 29 to the SMA coil 47.

By doing so, in the spiral-structured portion 44, the switch 29b is turned on to supply power from the battery 29 to the SMA coil 47, the SMA coil 47 contracts, and the outer casing tube 48 also contracts, thereby reducing the overall length of the spiral-structured portion 44 to reduce the spiral-outer-diameter. On the other hand, when the power is turned off, the overall length of the spiral-structured portion 44 is restored (increased) due to the elastic force of the outer casing tube 48, thus increasing the spiral-outer-diameter of the spiral-structured portion 44. In short, the SMA coil 47 and the outer casing tube 48, the switch 29b, and the battery 29 constitute the spiral-outer-diameter change-imparting portion.

Therefore, in the capsule 3D, the spiral-outer-diameter can be changed by inflating and deflating, in the spiral direction, the spiral-structured portion 44 separated from the outer surface 42a of the capsule main body 42. According to this embodiment, not only can similar advantages to those in the above-described fourth embodiment be provided, but also the spiral-outer-diameter can be changed by inflating and deflating the spiral-structured portion 44 in the spiral direction. This ensures that the spiral-outer-diameter can be changed without causing the spiral shape to be deformed.

Sixth Embodiment

Figure 31:
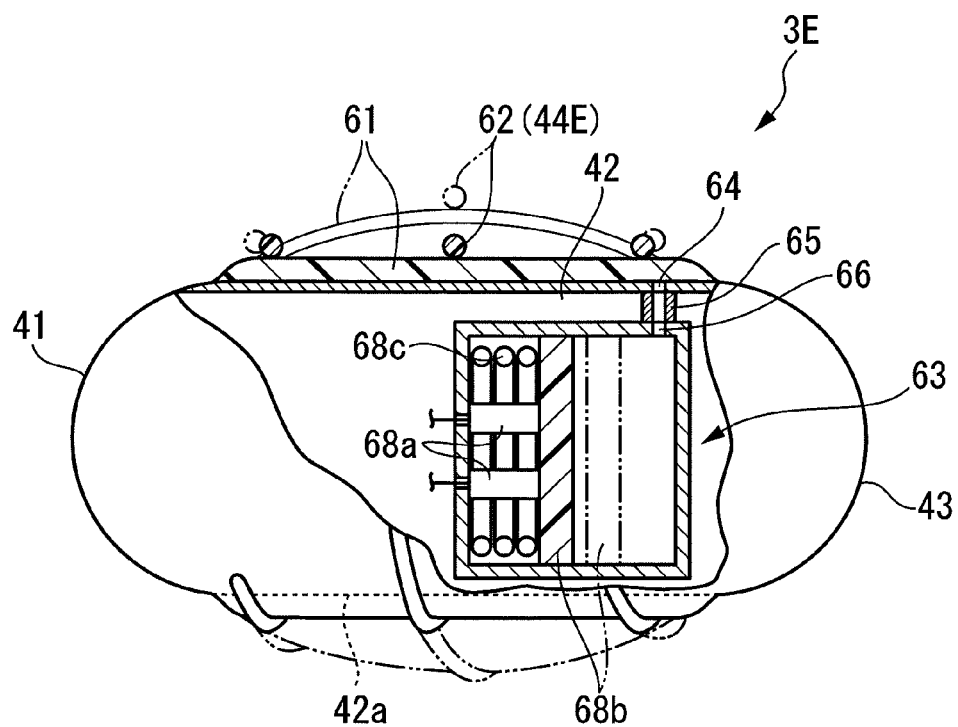
FIG. 31 illustrates a capsule-type medical apparatus according to a sixth embodiment of the present invention.
Figure 32:
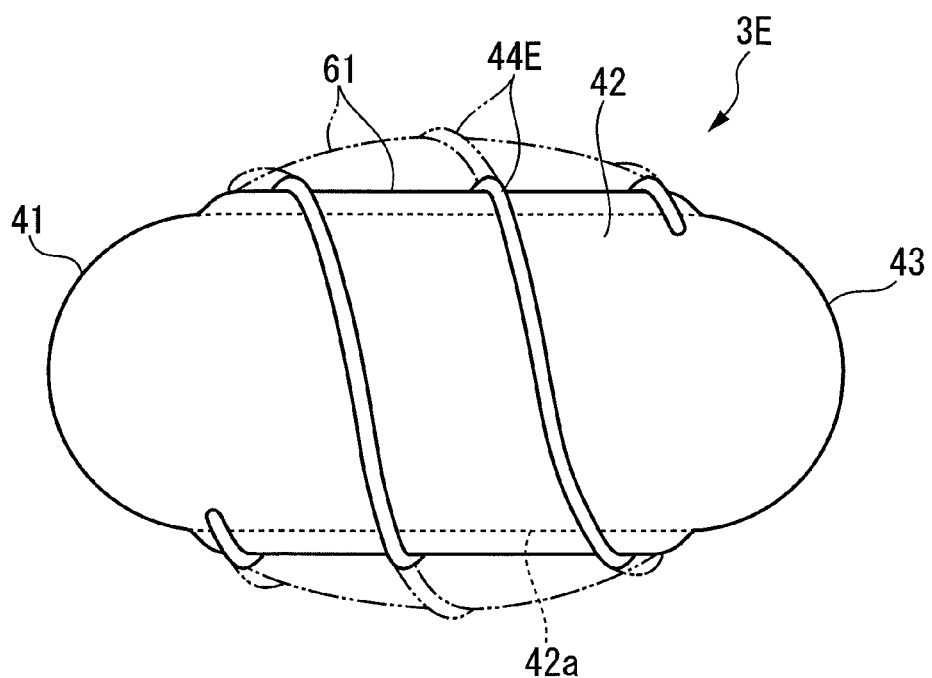
FIG. 32 illustrates how the spiral-outer-diameter of a spiral-structured portion changes as a balloon is inflated or deflated.
Figure 33:
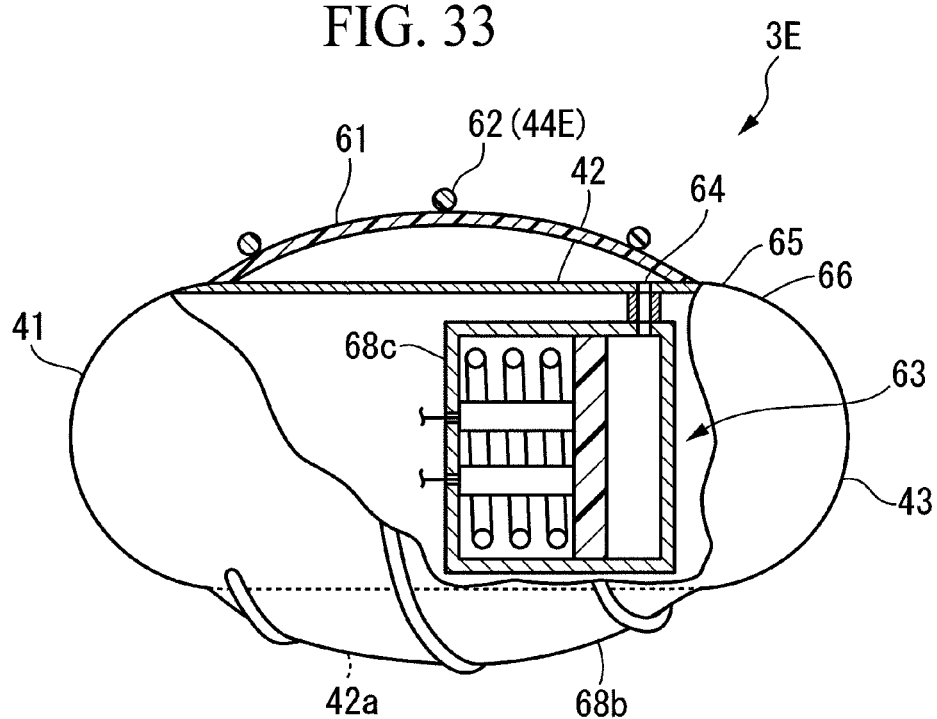
FIG. 33 illustrates a capsule-type medical apparatus with an inflated balloon.
Figure 34:
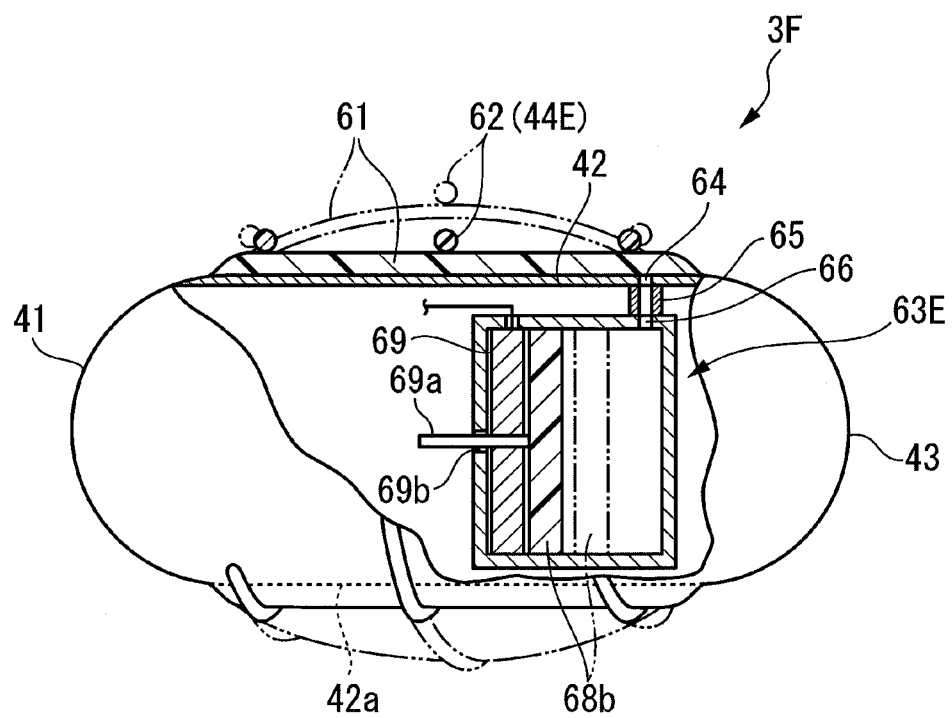
FIG. 34 is a schematic view of a first modification of the capsule-type medical apparatus of FIG. 31.
Figure 35:
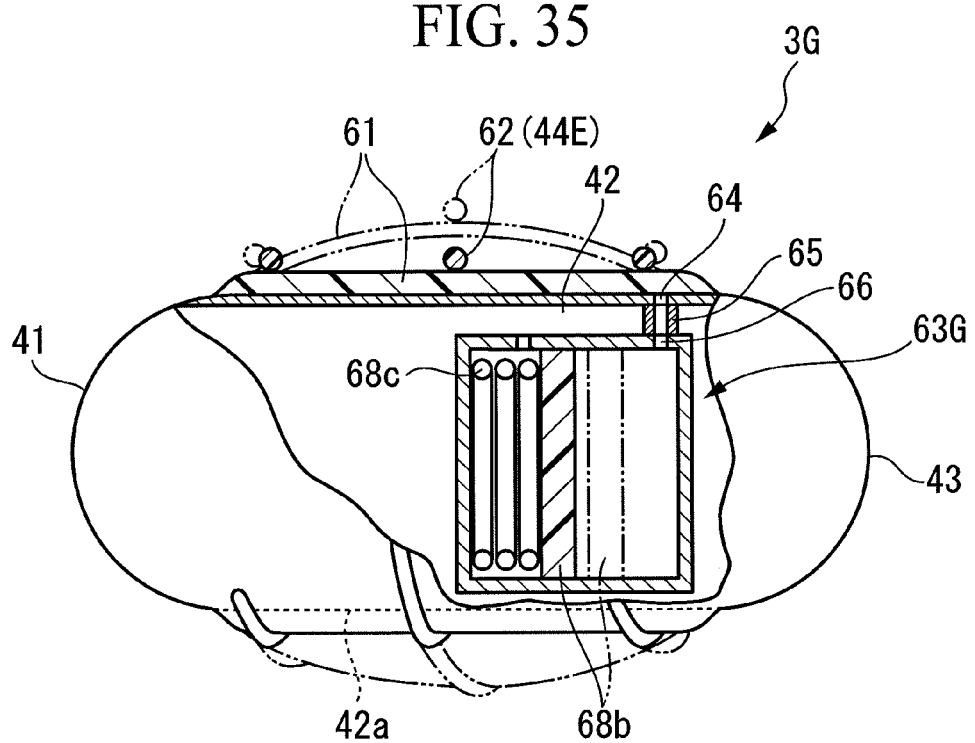
FIG. 35 is a schematic view of a second modification of the capsule-type medical apparatus of FIG. 31.
Figure 36:
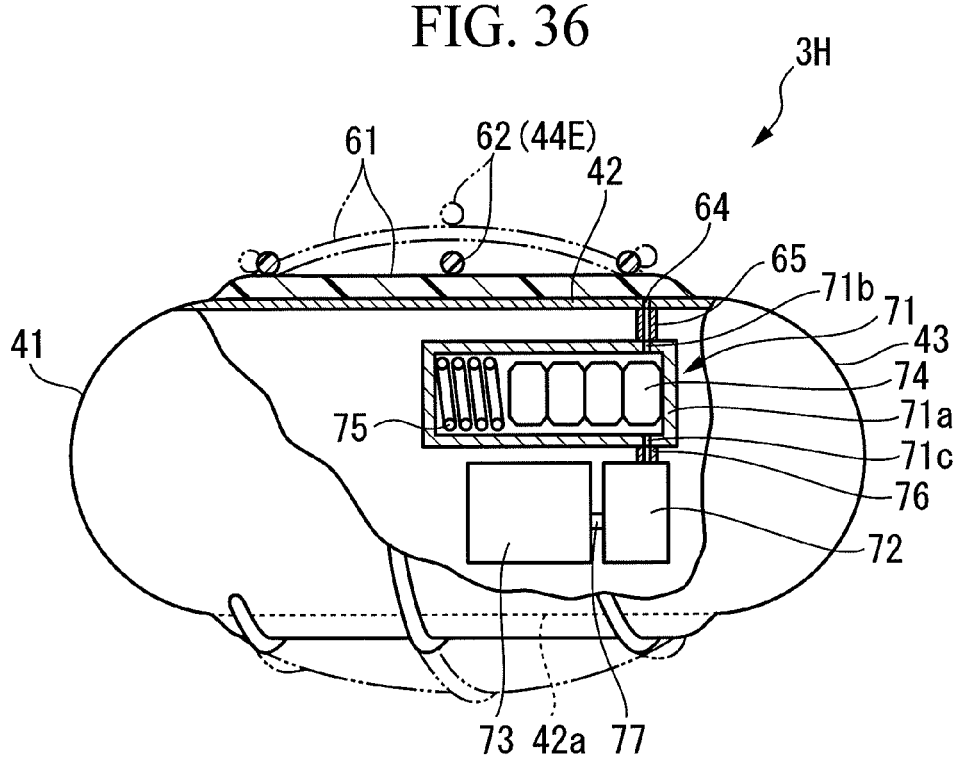
FIG. 36 is a schematic view of a third modification of the capsule-type medical apparatus of FIG. 31.

FIG. 31 to FIG. 36 relate to a sixth embodiment of the present invention. FIG. 31 illustrates a capsule-type medical apparatus according to the sixth embodiment of the present invention. FIG. 32 illustrates how the spiral-outer-diameter of a spiral-structured portion changes as a balloon is inflated or deflated. FIG. 33 illustrates a capsule-type medical apparatus with an inflated balloon. FIG. 34 is a schematic view of a first modification of the capsule-type medical apparatus of FIG. 31. FIG. 35 is a schematic view of a second modification of the capsule-type medical apparatus of FIG. 31. FIG. 36 is a schematic view of a third modification of the capsule-type medical apparatus of FIG. 31.

In the above-described fourth embodiment, the spiral-outer-diameter change-imparting portion is designed so as to change the spiral-outer-diameter by shifting the fixing position of one of the front end 44a and the rear end 44b of the spiral-structured portion 44 in the outer circumferential direction of the capsule 3. The sixth embodiment is constructed so as to provide a balloon between the capsule main body 42 and the spiral-structured portion and to change the spiral-outer-diameter of the spiral-structured portion by inflating and deflating this balloon. The components other than the above-described point are similar to those in the above-described fourth embodiment. The same components are denoted by the same reference numerals, and hence a description thereof will be omitted.

As shown in FIG. 31 to FIG. 33, in a capsule 3E of the sixth embodiment, a balloon (elastic membrane) 61 covering the capsule main body 42 is provided, and a spiral-structured portion 44E formed of an extensible elastic member such as an elastic tube or rubber or a tube 62 such as resin is provided on the outer circumferential surface of this balloon 61.

A cylinder portion 63 serving as balloon-inflation/deflation means for supplying/sucking a fluid such as gas or liquid to/from the balloon 61 is provided in the capsule main body 42. The balloon 61 communicates with a connection duct 65 via a through-hole 64 formed in the capsule main body 42, and this connection duct 65 communicates with a through-hole 66 formed in a cylinder wall of the cylinder portion 63.

In the cylinder portion 63, a piston 68b is provided at one end of an SMA wire 68a serving as a piston rod, and the other end is secured to a cylinder inner wall. Furthermore, in the cylinder portion 63, a coil spring 68c that constantly urges the piston 68b in a direction to inflate the balloon 61 is provided on the side where the SMA wire 68a is disposed.

As with the SMA coil 47 of the above-described fifth embodiment, the SMA wire 68a constitutes a closed circuit with a battery and a switch (not shown in the figure), and the switch is turned on/off by, for example, a control signal transmitted from the control apparatus 4 to supply or stop electrical power from the battery. When the switch is turned on and power is supplied from the battery, the SMA wire 68a contracts against the urging force of the coil spring 68c to slide the piston 68b along the cylinder inner wall in a direction to contract the balloon 61.

Thus, in the cylinder portion 63, the coil spring 68c always exert an urging force to slide the piston 68b in a direction to increase the spiral-outer-diameter of the spiral-structured portion 44E, thereby supplying a fluid to inflate the balloon 61. On the other hand, in the cylinder portion 63, when the SMA wire 68a is supplied with power, this SMA wire 68a contracts against the urging force of the coil spring 68c to slide the piston 68b along the cylinder inner wall in a direction to decrease the spiral-outer-diameter of the spiral-structured portion 44E, thereby sucking the fluid to contract the balloon 61. In short, the cylinder portion 63 constitutes the spiral-outer-diameter change-imparting portion.

By doing so, in the capsule 3E, the balloon 61 is provided between the capsule main body 42 and the spiral-structured portion 44E, and the spiral-outer-diameter of the spiral-structured portion 44E can be changed by inflating and deflating this balloon 61. The balloon 61 may be pre-compacted by a water-soluble substance compatible with living organisms, such as glycocalyx, so that the capsule 3E can be swallowed easily.

According to this embodiment, not only can similar advantages to those in the above-described fourth embodiment be provided, but also the spiral-outer-diameter of the spiral-structured portion 44E can be changed by providing the balloon 61 between the capsule main body 42 and the spiral-structured portion 44E and inflating and deflating this balloon 61. This ensures that the spiral-outer-diameter can be changed without causing the spiral shape to be deformed.

For the capsule, the cylinder portion may be embodied by an actuator instead of the SMA wire 68a. As shown in FIG. 34, a cylinder portion 63E provided in a capsule 3F includes an actuator 69 for pushing and pulling a piston rod 69a.

The piston rod 69a meshes with the actuator 69 through a through-hole 69b formed in the cylinder inner wall. The actuator 69 is an axially moving actuator that includes a pinion (not shown in the figure) meshing with the piston rod 69a and rotates this pinion with a motor (not shown in the figure) to push and pull the piston rod 69a in the axial direction. This actuator 69 is connected to a control circuit (not shown in the figure), which controls and drives the actuator 69 based on a control signal transmitted from the control apparatus 4.

Therefore, the cylinder portion 63E moves the piston rod 69a forward in the axial direction by the actuator 69 to slide the piston 68b in a direction to increase the spiral-outer-diameter of the spiral-structured portion 44E, thereby supplying a fluid to inflate the balloon 61. On the other hand, the cylinder portion 63E moves the piston rod 69a backward in the axial direction by the actuator 69 to slide the piston 68b along the cylinder inner wall in a direction to reduce the spiral-outer-diameter of the spiral-structured portion 44E, thereby sucking the fluid to contract the balloon 61. Consequently, as in the above-described sixth embodiment, the capsule 3F can change the spiral-outer-diameter of the spiral-structured portion 44E.

Furthermore, in the capsule, the cylinder portion may include only the coil spring 68c and the piston 68b. As shown in FIG. 35, a cylinder portion 63G provided in a capsule 3G includes only the coil spring 68c and the piston 68b.

The coil spring 68c constantly urges the piston 68b in a direction to inflate the balloon 61. By doing so, in the capsule 3G, the spiral-structured portion 44E is subjected to an external force in contact with the wall in the lumen against the urging force of the coil spring 68c, and thereby, the spiral-structured portion 44E comes to have an optimal spiral-outer-diameter according to the contact with the wall in the lumen, which produces a stable propulsion force by ensuring an appropriate spiral shape of the spiral-structured portion 44E.

According to this modification, the spiral-outer-diameter of the spiral-structured portion 44E can be changed automatically according to the diameter of the passage inside the body cavity. Furthermore, since the capsule 3G of this modification does not require energy for controlling the spiral-outer-diameter of the spiral-structured portion 44E and is simple in structure, it can be made small. In addition, since a force in a direction to increase the spiral-outer-diameter constantly exists in the capsule 3G of this modification, the spiral-structured portion 44E can be held in contact with the wall in the lumen, which produces a stable propulsion force and therefore improves the ease of insertion in the depth direction of the passage inside the body cavity.

In addition, the capsule may be constructed so as to inflate the balloon 61 using an inflatant. As shown in FIG. 36, a capsule 3H includes an inflatant storage section 71, a pump 72, and a water tank 73 as balloon-inflation/deflation means in the capsule main body 42.

The inflatant storage section 71 is constructed so as to urge a plurality of inflatant tablets 74 stored in a storage compartment 71a onto a wall surface of the storage compartment 71a by a coil spring 75. A through-hole 71b communicating with the connection duct 65 and a through-hole 71c communicating with a connection duct 76 connecting to the pump 72 are formed in this storage compartment 71a. The through-hole 71c is formed at a location where the inflatant tablet 74 located at the endmost position due to the urging force of the coil spring 75 is splashed with water supplied from the water tank 73 via the pump 72.

The pump 72 sucks the water stored in the water tank 73 via a connection duct 77 connecting to the water tank 73 and supplies the water to the inflatant tablet 74 of the inflatant storage section 71 via the through-hole 71c. The pump 72 is connected to a pump control circuit (not shown in the figure), which controls and drives the pump 72 based on a control signal transmitted from the control apparatus 4.

By doing so, the inflatant storage section 71 receives water from the water tank 73 via the pump 72 and causes the endmost inflatant tablet 74 to vaporize through reaction with this supplied water to inflate the balloon 61. The inflatant tablets 74 include, for example, sodium hydrogen carbonate and tartaric acid as the main ingredients and produce carbon dioxide through this reaction.

The balloon 61 is provided with a pressure release valve (not shown in the figure) so as to automatically release gas when the pressure exceeds a predetermined value. The pressure release valve may be a pressure-regulating valve so as to actively control the expansion of the balloon 61. When this balloon 61 is to be inflated, the inflatant tablet 74 that comes to the endmost position through the urging force of the coil spring 75 is reacted.

By doing so, as in the above-described sixth embodiment, the capsule 3H can change the spiral-outer-diameter of the spiral-structured portion 44E. According to this modification, since pressure for inflating the balloon 61 can be produced through chemical reaction, only a small quantity of energy is required to inflate the balloon 61. This reduces energy consumption and reduces the size of the battery. In the capsule 3H, instead of providing the water tank 73 in the capsule main body 42, a bodily fluid of the subject may be sucked into the capsule main body 42, causing the inflatant tablets 74 to react with the bodily fluid.

Seventh Embodiment

Figure 37:
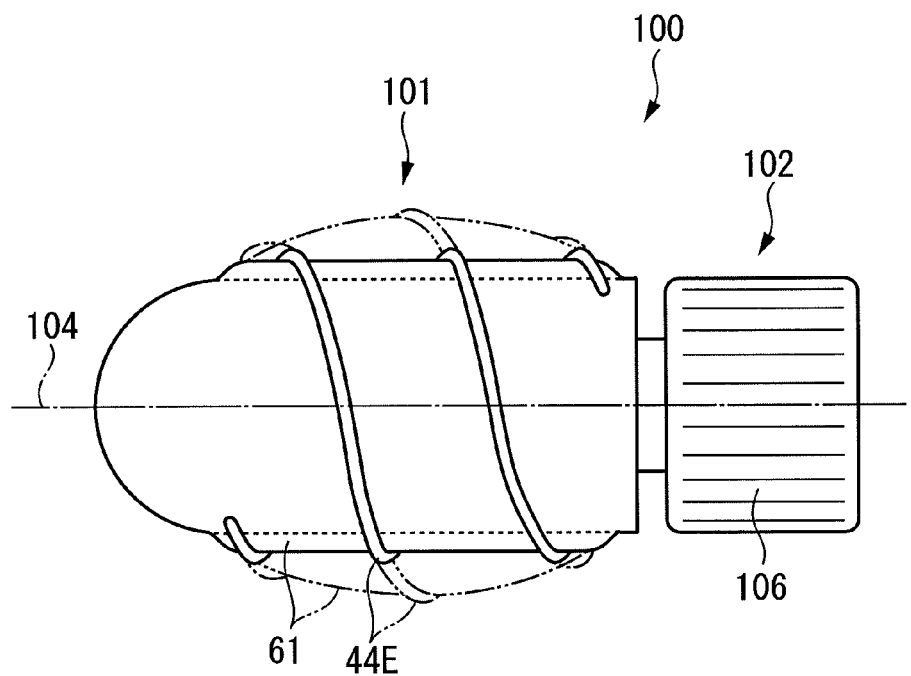
FIG. 37 illustrates a capsule-type medical apparatus according to a seventh embodiment of the present invention.
Figure 38:
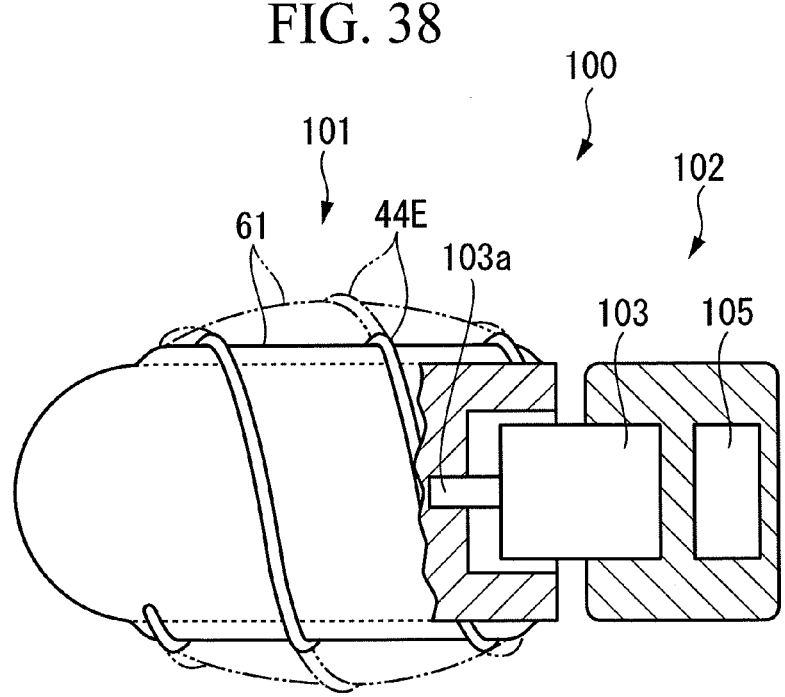
FIG. 38 is a schematic view of the structure of the capsule-type medical apparatus of FIG. 37.
Figure 39:
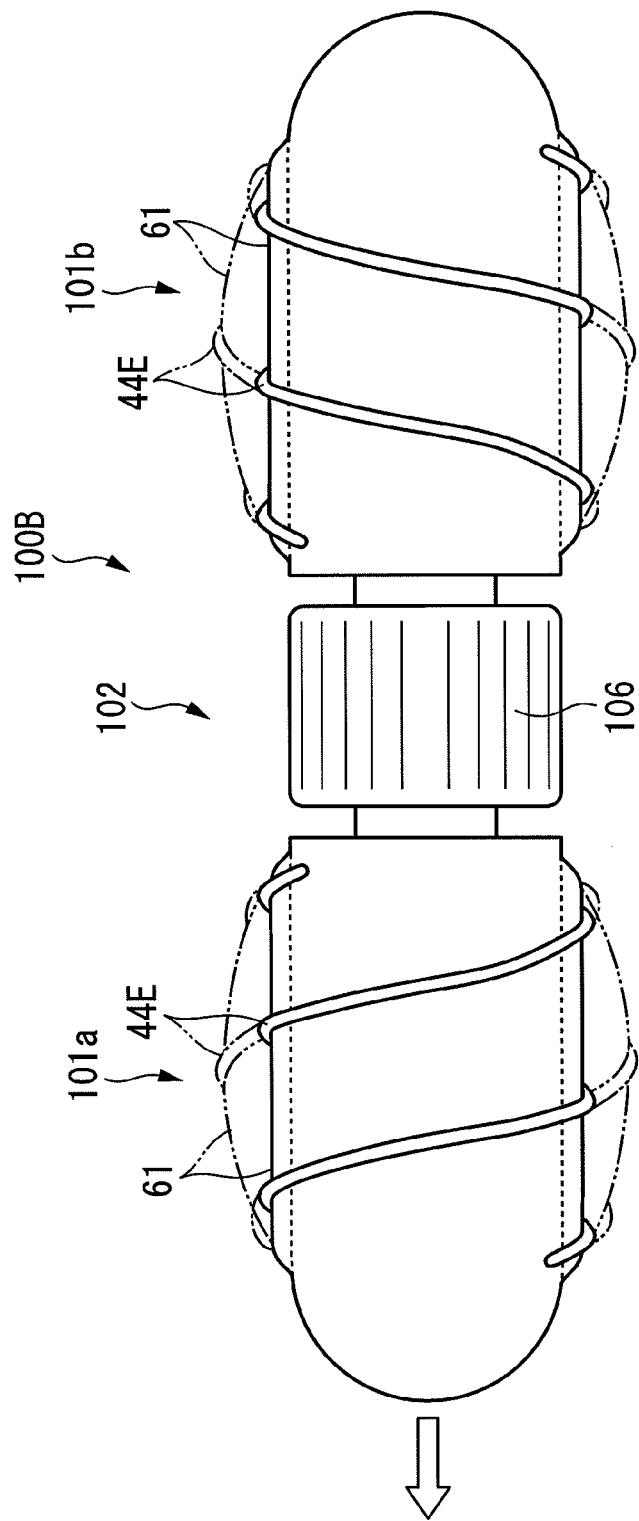
FIG. 39 illustrates a modification of the capsule-type medical apparatus of FIG. 37.
Figure 40:
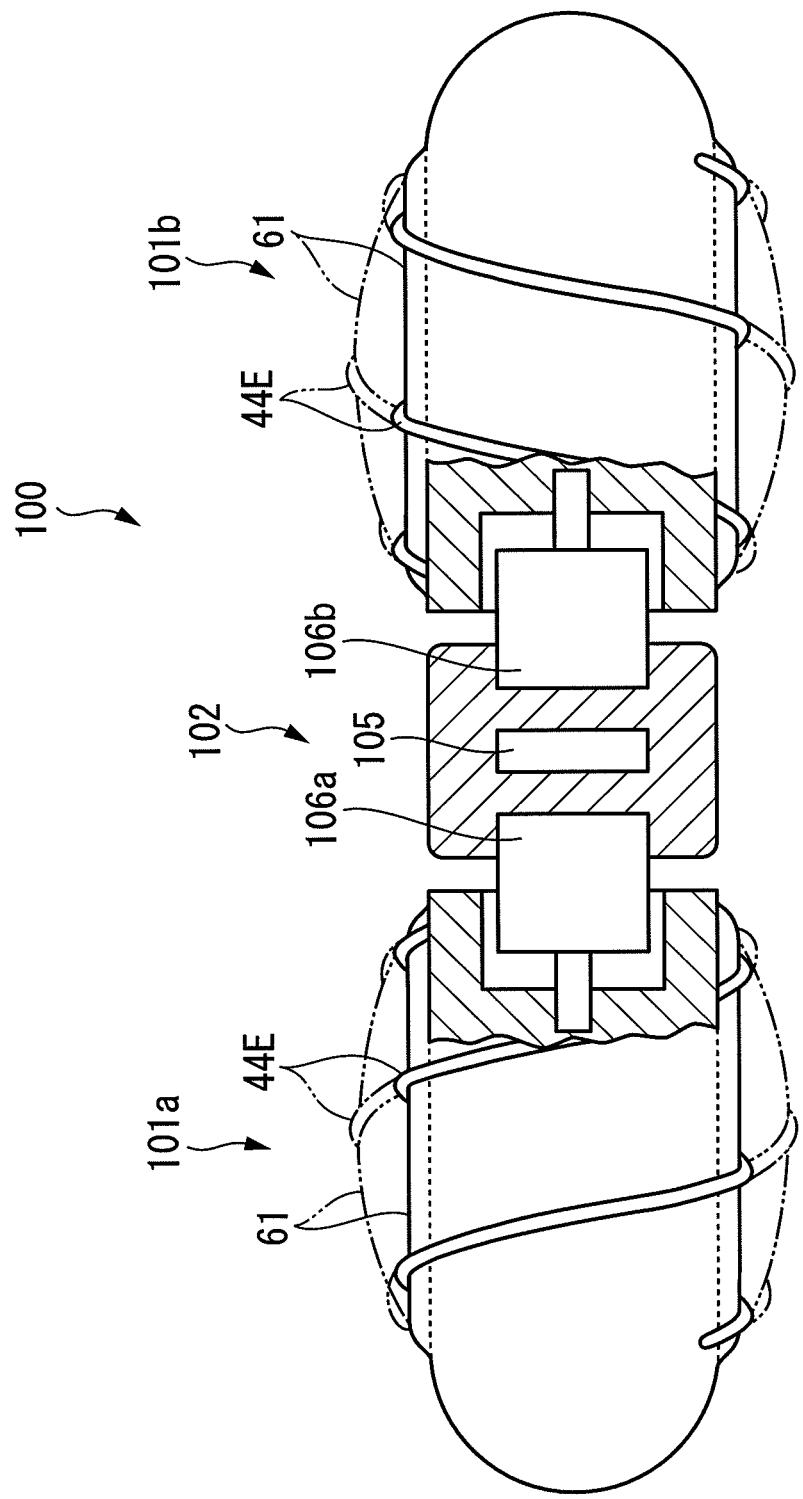
FIG. 40 is a schematic view of the structure of the capsule-type medical apparatus of FIG. 39.

FIG. 37 to FIG. 40 relate to a seventh embodiment of the present invention. FIG. 37 illustrates a capsule-type medical apparatus according to the seventh embodiment of the present invention. FIG. 38 is a schematic view of the structure of the capsule-type medical apparatus of FIG. 37. FIG. 39 illustrates a modification of the capsule-type medical apparatus of FIG. 37. FIG. 40 is a schematic view of the structure of the capsule-type medical apparatus of FIG. 39.

In the above-described fourth embodiment to sixth embodiment, the magnet provided in the capsule is acted upon by a revolving magnetic field generated by the magnetic-field generating apparatus provided around the patient, thus rotating the capsule. The seventh embodiment is constructed so as to include a motor in the capsule to cause this capsule to rotate autonomously. The components other than the above-described point are similar to those in the above-described fourth embodiment. The same components are denoted by the same reference numerals, and hence a description thereof will be omitted.

As shown in FIG. 37 and FIG. 38, a capsule 100 of the seventh embodiment includes a capsule main body 101 and a rotary base 102 for rotating this capsule main body 101.

Although not shown in the figure, the capsule main body 101 includes components such as the signal processing circuit 24, the memory 25, the wireless circuit 26, the antenna 27, the capsule control circuit 28, and the battery 29, in addition to the objective optical system 21, the imaging element 22, and the illuminating element 23, which are similar to those in above-described fourth embodiment. In addition, as in the above-described sixth embodiment, the capsule main body 101 is provided with the balloon 61 covering the capsule main body 101 and the spiral-structured portion 44E formed of the tube 62, serving as an elastic member, on the outer circumferential surface of this balloon 61. As in the above-described sixth embodiment or modifications thereof, the capsule main body 101 includes balloon-inflation/deflation means for inflating and deflating the balloon 61. In addition, the balloon 61 may be pre-compacted by a water-soluble substance compatible with living organisms, such as glycocalyx, so that the capsule 100 can be swallowed easily.

The rotary base 102 includes a motor 103 as a rotary mechanism for rotating the capsule main body 101. This motor 103 is, for example, a rotary motor. A motor shaft 103a of the motor 103 is firmly fitted with a rear-end portion of the capsule main body 101 and rotates the capsule main body 101 relative to the rotary base 102.

By doing so, the capsule main body 101 rotates relative to the rotary base 102 due to the rotary force of the motor 103, and the spiral-structured portion 44E converts this rotation into propulsion (propulsion force) to produce a propulsion force in the spiral axial direction (the direction of a spiral axis 104). The motor 103 is supplied with power from a second battery 105 provided in the rotary base 102.

In addition, a plurality of grooves 106 parallel to the longitudinal axis is formed on the outer surface of the rotary base 102. By doing so, the capsule 100 prevents the rotary base 102 from rotating relative to the wall in the lumen without preventing propulsion. In the rotary base 102, angle-detection means (not shown in the figure) for angle-correcting images may be provided in the motor 103. In this case, the capsule 100 externally transmits angle information, associated with information (data) signal such as a video signal, from the angle-detection means.

The capsule 100 with the above-described structure is swallowed by the patient and inserted into the passage inside the body cavity. The capsule 100 is supplied with power from the second battery 105, and thereby the motor 103 is driven to rotate the capsule main body 101. The capsule main body 101 receives a rotary force from the motor shaft 103a of the motor 103 and rotates relative to the rotary base 102 with this rotary force of the motor 103. At this time, as described above, the rotary base 102 prevents rotation relative to the wall in the lumen without preventing propulsion by means of the grooves 106 formed on the outer surface thereof.

In the capsule 100, the rotation of the capsule main body 101 generates a propulsion force, at the point of contact between the spiral-structured portion 44E and the wall in the lumen, and this propulsion force advances the capsule main body 101 as if a male screw were engaged with a female screw. As a result, the capsule main body 101 produces a propulsion force in the spiral axial direction (direction of the spiral axis 104), and thereby the capsule 100 can move forward.

According to this embodiment, not only can advantages similar to those in the above-described fourth embodiment be provided, but also the capsule 100 can autonomously move because of the built-in motor 103 functioning as a rotary mechanism. Therefore, an external apparatus, such as the magnetic induction apparatus including the magnetic-field generating apparatus 5 and the AC power supply unit 6, is not required. This allows the overall size of the system to be reduced.

In the capsule 100 of this embodiment, as in the above-described sixth embodiment, the balloon 61 is provided between the capsule main body 101 and the spiral-structured portion 44E, and the spiral-outer-diameter of the spiral-structured portion 44E is changed by inflating and deflating this balloon 61. However, the present invention is not limited to this, and the spiral-outer-diameter of the spiral-structured portion 44 may be changed by providing a mechanism similar to that in the above-described fourth embodiment or fifth embodiment.

The capsule may be constructed by providing two of the capsule main bodies 101 with the rotary base 102 interposed therebetween. As shown in FIG. 39 and FIG. 40, the capsule 100B is constructed by providing two of the capsule main bodies 101 with the rotary base 102 interposed therebetween.

More specifically, the capsule 100B includes the rotary base 102; and a front capsule body 101a and a rear capsule body 101b that rotate relative to the rotary base 102 by a first motor 106a and a second motor 106b mounted on this rotary base 102. The front capsule body 101a and the rear capsule body 101b are constructed such that the spiral-structured portions 44E formed in the balloons 61 are oriented opposite to each other. The term "front" is defined as the direction in which the imaging element 22 faces.

The first motor 106a for rotating the front capsule body 101a; the second motor 106b for rotating the rear capsule body 101b; and the second battery 105 that supplies power for driving the first motor 106a and the second motor 106b are provided in the rotary base 102.

As a result, even when the capsule 100B cannot advance in the case where one capsule main body 101 (the front capsule body 101a or the rear capsule body 101b) is not in contact with the wall in the lumen, the capsule 100B can move forward by assisting the other capsule main body 101 (the rear capsule body 101b or the front capsule body 101a) to come into contact with the wall in the lumen.

Although, in the capsule 100B, the spiral-structured portions 44E provided in the front capsule body 101a and the rear capsule body 101b are wound in the opposite directions to each other, the present invention is not limited to this. The spiral-structured portions 44E may be wound in the same directions. In this case, the front capsule body 101a and the rear capsule body 101b rotate so as to have the same propulsion direction.

Eighth Embodiment

Figure 41:
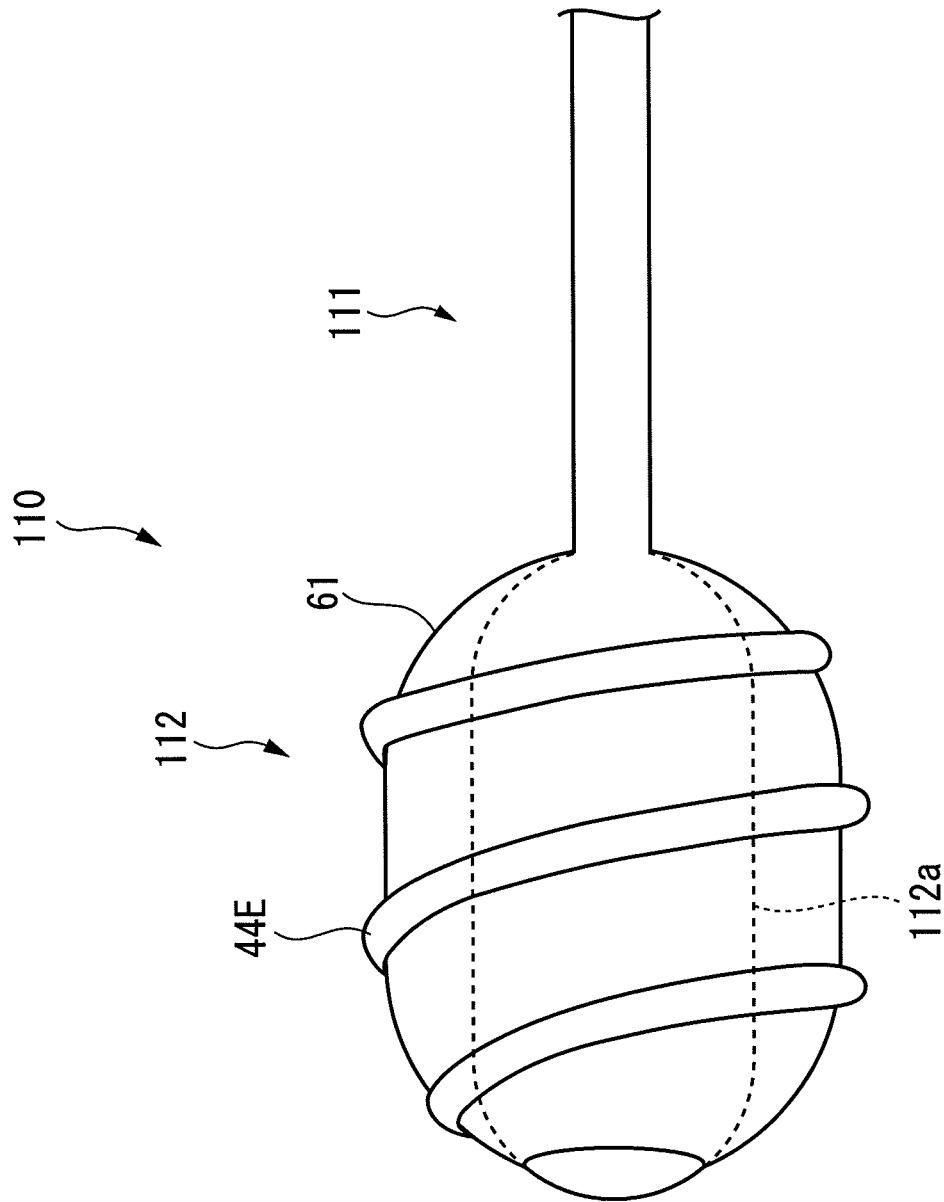
FIG. 41 illustrates an endoscope insertion portion according to an eighth embodiment of the present invention.
Figure 42:
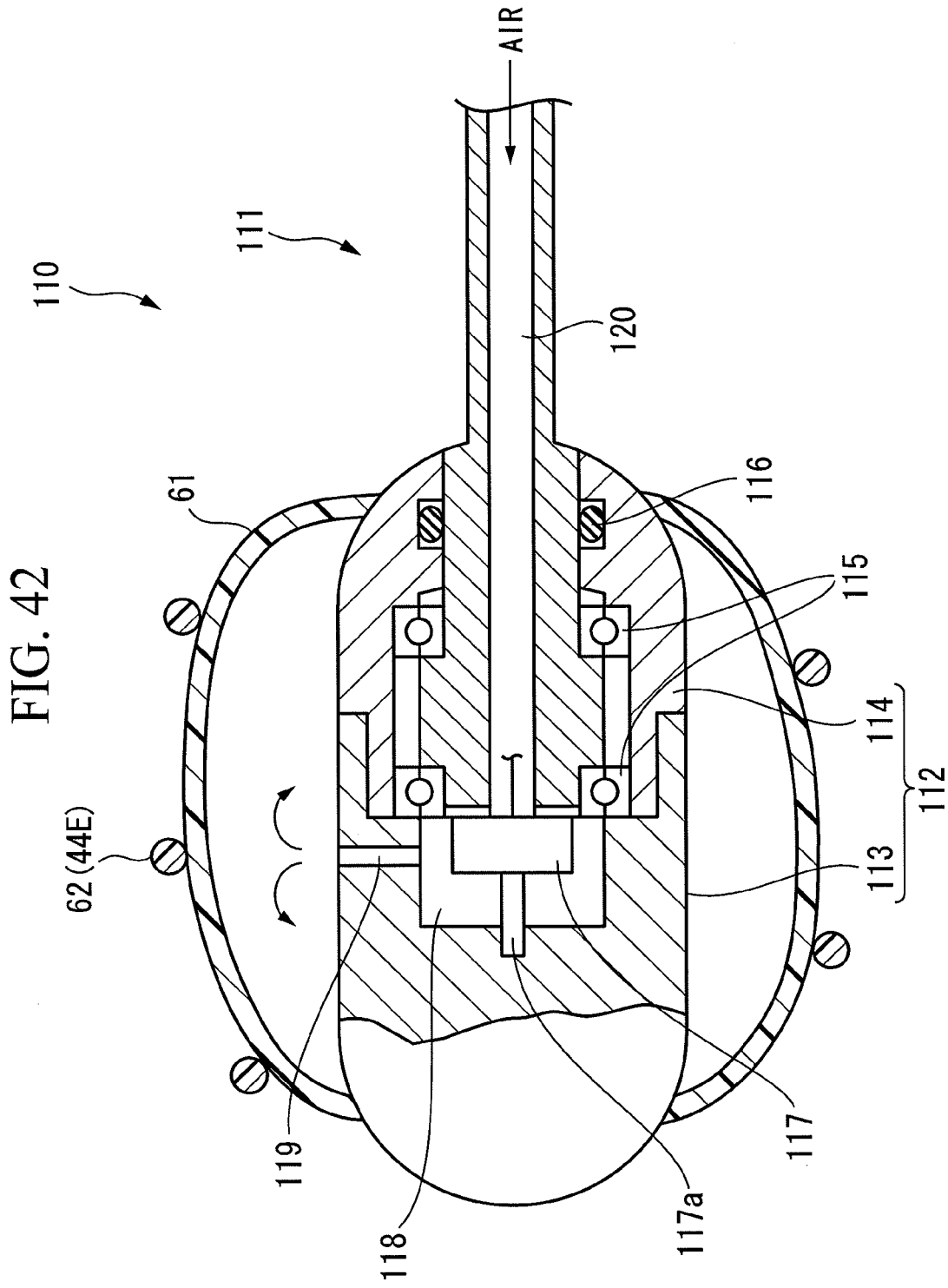
FIG. 42 is a schematic view of the structure of the endoscope insertion portion of FIG. 41.

FIG. 41 and FIG. 42 relate to an eighth embodiment of the present invention. FIG. 41 illustrates an endoscope insertion portion according to an eighth embodiment of the present invention. FIG. 42 is a schematic view of the structure of the endoscope insertion portion of FIG. 31.

The above-described fourth embodiment to the seventh embodiment are constructed as an intrasubject insertion apparatus by applying the present invention to a capsule that is movable independently in a passage inside the body cavity. The eighth embodiment is constructed by applying the present invention to an endoscope insertion portion that has at a tip thereof a capsule-shaped portion as an intrasubject insertion apparatus. The components other than the above-described point are similar to those in the above-described fourth embodiment. The same components are denoted by the same reference numerals, and hence a description thereof will be omitted.

As shown in FIG. 41 and FIG. 42, an endoscope insertion portion 110, serving as an intrasubject insertion apparatus of the eighth embodiment, includes a capsule-shaped portion 112 at a tip of an elongated, flexible insertion tube 111 that is inserted into the passage inside the body cavity.

As in the above-described sixth embodiment, the capsule-shaped portion 112 is provided with the balloon 61 on an outer surface 112a of the capsule-shaped portion 112, and furthermore, the spiral-structured portion 44E formed of the tube 62, serving as an elastic member, is provided on the outer circumferential surface of this balloon 61. The balloon 61 may be pre-compacted by a water-soluble substance compatible with living organisms, such as glycocalyx, so that the capsule-shaped portion 112 can be swallowed easily. The capsule-shaped portion 112 is integrally formed by securing a front-end container 113 and a rear-end container 114 with an adhesive. Although not shown in the figure, the front-end container 113 includes components such as the objective optical system 21, the imaging element 22, and the illuminating element 23 similar to those in above-described fourth embodiment.

A front-end side of the insertion tube 111 is attached to the rear-end container 114, which is rotatable relative to this insertion tube 111 by means of bearings 115. A hermetic structure is achieved with an O ring 116 between the rear-end container 114 and the insertion tube 111. By doing so, in the capsule-shaped portion 112, the front-end container 113 and the rear-end container 114 are integrally rotatable relative to the insertion tube 111.

A motor 117 that integrally rotates the front-end container 113 and the rear-end container 114 is attached to a front-end side of the insertion tube 111. A motor storage compartment 118 for accommodating the motor 117 is provided in the front-end container 113. A motor shaft 117a of the motor 117 is fitted to a storage wall of the motor storage compartment 118. By doing so, the motor 117 can rotate the capsule-shaped portion 112 relative to the insertion tube 111.

A through-hole 119 extending from the motor storage compartment 118 to the outer circumferential surface is formed in the front-end container 113 so that air can be supplied to the balloon 61 via the motor storage compartment 118. A duct 120 for supplying air to the balloon 61 is formed in the insertion tube 111. Signal lines, such as the signal line for transmitting video signals received from the imaging element 22 and the power supply line of the motor 117, are routed in this duct.

The rear end of the insertion tube 111 is connected to a control apparatus (not shown in the figure). This control apparatus is provided with a compressor for supplying air into the balloon 61, as well as a motor control circuit for controlling/driving the motor 117 and a data processing circuit for processing, for example, video signals.

The endoscope insertion portion 110 with the above-described structure is inserted into the passage inside the body cavity. The endoscope insertion portion 110 is supplied with power from the control apparatus, and thereby, the motor 117 is driven to rotate the capsule-shaped portion 112. The endoscope insertion portion 110 is moved forward as the rotation of the capsule-shaped portion 112 generates a propulsion force, at the point of contact between the spiral-structured portion 44E and the wall in the lumen, and this propulsion force advances the capsule-shaped portion 112 as if a male screw were engaged with a female screw.

At this time, if a sufficiently large propulsion force cannot be produced because the diameter of the passage inside the body cavity is too large, compared to the spiral-outer-diameter of the spiral-structured portion 44E, to achieve satisfactorily close contact between the wall in this lumen and the spiral-structured portion 44E, the operator operates the control apparatus to increase the spiral-outer-diameter of the spiral-structured portion 44E. The control apparatus drives the compressor to supply air into the endoscope insertion portion 110.

The endoscope insertion portion 110 is supplied with air via the duct 120 of the insertion tube 111, and this air is guided from the motor storage compartment 118 of the capsule-shaped portion 112 to the balloon 61 via the through-hole 119. The balloon 61 inflates to increase the spiral-outer-diameter of the spiral-structured portion 44E. Consequently, the endoscope insertion portion 110 can obtain a sufficiently large propulsion force since the spiral-outer-diameter of the spiral-structured portion 44E can be increased to achieve appropriate contact between the wall in the lumen and the spiral-structured portion 44E.

In contrast, if the spiral-outer-diameter of the spiral-structured portion 44E exceeds the diameter of the passage in the body cavity, the operator operates the control apparatus to reduce the spiral-outer-diameter of the spiral-structured portion 44E. The control apparatus drives the compressor to suck air from the endoscope insertion portion 110. In this case, in the endoscope insertion portion 110, air is sucked from the balloon 61 via the route in the opposite direction to that in the case where air is supplied. The balloon 61 contracts to reduce the spiral-outer-diameter of the spiral-structured portion 44E.

Consequently, the endoscope insertion portion 110 can obtain a sufficiently large propulsion force since the spiral-outer-diameter of the spiral-structured portion 44E can be reduced to achieve appropriate contact between the wall in the lumen and the spiral-structured portion 44E. Thus, the endoscope insertion portion 110 can change the spiral-outer-diameter of the spiral-structured portion 44E according to the diameter of the passage inside the body cavity.

As described above, according to this embodiment, since the spiral-outer-diameter of the spiral-structured portion 44E can be changed according to the diameter of the passage in the body cavity, a stable propulsion force can be obtained by ensuring an appropriate spiral shape of the spiral-structured portion 44E. In addition, since air is supplied from the insertion tube 111 in the endoscope insertion portion 110 of this embodiment, the capsule-shaped portion 112 does not need to include, for example, a pump and therefore, the size of the capsule-shaped portion 112 can be reduced. Furthermore, according to the endoscope insertion portion of this embodiment, air supply to the balloon 61 and air discharge from the balloon 61 can be carried out by directly operating the control apparatus close at hand. This ensures high operability. The endoscope insertion portion 110 may be constructed such that the capsule-shaped portion 112 is detachable from the insertion tube 111.

Furthermore, as in the above-described sixth embodiment, the endoscope insertion portion 110 of this embodiment is constructed to have the balloon 61 between the capsule-shaped portion 112 and the spiral-structured portion 44E and to change the spiral-outer-diameter of the spiral-structured portion 44E by inflating and deflating this balloon 61. The present invention is not limited to this, however, and the spiral-outer-diameter of the spiral-structured portion 44 may be changed by providing a mechanism similar to that in the above-described fourth embodiment or fifth embodiment.

Furthermore, although the endoscope insertion portion 110 is constructed by providing the balloon 61 on the capsule-shaped portion 112 at the front-end portion and forming the spiral-structured portion 44E on this balloon 61. The present invention is not limited to this. The balloon 61 may be provided at a plurality of locations on the insertion tube 111, and the spiral-structured portions 44E may be formed on these balloons 61.

Furthermore, although this embodiment is constructed by applying the present invention to the endoscope insertion portion 110, the present invention is not limited to this. The present invention may be applied to, for example, a probe having a capsule-shaped portion at a tip thereof and an insertion tool for guiding an endoscope insertion portion deep inside the passage in the body cavity.

Embodiments realized by combining part of each of the above-described first embodiment to eighth embodiment also constitute the present invention.

The invention claimed is:

1. A medical capsule endoscope which is inserted into the body of a subject and is guided by an external magnetic field, the medical capsule endoscope comprising:
   a substantially cylindrical capsule;
   a magnet accommodated inside the capsule and configured so that a magnetic-pole direction thereof can be switched between a direction along a longitudinal axis and a direction intersecting the longitudinal axis; and
   a securing portion for securing the magnet to the capsule in each of the switched states of the magnetic-pole direction
   wherein the magnet is secured by the securing portion in one of a first state in which magnetic poles of the magnet are aligned in a direction along the longitudinal axis of the capsule, and a second state in which the magnetic poles of the magnet are in a direction orthogonal to the longitudinal axis of the capsule.

2. The medical capsule endoscope according to claim 1, wherein
   the magnet is made of a permanent magnet, and
   the securing portion includes an engagement member which is engaged with the magnet at a location where magnetic poles are oriented in a direction along the longitudinal axis and at a location where the magnetic poles are oriented in the direction intersecting the longitudinal axis.

3. The medical capsule endoscope according to claim 2, comprising:
a magnetic-pole-direction switching device for switching the magnetic-pole direction of the magnet, wherein
the magnetic-pole-direction switching device includes a motor for pivoting the magnet about an axis along a radial direction of the capsule.

4. The medical capsule endoscope according to claim 1, wherein in the first state, the capsule is rotated about the longitudinal axis of the capsule by the external magnetic field, and
in the second state, the direction of the longitudinal axis of the capsule is changed by the external field.

* * * * *